United States Patent
Hayashi et al.

(10) Patent No.: US 8,703,447 B2
(45) Date of Patent: Apr. 22, 2014

(54) PROCESS FOR PRODUCTION OF L-GLUTAMINE OR L-GLUTAMIC ACID

(75) Inventors: Mikiro Hayashi, Ibaraki (JP); Kazuhiko Tabata, Los Angeles, CA (US); Yoshiyuki Yonetani, Tokyo (JP)

(73) Assignee: Kyowa Hakko Bio Co., Ltd., Tokyo (JP)

( * ) Notice: Subject to any disclaimer, the term of this patent is extended or adjusted under 35 U.S.C. 154(b) by 91 days.

(21) Appl. No.: 13/520,947

(22) PCT Filed: Jan. 7, 2011

(86) PCT No.: PCT/JP2011/050207
§ 371 (c)(1),
(2), (4) Date: Aug. 30, 2012

(87) PCT Pub. No.: WO2011/083859
PCT Pub. Date: Jul. 14, 2011

(65) Prior Publication Data
US 2012/0322115 A1    Dec. 20, 2012

(30) Foreign Application Priority Data
Jan. 8, 2010    (JP) ................. 2010-002703

(51) Int. Cl.
C12P 13/14    (2006.01)
C12P 13/04    (2006.01)

(52) U.S. Cl.
USPC .......................................... 435/110; 435/106

(58) Field of Classification Search
None
See application file for complete search history.

(56) References Cited

U.S. PATENT DOCUMENTS

| 5,275,940 A | 1/1994 | Kino et al. |
| 2002/0102665 A1 | 8/2002 | Kino et al. |

FOREIGN PATENT DOCUMENTS

| JP | 55-148094 A | 11/1980 |
| JP | 03-232497 A | 10/1991 |
| JP | 04-112795 A | 4/1992 |
| JP | 05-084067 A | 4/1993 |
| JP | 2001-157596 A | 6/2001 |
| JP | 2002-300887 A | 10/2002 |
| JP | 2003-164297 A | 6/2003 |

OTHER PUBLICATIONS

Bagel et al., *Antimicrobial Agents and Chemotherapy*, 43(4): 868-875 (1999).
Castillo et al., *Proc. Natl. Acad. Sci. USA*, 88: 8860-8864 (1991).
Drew et al., *EMBO Journal*, 4(4): 1025-1032 (1985).
Free et al., *Molecular Microbiology*, 14(1): 151-161 (1994).
Jakoby et al., FEMS Microbiology Letters, 173: 303-310 (1999).
Lewis et al., *J. Mol. Biol.*, 66: 131-142 (1972).
Nolden et al., *FEMS Microbiology Letters*, 201: 91-98 (2001).
Rudd et al., *Proc. Natl. Acad. Sci. USA*, 84: 517-521 (1987).
Toone et al., *Journal of Bacteriology*, 174(16): 5479-5481 (1992).
Japanese Patent Office, International Search Report in International Patent Application No. PCT/JP2011/050207 (Feb. 1, 2011).

*Primary Examiner* — Suzanne M Noakes
*Assistant Examiner* — Jae W Lee
(74) *Attorney, Agent, or Firm* — Leydig, Voit & Mayer, Ltd.

(57) ABSTRACT

Provided is an efficient process for producing L-glutamine or L-glutamic acid using a microorganism. L-glutamine or L-glutamic acid is produced by culturing in a medium a microorganism in which has an ability to produce L-glutamine or L-glutamic acid, and in which an ability to form a superhelical double-stranded DNA is decreased compared with that of the parent strain, producing and accumulating L-glutamine or L-glutamic acid in the medium, and recovering L-glutamine or L-glutamic acid from the medium.

4 Claims, No Drawings

PROCESS FOR PRODUCTION OF L-GLUTAMINE OR L-GLUTAMIC ACID

CROSS-REFERENCE TO RELATED APPLICATIONS

This patent application is the U.S. national phase of International Patent Application No. PCT/JP2011/050207, filed Jan. 7, 2011, which claims the benefit of Japanese Patent Application No. 2010-002703, filed Jan. 8, 2010, which are incorporated by reference in their entireties.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 185,145 bytes ASCII (Text) file named "710691SequenceListing.txt," created Jul. 5, 2012.

TECHNICAL FIELD

The present invention relates to a microorganism to be used for the efficient production of L-glutamine or L-glutamic acid, and an efficient process for producing L-glutamine or L-glutamic acid, comprising culturing said microorganism in a medium.

BACKGROUND ART

Examples of the process for producing L-glutamine by a fermentation method include methods using a mutant strain imparted with amino acid analogue resistance, such as a method using a coryneform bacterium imparted with azaserine resistance (patent document 1), a method using coryneform bacterium imparted with 6-diazo-5-oxo-norleucine resistance (patent document 2) and the like, a method for increasing glutamine synthetase activity involved in the synthesis of L-glutamine and the like. Specific examples of known method for increasing glutamine synthetase activity involved in the synthesis of L-glutamine include decrease of the activity of glutamine synthetase adenylyltransferase which is a controller via adenylylation (non-patent document 1, patent document 3), substitution of the 405th amino acid residue of glutamine synthetase that is subject to adenylylation (non-patent document 1, patent document 4), decrease of a PII protein activity (non-patent document 2, patent document 3) and the like.

Examples of known process for producing L-glutamic acid according to the fermentation method include a method of culturing coryneform bacterium or a mutant strain thereof under biotin-limited conditions, and a method of culturing same with the addition of penicillin and a surfactant (non-patent document 3).

It has been clarified that a superhelical structure of chromosomal DNA plays an important role in controlling the synthesis of ribosomal RNA and transfer RNA in bacteria. DNA gyrase, which is one kind of type II DNA topoisomerase, has an activity to cleave and ligate double-stranded DNA, and converts positive superhelical DNA or relaxed DNA to negative superhelical DNA in the presence of ATP. It is known that, in a DNA gyrase mutant strain of *Escherichia coli*, the expression level of operon involved in L-histidine synthesis is increased and expression of some tRNAs including His-tRNA is decreased (non-patent document 4). On the other hand, type I DNA topoisomerase has an activity to cleave one chain of DNA and relaxes superhelical DNA.

*Escherichia coli* is known to show improved expression of His-tRNA and Tyr-tRNA once type I DNA topoisomerase becomes defective (non-patent document 5). Furthermore, this effect is known to be complemented by introduction of a plasmid in which a gene encoding a subunit of type I or IV DNA topoisomerase is cloned (non-patent document 5).

It is known that L-histidine producibility is increased by imparting resistance to a DNA gyrase inhibitor to *Escherichia coli* having L-histidine productivity (patent document 5). However, it is not known at all heretofore that an enzyme involved in DNA topology is involved in the improvement of productivity of amino acid other than L-histidine and modification of an enzyme involved in DNA topology can improve productivity of L-amino acid other than L-histidine such as L-glutamine, L-glutamic acid and the like.

DOCUMENT LIST

Patent Documents patent document 1: JP-A-S55-148094
patent document 2: JP-A-H3-232497
patent document 3: JP-A-2002-300887
patent document 4: JP-A-2003-164297
patent document 5: JP-A-2001-157596

Non-Patent Documents non-patent document 1: FEMS Microbiology Letters, 201, 91 (2001)
non-patent document 2: FEMS Microbiology Letters, 173, 303 (1999)
non-patent document 3: Aminosan-hakko 195-215 (Japan Scientific Societies Press, 1986)
non-patent document 4: Proc. Natl. Acad. Sci. USA, 84, 517 (1987)
non-patent document 5: Molecular Microbiology, 14, 151 (1994)

SUMMARY OF THE INVENTION

Problems to be Solved by the Invention

An efficient process for producing L-glutamine or L-glutamic acid using a microorganism is provided.

Means of Solving the Problems

The present invention relates to the following (1)-(4).
(1) A process for producing L-glutamine or L-glutamic acid which comprises; culturing in a medium a microorganism which has an ability to produce L-glutamine or L-glutamic acid, and in which an ability to form a superhelical double-stranded DNA is decreased compared with that of the parent strain, producing and accumulating L-glutamine or L-glutamic acid in the medium, and recovering L-glutamine or L-glutamic acid from the medium.
(2) The process for producing L-glutamine or L-glutamic acid of (1), wherein the microorganism is the microorganism in which DNA gyrase activity is decreased compared with that of the parent strain.
(3) The process for producing L-glutamine or L-glutamic acid of (2), wherein the microorganism in which DNA gyrase activity is decreased compared with that of the parent strain is the microorganism in which an activity of a DNA gyrase inhibitory protein is increased compared with that of the parent strain.

(4) The process for producing L-glutamine or L-glutamic acid of (1), wherein the microorganism is the microorganism in which topoisomerase activity is increased compared with that of the parent strain.

Effect of the Invention

The present invention can provide an efficient production method of L-glutamine or L-glutamic acid using a microorganism.

DESCRIPTION OF EMBODIMENTS

1. Microorganism Used for the Process of the Present Invention

The microorganism which has an ability to produce L-glutamine or L-glutamic acid, and in which an ability to form a superhelical double-stranded DNA is decreased compared with that of the parent strain, which is used for the process of the present invention, refers to a microorganism showing a lower ratio of DNA having a superhelical structure relative to the DNAs present in the cells of the microorganism than that in the parent strain.

Specifically, (1) a microorganism in which DNA gyrase activity is decreased compared with that of the parent strain and (2) a microorganism in which DNA topoisomerase activity is decreased compared with that of the parent strain can be mentioned.

DNA gyrase activity in the present invention means an activity of DNA gyrase known as type II DNA topoisomerase, which introduces, in the presence of ATP, a negative superhelix into a positive superhelical DNA or relaxed DNA.

DNA topoisomerase activity in the present invention refers to an activity of type I or IV DNA topoisomerase, which removes superhelix of DNA.

DNA gyrase activity of a microorganism can be measured by the method of Ashiuchi et al. (The Journal of Biological Chemistry, 277 (42), 39070-39073, 2002). In addition, DNA gyrase activity and DNA topoisomerase activity can be measured by analyzing the ratio of superhelical DNA in the plasmid DNA in the cells of the microorganism according to the method of Mizushima et al. (Molecular Microbiology 23: 381-386, 1997).

Here, the parent strain in the present specification is a strain before decrease of the ability to form a superhelical double-stranded DNA, and may be a wild-type strain or a strain artificially bred from said wild-type strain, and the parent strain may or may not have an ability to produce L-glutamine or L-glutamic acid. The ability of the parent strain to generate L-glutamine or L-glutamic acid may be of its own or artificially imparted by the method mentioned below. When the parent strain does not have an ability to produce L-glutamine or L-glutamic acid, the microorganism to be used in the method of the present invention can be obtained by decreasing the ability of the parent strain to form a superhelical DNA, and artificially imparting an ability to produce L-glutamine or L-glutamic acid according to the method described below.

Examples of the parent strain include bacteria described by Neidhardt, F. C. et al. (*Escherichia coli* and *Salmonella*, Editor in Chief: F. C. Neidhardt, ASM Press, Washington D.C., 1996, (page 1201, Table 1). Preferable examples include bacteria belonging to the genera *Escherichia*, *Serratia*, *Bacillus*, *Brevibacterium*, *Corynebacterium*, *Pseudomonas*, *Streptomyces* and the like. More preferable examples of the bacterium include *Escherichia coli*, *Corynebacterium glutamicum*, *Corynebacterium ammoniagenes*, *Corynebacterium lactofermentum*, *Corynebacterium flavum*, *Corynebacterium efficiens*, *Bacillus subtilis*, *Bacillus megaterium*, *Serratia marcescens*, *Pseudomonas putida*, *Pseudomonas aeruginosa*, *Streptomyces coelicolor* and *Streptomyces lividans*, with particular preference given to *Escherichia coli* and *Corynebacterium glutamicum*.

Examples of the method of artificially imparting an ability to generate L-glutamine or L-glutamic acid to a microorganism include (a) a method of relaxing or deregulating at least one of the mechanisms controlling biosynthesis of L-glutamine or L-glutamic acid, (b) a method of enhancing expression of at least one of the enzymes involved in the biosynthesis of L-glutamine or L-glutamic acid, (c) a method of increasing the copy number of at least one of the enzyme genes involved in the biosynthesis of L-glutamine or L-glutamic acid, (d) a method of weakening or shutting off at least one of the metabolism pathways that are branched from the biosynthesis pathway of L-glutamine or L-glutamic acid to a metabolite other than said amino acid, and (e) a method of selecting a strain showing high resistance to an analogue of L-glutamine or L-glutamic acid, as compared to the wild-type strain, and the like. The above-mentioned known methods can be used alone or in combination.

As for the method of preparing a microorganism which has an ability to produce L-glutamine or L-glutamic acid by any of the above-mentioned (a)-(e) or a combined method thereof, many examples are described in Biotechnology 2nd ed., Vol. 6, Products of Primary Metabolism (VCH Verlagsgesellschaft mbH, Weinheim, 1996) section 14a, 14b, Advances in Biochemical Engineering/Biotechnology, 79, 1-35 (2003), Agric. Biol. Chem., 51, 2089-2094 (1987), and Aminosan-hakko, Japan Scientific Societies Press, Hiroshi Aida et al. (1986). Besides the above, there are a number of reports on a method of preparing a microorganism having an ability to produce a specific amino acid, such as JP-A-2003-164297, Agric. Biol. Chem., 39, 153-160 (1975), Agric. Biol. Chem., 39, 1149-1153 (1975), JP-A-S58-13599, J. Gen. Appl. Microbiol., 4, 272-283 (1958), JP-A-S63-94985, Agric. Biol. Chem., 37, 2013-2023 (1973), WO97/15673, JP-A-556-18596, JP-A-556-144092, JP-A-2003-511086, WO2006/001380 and the like. A microorganism having an ability to produce L-glutamine or L-glutamic acid can be prepared by referring to the above-mentioned documents and the like.

Examples of the microorganism which has an ability to produce L-glutamine or L-glutamic acid, which can be prepared by the above-mentioned method, include *Escherichia coli* JGLE1 and *Escherichia coli* JGLBE1 (WO2006/001379), *Corynebacterium glutamicum* ATCC13032 strain, GLA2 strain, GS2 strain, ATCC13032/pG1nA2 (WO2006/001380), FERM P-4806 and ATCC14751 strains and the like as L-glutamine producing bacteria, and FERM BP-5807 and ATCC13032 as L-glutamic acid producing bacteria.

The microorganism that can be used for the preparation of the above-mentioned microorganism which has an ability to produce L-glutamine or L-glutamic acid may be any as long as the above-mentioned methods (a)-(e) can be applied or it has the above-mentioned genetic trait. Preferred is the above-mentioned microorganism that can be used as the parent strain of the microorganism to be used in the process of the present invention.

(1) Microorganism in which DNA Gyrase Activity is Decreased Compared with that of Parent Strain The microorganism in which DNA gyrase activity is decreased compared with that of the parent strain refers to (A) a microorganism showing a decreased intracellular DNA gyrase activity as compared to the parent strain, due to the mutation in the inside or an expression regulatory region of a gene encoding DNA gyrase on chromosomal DNA, or (B) a microorganism in which intracellular DNA gyrase activity is decreased compared with that of the parent strain since the expression level of a protein having an activity to inhibit DNA gyrase (hereinafter DNA gyrase inhibitory protein) is increased due to the mutation in the inside or an expression regulatory region of a gene encoding the DNA gyrase inhibitory protein on chromosomal DNA, or transformation with a DNA encoding the DNA gyrase inhibitory protein.

The microorganism in which DNA gyrase activity is decreased compared with that of the parent strain in the present invention may be any as long as it shows lower DNA gyrase activity as compared to that of the parent strain. Preferably, it is a microorganism in which DNA gyrase activity is 20%, preferably 30%, more preferably 50% lower, than that of the parent strain.

In the present invention, DNA gyrase refers to a complex protein consisting of a protein comprising the amino acid sequence shown in SEQ ID NO: 44 (hereinafter to be also referred to as GyrA protein) and a protein comprising the amino acid sequence shown in SEQ ID NO: 46 (hereinafter to be also referred to as GyrB protein), or a complex protein consisting of respective homologous proteins of GyrA protein and GyrB protein.

As the homologous proteins of the amino acid sequences shown in SEQ ID NO: 44 and 46, for example, an amino acid sequence having 80% or more homology to any of the above amino acid sequences is, for example, an amino acid sequence having 80% or more, preferably 90% or more, more preferably 95% or more, more preferably 97% or more, particularly 98% or more or most preferably 99% or more homology, to the amino acid sequence shown in SEQ ID NO: 44 or 46 can be mentioned.

Homology of amino acid sequence can be determined using the algorithm BLAST of Karlin and Altschul [Pro. Natl. Acad. Sci. USA, 90, 5873 (1993)] or FASTA [Methods Enzymol., 183, 63 (1990)]. Based on this algorithm BLAST, programs called BLASTN and BLASTX have been developed [J. Mol. Biol., 215, 403 (1990)]. When amino acid sequences are analyzed with BLASTX on the basis of BLAST, parameters can be set to, for example, score=50 and wordlength=3. When the BLAST and Gapped BLAST programs are used, the default parameters of the respective programs can be used.

(A) A Microorganism in which Intracellular DNA Gyrase Activity is Decreased Compared with that of the Parent Strain, Due to the Mutation in the Inside or a Regulatory Region of a Gene Encoding DNA Gyrase on Chromosomal DNA In the present invention, the mutation in the inside or an expression regulatory region of a gene encoding DNA gyrase on chromosomal DNA includes a mutation that decreases the expression level of DNA gyrase and a mutation that decreases an activity per molecule of DNA gyrase.

As a DNA encoding DNA gyrase, for example, a DNA comprising the nucleotide sequence of the gyrA gene of *Escherichia coli* and comprising the nucleotide sequence identified by Entrez Gene ID NO: 946614, or a DNA comprising the nucleotide sequence of the gyrB gene of *Escherichia coli* and comprising the nucleotide sequence identified by Entrez Gene ID NO: 948211, and a DNA comprising the nucleotide sequence of a homologous gene to these genes can be mentioned.

As DNA comprising a nucleotide sequence of a homologous gene, a DNA having 80% or more, preferably 90% or more, more preferably 95% or more, more preferably 97% or more, particularly preferably 98% or more or most preferably 99% or more homology, to the nucleotide sequence shown in SEQ ID NO: 43 or 45 can be mentioned.

Homology of nucleotide sequence can be determined using the algorithm BLAST of Karlin and Altschul [Pro. Natl. Acad. Sci. USA, 90, 5873 (1993)] or FASTA [Methods Enzymol., 183, 63 (1990)]. When nucleotide sequences are analyzed with BLASTN on the basis of BLAST, parameters can be set to, for example, Score=100 and wordlength=12.

A DNA encoding DNA gyrase can be obtained from a parent strain by PCR method and the like, based on the known information of the nucleotide sequence of a DNA encoding DNA gyrase.

A microorganism in which DNA gyrase activity is decreased compared with that of the parent strain can be obtained, for example, as a microorganism having resistance to DNA gyrase inhibitors.

The microorganism having resistance to DNA gyrase inhibitors can be obtained by performing spontaneous mutagenesis, or a general mutation treatment by UV irradiation, or with a mutation-inducing agent such as N-methyl-N'-nitro-N-nitrosoguanidine (NTG) and the like, culturing the mutant strain under normal conditions on an agar plate medium containing a DNA gyrase inhibitor at a concentration at which the parent strain cannot grow or insufficiently grows, and selecting, from the resulting colonies, a strain showing faster growth than the parent strain or forming a larger colony, as a strain having resistance to DNA gyrase inhibitors.

A DNA gyrase inhibitor that can be used for the preparation of such microorganism showing decreased DNA gyrase activity may be any as long as it is a substance capable of inhibiting DNA gyrase and, for example, nalidixic acid, oxolinic acid, coumermycin, novobiocin or alkali metal salts thereof and the like are used. As the DNA gyrase inhibitor, nalidixic acid can be preferably used.

As a DNA gyrase inhibitor-resistant strain, a microorganism capable of growing on a medium containing 5 mg/L nalidixic acid can be preferably used, which microorganism is, for example, *Escherichia coli*.

Examples of the microorganism that can be used in the process of the present invention, which can be obtained as a DNA gyrase inhibitor-resistant strain, include *Escherichia coli* NAR01 strain, NAR02 and NAR03 strains, and *Corynebacterium glutamicum* GNA1 strain and GNA2 strain, which are nalidixic acid-resistant strains.

In addition, a microorganism in which DNA gyrase activity is decreased compared with that of the parent strain can also be obtained by artificially and site-specifically introducing a mutation, which decreases the activity of DNA gyrase, into the inside or an expression regulatory region of a gene encoding the DNA gyrase of the parent strain.

As such mutation to be introduced into an expression regulatory region of a gene encoding DNA gyrase, substitution of a promoter of the gene with one having lower efficiency and the like can be mentioned.

The site-specific mutation can be introduced into the inside or an expression regulatory region of a gene encoding DNA gyrase by preparing a DNA fragment introduced with an object mutation in the inside or an expression regulatory region of a gene encoding DNA gyrase, by a known method, and then substituting the object region on the chromosomal DNA of the parent strain with the fragment.

As a method for introducing a site-specific mutation, the methods described in Molecular Cloning, A Laboratory Manual, Second Edition, Cold Spring Harbor Laboratory Press (1989) (hereinafter to be abbreviated as Molecular Cloning, 2nd edition), Current Protocols in Molecular Biology, John Wiley & Sons (1987-1997) (hereinafter to be abbreviated as Current Protocols in Molecular Biology), Nucleic Acids Research, 10, 6487 (1982), Proc. Natl. Acad. Sci. USA, 79, 6409 (1982), Gene, 34, 315 (1985), Nucleic Acids Research, 13, 4431 (1985), Proc. Natl. Acad. Sci. USA, 82, 488 (1985) and the like can be mentioned.

Examples of the method for introducing a mutated DNA fragment into the parent strain include a method using phage-derived λ Red recombinase [Proc. Natl. Acad. Sci. USA, 97, 6640 (2000), Mol. Microbiol., 55, 137 (2005), Biosci. Biotechnol. Biochem., 71, 2905 (2007)].

Furthermore, a strain wherein a DNA on the chromosome of a parent strain is substituted by a mutant DNA can be obtained by a selection method which utilizes *Escherichia coli* that has become sucrose sensitive due to *Bacillus subtilis* levansucrase introduced on the chromosome together with a mutant DNA, or a selection method which utilizes *Escherichia coli* that has become streptomycin sensitive due to a wild-type rpsL gene introduced into *Escherichia coli* having a streptomycin resistant mutated rpsL gene [Mol. Microbiol., 55, 137 (2005), Biosci. Biotechnol. Biochem., 71, 2905 (2007)] and the like.

In addition to the above-mentioned methods, other gene substitution methods can also be used as long as they can substitute a gene on the chromosome of a microorganism.

Examples of the microorganism usable for the process of the present invention, which can be obtained by introducing a site-specific mutation into the inside of a gene encoding the DNA gyrase of the parent strain include *Escherichia coli* GYR1 strain and GYR2 strain, which are mutant strains of gyrA gene, and *Escherichia coli* GYR3 strain, which is a mutant strain of gyrB gene.

(B) A Microorganism in which Intracellular DNA Gyrase Activity is Decreased Compared with that of the Parent Strain Since the Activity of a DNA Gyrase Inhibitory Protein is Increased than that of the Parent Strain Due to the Mutation in the Inside or a Regulatory Region of a Gene Encoding the DNA Gyrase Inhibitory Protein on the Chromosomal DNA, or Transformation with a DNA Encoding the DNA Gyrase Inhibitory Protein As a microorganism in which the intracellular DNA gyrase activity is decreased compared with that of the parent strain used in the present invention, a microorganism in which DNA gyrase activity is decreased compared with that of the parent strain due to (I) introduction of a mutation in the inside or a regulatory region of a gene encoding the DNA gyrase inhibitory protein on chromosomal DNA of the parent strain, or (II) transformation of the parent strain with a DNA encoding a DNA gyrase inhibitory protein can also be used.

As a DNA gyrase inhibitory protein, a protein consisting of the amino acid sequence shown in SEQ ID NO: 20 and a homologous protein thereof can be mentioned. As the homologous protein, a protein having a DNA gyrase inhibitory activity and consisting of an amino acid sequence having 80% or more, preferably 90% or more, more preferably 95% or more, still more preferably 98% or more, or most preferably 99% or more homology, to the amino acid sequence shown in SEQ ID NO: 20, can be mentioned.

Amino acid sequence and nucleotide sequence homologies can be determined using the algorithm BLAST of Karlin and Altschul [Pro. Natl. Acad. Sci. USA, 90, 5873 (1993)] or FASTA [Methods Enzymol., 183, 63 (1990)]. Based on this algorithm BLAST, programs called BLASTN and BLASTX have been developed [J. Mol. Biol., 215, 403 (1990)]. When nucleotide sequences are analyzed with BLASTN on the basis of BLAST, parameters are set to, for example, Score=100 and wordlength=12. When amino acid sequences are analyzed with BLASTX on the basis of BLAST, parameters are set to, for example, score=50 and wordlength=3. When the BLAST and Gapped BLAST programs are used, the default parameters of the respective programs are used. The specific ways of these analytical methods are well known.

The DNA gyrase inhibitory activity can be determined by, for example, measuring DNA gyrase activity of a microorganism that strongly expresses DNA gyrase inhibitory protein, by the method of Mizushima et al.

(I) Microorganism in which DNA Gyrase Activity is Decreased Compared with that of the Parent Strain Obtained by Modifying DNA Encoding DNA Gyrase Inhibitory Protein on the Chromosomal DNA of the Parent Strain As a DNA encoding a DNA gyrase inhibitory protein, for example, a DNA comprising the nucleotide sequence of murI gene, which has the nucleotide sequence identified by Entrez Gene ID NO: 948467, and a DNA comprising the nucleotide sequence of a homologous gene thereof can be recited. As the DNA comprising the nucleotide sequence of murI gene, a DNA comprising the nucleotide sequence shown in SEQ ID NO: 19 can be recited.

As the DNA encoding a homologous gene, a DNA having 90% or more, preferably 95% or more, more preferably 97% or more, still more preferably 98% or more, or particularly preferably 99% or more homology, to the nucleotide sequence shown in SEQ ID NO: 19, can be mentioned.

Homology of nucleotide sequence can be determined using the algorithm BLAST of Karlin and Altschul [Pro. Natl. Acad. Sci. USA, 90, 5873 (1993)] or FASTA [Methods Enzymol., 183, 63 (1990)]. When nucleotide sequences are analyzed with BLASTN on the basis of BLAST, parameters can be set to, for example, Score=100 and wordlength=12.

A DNA encoding a DNA gyrase inhibitory protein can be obtained from the parent strain by PCR method and the like, based on the known information of the nucleotide sequence of a DNA encoding a DNA gyrase inhibitory protein.

As a microorganism in which specific activity of a DNA gyrase inhibitory protein is increased compared with that of the parent strain, which is obtained by modification of a DNA encoding the protein on the chromosomal DNA of the parent strain, a microorganism having a mutant protein with improved activity as compared to the DNA gyrase inhibitory protein of the parent strain, since it has a protein comprising an amino acid sequence wherein one or more amino acids, preferably 1-10 amino acids, more preferably 1-5 amino acids, still more preferably 1-3 amino acids, in the amino acid sequence of the protein that the parent strain has, are substituted, can be mentioned.

As a microorganism in which the production amount of a DNA gyrase inhibitory protein is increased compared with that of the parent strain, which is obtained by modification of a DNA encoding the protein on the chromosomal DNA of the parent strain, a microorganism in which the production amount of the DNA gyrase inhibitory protein is increased compared with that of the parent strain, since it has a promoter region wherein one or more nucleotides, preferably 1-10 nucleotides, more preferably 1-5 nucleotides, still more preferably 1-3 nucleotides, in the nucleotide sequence in a transcription regulatory region or a promoter region of a gene encoding the protein on the chromosomal DNA of the parent strain, are substituted, can be mentioned.

Of the microorganisms in which the activity of a DNA gyrase inhibitory protein is increased compared with that of the parent strain, a microorganism in which the specific activity of a DNA gyrase inhibitory protein is increased compared with that of the parent strain can be obtained by subjecting a DNA encoding a DNA gyrase inhibitory protein to an in vitro mutation treatment using a mutating agent, or error-prone PCR and the like to introduce a mutation into the DNA, replacing a DNA encoding a DNA gyrase inhibitory protein before introducing mutation, which is on the chromosomal DNA of the parent strain, with the mutated DNA, by a known method [Proc. Natl. Acad. Sci. USA., 97, 6640 (2000)] to prepare a variant that expresses the mutated DNA, and comparing DNA gyrase activity between the parent strain and the variant by the above-mentioned method.

Moreover, of the microorganisms in which an activity of a DNA gyrase inhibitory protein is increased compared with that of the parent strain, a microorganism in which the production amount of the protein is increased compared with that of the parent strain can be confirmed by a method including subjecting a DNA comprising the nucleotide sequence of a transcription regulatory region or a promoter region of a gene encoding the DNA gyrase inhibitory protein that the parent strain has, for example, 200 bp, preferably 100 bp, on the upstream side of the initiation codon of the gene, to an in vitro mutation treatment or error-prone PCR and the like to introduce a mutation into the DNA, replacing a transcription regulatory region or a promoter region of a gene encoding a DNA gyrase inhibitory protein before mutation introduction, which is on the chromosomal DNA of the parent strain, with the mutated DNA by a known method [Proc. Natl. Acad. Sci. USA., 97, 6640 (2000)] to prepare a variant having a mutated transcription regulatory region or promoter region, and comparing, by RT-PCR or Northern hybridization and the like, the transcription amounts of the gene encoding the DNA gyrase inhibitory protein of the parent strain and the variant, or a method including comparison of the production amount of the DNA gyrase inhibitory protein of the parent strain and the variant by SDS-PAGE and the like.

In addition, a microorganism in which the production amount of a DNA gyrase inhibitory protein is increased compared with that of the parent strain can also be obtained by replacing a promoter region of a gene encoding the DNA gyrase inhibitory protein of the parent strain with a known strong promoter sequence.

As such promoter, promoters derived from *Escherichia coli*, phage and the like, such as trp promoter ($P_{trp}$), lac promoter ($P_{lac}$) $P_L$ promoter, $P_R$ promoter, $P_{SE}$ promoter and the like, SPO1 promoter, SPO2 promoter, penP promoter and the like, functionable in *E. coli*. In addition, artificially created promoters such as promoter having two $P_{trp}$ connected in series, tac promoter, lacT7 promoter, let I promoter and the like can also be recited.

Moreover, xylA promoter [Appl. Microbiol. Biotechnol., 35, 594-599 (1991)] for expression in a microorganism belonging to the genus *Bacillus*, P54-6 promoter [Appl. Microbiol. Biotechnol., 53, 674-679 (2000)] for expression in a microorganism belonging to the genus *Corynebacterium* and the like can also be used.

A DNA encoding a DNA gyrase inhibitory protein can be obtained, for example, by subjecting the chromosomal DNA library of a microorganism such as *E. coli* and the like to Southern hybridization using a probe DNA that can be designed based on the nucleotide sequence of a DNA encoding a protein having the amino acid sequence shown in SEQ ID NO: 20, or PCR using a primer DNA that can be designed based on the nucleotide sequence, and a chromosomal DNA of a microorganism, preferably *E. coli*, as a template [PCR Protocols, Academic Press (1990)].

Alternatively, a sequence having 80% or more, preferably 90% or more, more preferably 95% or more, still more preferably 97% or more, particularly preferably 98% or more, or most preferably 99% or more homology, to the nucleotide sequence of a DNA encoding a protein comprising the amino acid sequence shown in SEQ ID NO: 20, is searched in various gene sequence databases, and a DNA encoding a DNA gyrase inhibitory protein can also be obtained from a chromosomal DNA, cDNA library etc. of the microorganism having the nucleotide sequence, by the above-mentioned method and based on the nucleotide sequence obtained by the search.

The nucleotide sequence of the DNA can be determined by incorporating the obtained DNA as it is or after digestion with a suitable restriction enzyme and the like into a vector by a conventional method, introducing the obtained recombinant DNA into a host cell, and analyzing the nucleotide sequence by a nucleotide sequence analysis method generally used, for example, a dideoxy method [Proc. Natl. Acad. Sci., USA, 74, 5463 (1977)] or by using a nucleotide sequence analyzer such as 3700 DNA analyzer (manufactured by Applied Biosystems) and the like.

As the above-mentioned vector, pBluescript II KS(+) (manufactured by Stratagene), pDIRECT [Nucleic Acids Res., 18, 6069 (1990)], pCR-Script Amp SK(+) (manufactured by Stratagene), pT7Blue (manufactured by Novagen), pCR II (manufactured by Invitrogen), pCR-TRAP (manufactured by GenHunter) and the like can be mentioned.

As the host cell, microorganisms belonging to the genus *Escherichia* and the like can be mentioned. Examples of the microorganisms belonging to the genus *Escherichia* include *E. coli* XL1-Blue, *E. coli* XL2-Blue, *E. coli* DH1, *E. coli* MC1000, *E. coli* ATCC 12435, *E. coli* W1485, *E. coli* JM109, *E. coli* HB101, *E. coli* No. 49, *E. coli* W3110, *E. coli* NY49, *E. coli* MP347, *E. coli* NM522, *E. coli* BL21, *E. coli* ME8415 and the like.

As a method for introduction of recombinant DNA, any method can be used as long as it can introduce DNA into the above-mentioned host cell, and examples thereof include a method using a calcium ion [Proc. Natl. Acad. Sci., USA, 69, 2110 (1972)], a protoplast method (JP-A-S63-248394), an electroporation method [Nucleic Acids Res., 16, 6127 (1988)] and the like.

As a result of the determination of the nucleotide sequence, when the obtained DNA is a partial length, full-length DNA can be obtained by subjecting the chromosomal DNA library to a Southern hybridization method using the partial length DNA as a probe and the like.

Furthermore, the object DNA can also be prepared by chemical synthesis based on the determined nucleotide sequence of the DNA and using a 8905 type DNA synthesizer manufactured by Perceptive Biosystems and the like.

As the DNA obtained as mentioned above, for example, a DNA encoding a protein comprising the amino acid sequence shown in SEQ ID NO: 20, and a DNA comprising the nucleotide sequence shown in SEQ ID NO: 19 can be mentioned.

(II) Microorganism Obtained by Transformation with DNA Encoding DNA Gyrase Inhibitory Protein As a microorganism obtained by transforming the parent strain with a DNA encoding a DNA gyrase inhibitory protein, a microorganism obtained by transforming the parent strain with:

[1] a protein comprising the amino acid sequence shown in SEQ ID NO: 20 or a homologous protein thereof, and
[2] a DNA comprising the nucleotide sequence shown in SEQ ID NO: 19 or a DNA comprising the nucleotide sequence of a homologous gene of murI gene;
can be mentioned.

As the microorganism, (i) a microorganism having an exogenous DNA encoding a DNA gyrase inhibitory protein on a chromosomal DNA, and (ii) a microorganism having an exogenous DNA encoding a DNA gyrase inhibitory protein extrachromosomally. That is, when the parent strain does not have a DNA encoding a DNA gyrase inhibitory protein, the microorganism of (i) is a microorganism having one or more of newly-introduced such DNAs on the chromosomal DNA and, when the parent strain intrinsically has a DNA encoding a DNA gyrase inhibitory protein, it is a microorganism having two or more DNAs encoding DNA gyrase inhibitory proteins including newly-introduced such DNA on the chromosomal DNA. The microorganism of (ii) is a microorganism having a DNA encoding a DNA gyrase inhibitory protein on the plasmid DNA.

The microorganism can be prepared as follows. Based on a DNA encoding a DNA gyrase inhibitory protein, a DNA fragment with a suitable length, which contains a region encoding a DNA gyrase inhibitory protein, is prepared as necessary. By substituting the nucleotide(s) in the nucleotide sequence of the region encoding a DNA gyrase inhibitory protein to provide a codon optimal for the expression in a host cell, a DNA fragment with good transcription efficiency can be prepared.

A recombinant DNA is prepared by inserting the DNA fragment into the downstream of the promoter of a suitable expression vector.

By introducing the recombinant DNA into a host cell compatible with the expression vector, a transformant showing an improved activity of a DNA gyrase inhibitory protein than the host cell, i.e., parent strain, can be obtained.

As the expression vector, a vector which is autonomously replicable or can be incorporated into a chromosome in the above-mentioned host cell, and contains a promoter at a site permitting transcription of a DNA encoding a DNA gyrase inhibitory protein, is used.

When prokaryote is used as a host cell, a recombinant DNA containing a DNA encoding a DNA gyrase inhibitory protein is preferably autonomously replicable in the prokaryote as well as a recombinant DNA consisting of promoter, ribosome binding sequence, DNA encoding DNA gyrase inhibitory protein, and transcription terminator sequence. It may contain a gene controlling the promoter.

As an expression vector, pColdI (manufactured by Takara Bio), pCDF-1b, pRSF-1b (all manufactured by Novagen), pMAL-c2x (manufactured by New England Biolabs), pGEX-4T-1 (manufactured by GE Healthcare Bio-Sciences), pTrcHis (manufactured by Invitrogen), pSE280 (manufactured by Invitrogen), pGEMEX-1 (manufactured by Promega), pQE-30 (manufactured by QIAGEN), pET-3 (manufactured by Novagen), pKYP10 (JP-A-S58-110600), pKYP200 [Agric. Biol. Chem., 48, 669 (1984)], pLSA1 [Agric. Biol. Chem., 53, 277 (1989)], pGEL1 [Proc. Natl. Acad. Sci., USA, 82, 4306 (1985)], pBluescript II SK(+), pBluescript II KS(−) (manufactured by Stratagene), pTrS30 [prepared from *Escherichia coli* JM109/pTrS30 (FERM BP-5407)], pTrS32 [prepared from *Escherichia coli* JM109/pTrS32 (FERM BP-5408)], pPAC31 (WO98/12343), pUC19 [Gene, 33, 103 (1985)], pSTV28 (manufactured by Takara Bio), pUC118 (manufactured by Takara Bio), pPA1 (JP-A-S63-233798) and the like can be mentioned.

The promoter may be any as long as it can function in a host cell such as *E. coli* and the like. For example, promoters derived from *E. coli*, phage and the like, such as trp promoter ($P_{trp}$), lac promoter ($P_{lac}$), $P_L$ promoter, $P_R$ promoter, $P_{SE}$ promoter and the like, SPO1 promoter, SPO2 promoter, penP promoter and the like. In addition, artificially designed/modified promoters such as promoter having two $P_{trp}$ connected in series, tac promoter, lacT7 promoter, let I promoter and the like can also be used.

Furthermore, xylA promoter [Appl. Microbiol. Biotechnol., 35, 594-599 (1991)] for expression in a microorganism belonging to the genus *Bacillus*, P54-6 promoter [Appl. Microbiol. Biotechnol., 53, 674-679 (2000)] for expression in a microorganism belonging to the genus *Corynebacterium* and the like can also be used.

A plasmid wherein the distance between Shine-Dalgarno sequence which is a ribosome binding sequence, and an initiation codon is adjusted to a suitable distance (for example, 6-18 bases) is preferably used.

While a recombinant DNA, wherein a DNA encoding a DNA gyrase inhibitory protein is bound to an expression vector, does not necessarily require a transcription terminator sequence, a transcription terminator sequence is preferably disposed immediately downstream of a structural gene.

Examples of such recombinant DNA include plasmid pSMurI.

As a host of the recombinant DNA, the parent strain of the microorganism used in the present invention can be used.

As the microorganism obtained by transformation with a DNA encoding a DNA gyrase inhibitory protein, which can be used in the process of the present invention, *Escherichia coli* JP/pTyeiG/pSMurI can be mentioned.

(2) Microorganism in which DNA Topoisomerase Activity is Decreased Compared with that of the Parent Strain As a microorganism in which DNA topoisomerase activity is increased compared with that of the parent strain in the present invention, (A) (I) a microorganism in which specific activity of type I or IV DNA topoisomerase is increased compared with that of the parent strain, and (II) a microorganism in which the production amount of type I or IV DNA topoisomerase is increased compared with that of the parent strain, which are obtained by modifying a DNA encoding the enzyme on the chromosomal DNA of the parent strain, and (B) a microorganism obtained by transforming the parent strain with a DNA encoding type I or IV DNA topoisomerase can be mentioned.

As a type I or IV DNA topoisomerase, a protein described in the following [3] or [4]:
[3] a protein comprising the amino acid sequence shown in any of SEQ ID NOs: 24, 36 and 40, or a homologous protein thereof, and
[4] a complex protein consisting of a protein comprising the amino acid sequence shown in SEQ ID NO: 28 and a protein comprising the amino acid sequence shown in SEQ ID NO: 32 or a complex protein consisting of homologous proteins thereof; can be mentioned.

The homologous protein is, for example, a protein consisting of the amino acid sequence having 80% or more, preferably 90% or more, more preferably 95% or more, still more preferably 97% or more, particularly preferably 98% or more, most preferably 99% or more homology, to the amino acid sequence shown in any of SEQ ID NOs: 24, 28, 32, 36 and 40, which has DNA topoisomerase activity.

Homology of an amino acid sequence and a nucleotide sequence can be determined using the algorithm BLAST of Karlin and Altschul [Pro. Natl. Acad. Sci. USA, 90, 5873 (1993)] or FASTA [Methods Enzymol., 183, 63 (1990)].

Based on this algorithm BLAST, programs called BLASTN and BLASTX have been developed [J. Mol. Biol., 215, 403 (1990)]. When nucleotide sequences are analyzed with BLASTN on the basis of BLAST, parameters are set to, for example, Score=100 and wordlength=12. When amino acid sequences are analyzed with BLASTX on the basis of BLAST, parameters are set to, for example, score=50 and wordlength=3. When the BLAST and Gapped BLAST programs are used, the default parameters of the respective programs are used. The specific ways of these analytical methods are well known.

DNA topoisomerase activity can be determined by, for example, transforming a microorganism with a DNA encoding the protein, and measuring DNA topoisomerase activity of the transformant by the method of Mizushima et al.

(A) Microorganism in which DNA Topoisomerase Activity is Increased Compared with that of the Parent Strain, which is Obtained by Modifying DNA Encoding Type I or IV DNA Topoisomerase on the Chromosomal DNA of the Parent Strain As a DNA encoding DNA topoisomerase, for example, a DNA comprising the nucleotide sequence of topA gene of *Escherichia coli*, which has the nucleotide sequence identified by Entrez Gene ID NO: 945862, a DNA comprising the nucleotide sequence of parCE gene of *Escherichia coli*, which has the nucleotide sequence identified by Entrez Gene ID NOs: 947499 and 947501, a DNA comprising the nucleotide sequence identified by NCBI Accession No. NCgl0304 of *Corynebacterium glutamicum*, which has the nucleotide sequence identified by Entrez Gene ID NO: 1021373 or a DNA comprising the nucleotide sequence identified by NCBI Accession No. NCgl1769, which has the nucleotide sequence identified by Entrez Gene ID NO: 1019801 and DNAs comprising the nucleotide sequences of homologous genes thereof can be mentioned.

As a DNA comprising the nucleotide sequence of the above-mentioned gene, a DNA comprising the nucleotide sequence shown by any of SEQ ID NOs: 23, 27, 31, 35 and 39 can be mentioned.

As the DNA comprising the nucleotide sequence of a homologous gene, for example, a DNA having 90% or more, preferably 95% or more, more preferably 97% or more, still more preferably 98% or more, particularly preferably 99% or more homology, to a DNA consisting of the nucleotide sequence shown by any of SEQ ID NOs: 23, 27, 31, 35 and 39, when calculated using the above-mentioned BLAST, FASTA and the like and based on the above-mentioned parameters and the like, can be mentioned.

Homology of a nucleotide sequence can be determined using the algorithm BLAST of Karlin and Altschul [Pro. Natl. Acad. Sci. USA, 90, 5873 (1993)] or FASTA [Methods Enzymol., 183, 63 (1990)]. When nucleotide sequences are analyzed with BLASTN on the basis of BLAST, parameters are set to, for example, Score=100 and wordlength=12.

A DNA encoding DNA topoisomerase can be obtained from the parent strain by PCR method and the like, based on the known information of the nucleotide sequence of a DNA encoding DNA topoisomerase.

Examples of the method of introducing substitution, deletion or addition of one or more bases into a DNA encoding a DNA topoisomerase include methods according to the site-specific mutation introduction method described in Molecular Cloning, 3rd edition, Current Protocols in Molecular Biology, etc.

As a microorganism in which the specific activity of a protein having DNA topoisomerase activity is increased compared with that of the parent strain, which is obtained by alteration of a DNA encoding the protein on the chromosomal DNA of the parent strain, a microorganism having a mutant protein with improved DNA topoisomerase activity as compared to the protein having a DNA topoisomerase activity of the parent strain, since it has a protein having an amino acid sequence wherein one or more amino acids, preferably 1-10 amino acids, more preferably 1-5 amino acids, still more preferably 1-3 amino acids, in the amino acid sequence of the protein that the parent strain has, are substituted, can be mentioned.

A microorganism in which a specific activity of a protein having DNA topoisomerase activity is increased compared with that of the protein having DNA topoisomerase activity of the parent strain can be obtained by subjecting a DNA encoding a protein having DNA topoisomerase activity to an in vitro mutation treatment using a mutating agent, or error-prone PCR and the like to introduce a mutation into the DNA, replacing a DNA encoding a protein having DNA topoisomerase activity before mutation introduction, which is on the chromosomal DNA of the parent strain, with the mutated DNA by a known method [Proc. Natl. Acad. Sci. USA., 97, 6640 (2000)] to prepare a variant that expresses the mutated DNA, and comparing DNA topoisomerase activity between the parent strain and the variant by the above-mentioned method.

In the above-mentioned (A), (II), as a microorganism in which the production amount of a protein having DNA topoisomerase activity is increased compared with that of the parent strain, which is obtained by modification of a DNA encoding the protein on the chromosomal DNA of the parent strain, a microorganism in which the production amount of the protein is increased compared with that of the protein having DNA topoisomerase activity of the parent strain, since it has a promoter region wherein one or more nucleotides, preferably 1-10 nucleotides, more preferably 1-5 nucleotides, still more preferably 1-3 nucleotides, in the nucleotide sequence in a transcription regulatory region or a promoter region of a gene encoding the protein on the chromosomal DNA of the parent strain, are substituted, can be mentioned.

Moreover, a microorganism in which the production amount of the protein having DNA topoisomerase activity is increased compared with that of the parent strain can be confirmed by a method including subjecting a DNA having a nucleotide sequence of a transcription regulatory region and a promoter region of a gene encoding the protein having DNA topoisomerase activity that the parent strain has, for example, 200 bp, preferably 100 bp, on the upstream side of the initiation codon of the protein, to an in vitro mutation treatment or error-prone PCR and the like to introduce a mutation into the DNA, replacing a transcription regulatory region and a promoter region of a gene encoding a protein having DNA topoisomerase activity before introducing mutation, which is on the chromosomal DNA of the parent strain, with the mutated DNA by a known method [Proc. Natl. Acad. Sci. USA., 97, 6640 (2000)] to prepare a variant having a mutated transcription regulatory region or promoter region, and comparing, by RT-PCR or Northern hybridization and the like, the transcription amounts of the gene encoding the protein having DNA topoisomerase activity of the parent strain and the variant, or a method including comparison of the production levels of the protein having DNA topoisomerase activity of the parent strain and the variant by SDS-PAGE and the like.

In addition, a microorganism in which the production amount of a protein having DNA topoisomerase activity is increased compared with that of the parent strain can also be obtained by replacing a promoter region of a gene encoding the protein having DNA topoisomerase activity of the parent strain with a known strong promoter sequence.

As such promoter, promoters derived from *Escherichia coli*, phage and the like, such as trp promoter ($P_{trp}$), lac promoter ($P_{lac}$), $P_L$ promoter, $P_R$ promoter, $P_{SE}$ promoter and the like, SPO1 promoter, SPO2 promoter, penP promoter and the like, functionable in *E. coli*. In addition, artificially created promoters such as promoter having two $P_{trp}$ connected in series, tac promoter, lacT7 promoter, let I promoter and the like can also be recited.

Moreover, xylA promoter [Appl. Microbiol. Biotechnol., 35, 594-599 (1991)] for expression in a microorganism belonging to the genus *Bacillus*, P54-6 promoter [Appl. Microbiol. Biotechnol., 53, 674-679 (2000)] for expression in a microorganism belonging to the genus *Corynebacterium* and the like can also be used.

A DNA encoding a protein having DNA topoisomerase activity can be obtained, for example, by subjecting the chromosomal DNA library of a microorganism such as *E. coli* and the like to Southern hybridization using a probe DNA that can be designed based on the nucleotide sequence of a DNA encoding a protein comprising the amino acid sequence shown in any of SEQ ID NOs: 24, 28, 32, 36 and 40, or PCR using a primer DNA that can be designed based on the nucleotide sequence, and a chromosomal DNA of a microorganism, preferably. *E. coli*, as a template [PCR Protocols, Academic Press (1990)].

Alternatively, a sequence having 80% or more, preferably 90% or more, more preferably 95% or more, still more preferably 97% or more, particularly preferably 98% or more, or most preferably 99% or more homology, to the nucleotide sequence of a DNA encoding a protein comprising the amino acid sequence shown in any of SEQ ID NOs: 24, 28, 32, 36 and 40, is searched in various gene sequence databases, and a DNA encoding a protein having DNA topoisomerase activity can also be obtained from a chromosomal DNA, cDNA library etc. of the microorganism having the nucleotide sequence, by the above-mentioned method and based on the nucleotide sequence obtained by the search.

The nucleotide sequence of the DNA can be determined by incorporating the obtained DNA as it is or after digestion with a suitable restriction enzyme and the like into a vector by a conventional method, introducing the obtained recombinant DNA into a host cell, and analyzing the nucleotide sequence by a nucleotide sequence analysis method generally used, for example, a dideoxy method [Proc. Natl. Acad. Sci., USA, 74, 5463 (1977)] or by using a nucleotide sequence analyzer such as 3700 DNA analyzer (manufactured by Applied Biosystems) and the like.

As the above-mentioned vector, pBluescript II KS(+) (manufactured by Stratagene), pDIRECT [Nucleic Acids Res., 18, 6069 (1990)], pCR-Script Amp SK(+) (manufactured by Stratagene), pT7Blue (manufactured by Novagen), pCR II (manufactured by Invitrogen), pCR-TRAP (manufactured by GenHunter) and the like can be mentioned.

As the host cell, microorganisms belonging to the genus *Escherichia* and the like can be mentioned. Examples of the microorganisms belonging to the genus *Escherichia* include *E. coli* XL1-Blue, *E. coli* XL2-Blue, *E. coli* DH1, *E. coli* MC1000, *E. coli* ATCC 12435, *E. coli* W1485, *E. coli* JM109, *E. coli* HB101, *E. coli* No. 49, *E. coli* W3110, *E. coli* NY49, *E. coli* MP347, *E. coli* NM522, *E. coli* BL21, *E. coli* ME8415 and the like.

As a method for introduction of recombinant DNA, any method can be used as long as it can introduce DNA into the above-mentioned host cell, and examples thereof include a method using a calcium ion [Proc. Natl. Acad. Sci., USA, 69, 2110 (1972)], a protoplast method (JP-A-S63-248394), an electroporation method [Nucleic Acids Res., 16, 6127 (1988)] and the like.

As a result of the determination of the nucleotide sequence, when the obtained DNA is a partial length, full-length DNA can be obtained by subjecting the chromosomal DNA library to a Southern hybridization method using the partial length DNA as a probe and the like.

Furthermore, the object DNA can also be prepared by chemical synthesis based on the determined nucleotide sequence of the DNA and using a 8905 type DNA synthesizer manufactured by Perceptive Biosystems and the like.

As the DNA obtained as mentioned above, for example, a DNA encoding a protein comprising the amino acid sequence shown in any of SEQ ID NOs: 24, 28, 32, 36 and 40, and a DNA comprising the nucleotide sequence shown in any of SEQ ID NOs: 23, 27, 31, 35 and 39 can be mentioned.

(B) Microorganism Obtained by Transformation with DNA Encoding Type I or IV DNA Topoisomerase As a microorganism obtained by transforming the parent strain with a DNA encoding a protein having DNA topoisomerase activity, a microorganism obtained by transforming the parent strain with:

[5] a DNA encoding the protein of any of the above-mentioned [3] and [4];

[6] a DNA comprising the nucleotide sequence shown in any of SEQ ID NOs: 23, 35 and 39, or a DNA comprising the nucleotide sequence of a homologous gene of topA gene, NCgl0304 or NCgl1769;

[7] a DNA having the nucleotide sequence shown in SEQ ID NO: 27, a DNA having the nucleotide sequence shown in SEQ ID NO: 31 or a DNA having the nucleotide sequence of a homologous gene of parCE gene; can be mentioned.

As the microorganism, (i) a microorganism having an exogenous DNA encoding a protein having DNA topoisomerase activity on a chromosomal DNA, and (ii) a microorganism having an exogenous DNA encoding a protein having DNA topoisomerase activity extrachromosomally. That is, when the parent strain does not have a DNA encoding a protein having DNA topoisomerase activity, the microorganism of (i) is a microorganism having one or more of newly-introduced such DNAs on the chromosomal DNA and, when the parent strain intrinsically has a DNA encoding a protein having DNA topoisomerase activity, it is a microorganism having two or more DNAs encoding proteins having DNA topoisomerase activity including newly-introduced such DNA on the chromosomal DNA. The microorganism of (ii) is a microorganism having a DNA encoding a protein having DNA topoisomerase activity on the plasmid DNA.

As the DNA comprising the nucleotide sequence of a homologous gene, for example, a DNA having than 90% or more, preferably 95% or more, more preferably 97% or more, still more preferably 98% or more, particularly preferably 99% or more homology, to a DNA consisting of the nucleotide sequence shown in any of SEQ ID NOs: 23, 27, 31, 35 and 39, when calculated using the above-mentioned BLAST, FASTA and the like and based on the above-mentioned parameters and the like, can be mentioned.

A microorganism transformed with a DNA encoding DNA topoisomerase can be prepared as follows.

Based on a DNA encoding a protein having DNA topoisomerase activity, a DNA fragment with a suitable length, which contains a region encoding a protein having DNA topoisomerase activity, is prepared as necessary. By substituting the base(s) in the nucleotide sequence of the region encoding a protein having DNA topoisomerase activity to provide a codon optimal for the expression in a host cell, a DNA fragment with good transcription efficiency can be prepared.

A recombinant DNA is prepared by inserting the DNA fragment into the downstream of the promoter of a suitable expression vector.

By introducing the recombinant DNA into a host cell compatible with the expression vector, a transformant showing an improved activity of a protein having a DNA topoisomerase activity than the host cell, i.e., parent strain, can be obtained.

As the expression vector, a vector which is autonomously replicable or can be incorporated into a chromosome in the above-mentioned host cell, and contains a promoter at a site permitting transcription of a DNA encoding a protein having DNA topoisomerase activity, is used.

When prokaryote is used as a host cell, a recombinant DNA containing a DNA encoding a protein having DNA topoisomerase activity is preferably autonomously replicable in the prokaryote as well as a recombinant DNA consisting of promoter, ribosome binding sequence, DNA encoding a protein having DNA topoisomerase activity, and transcription terminator sequence. It may contain a gene controlling the promoter.

As an expression vector, pColdI (manufactured by Takara Bio), pCDF-1b, pRSF-1b (all manufactured by Novagen), pMAL-c2x (manufactured by New England Biolabs), pGEX-4T-1 (manufactured by GE Healthcare Bio-Sciences), pTrcHis (manufactured by Invitrogen), pSE280 (manufactured by Invitrogen), pGEMEX-1 (manufactured by Promega), pQE-30 (manufactured by QIAGEN), pET-3 (manufactured by Novagen), pKYP10 (JP-A-S58-110600), pKYP200 [Agric. Biol. Chem., 48, 669 (1984)], pLSA1 [Agric. Biol. Chem., 53, 277 (1989)], pGEL1 [Proc. Natl. Acad. Sci., USA, 82, 4306 (1985)], pBluescript II SK(+), pBluescript II KS(−) (manufactured by Stratagene), pTrS30 [prepared from *Escherichia coli* JM109/pTrS30 (FERM BP-5407)], pTrS32 [prepared from *Escherichia coli* JM109/pTrS32 (FERM BP-5408)], pPAC31 (WO98/12343), pUC19 [Gene, 33, 103 (1985)], pSTV28 (manufactured by Takara Bio), pUC118 (manufactured by Takara Bio), pPA1 (JP-A-S63-233798) and the like can be mentioned.

The promoter may be any as long as it can function in a host cell such as *E. coli* and the like. For example, promoters derived from *E. coli*, phage and the like, such as trp promoter ($P_{trp}$), lac promoter ($P_{lac}$), $P_L$ promoter, $P_R$ promoter, $P_{SE}$ promoter and the like, SPO1 promoter, SPO2 promoter, penP promoter and the like. In addition, artificially designed/modified promoters such as promoter having two $P_{trp}$ connected in series, tac promoter, lacT7 promoter, let I promoter and the like can also be used.

Furthermore, xylA promoter [Appl. Microbiol. Biotechnol., 35, 594-599 (1991)] for expression in a microorganism belonging to the genus *Bacillus*, P54-6 promoter [Appl. Microbiol. Biotechnol., 53, 674-679 (2000)] for expression in a microorganism belonging to the genus *Corynebacterium* and the like can also be used.

A plasmid wherein the distance between Shine-Dalgarno sequence which is a ribosome binding sequence, and an initiation codon is adjusted to a suitable distance (for example, 6-18 bases) is preferably used.

While a recombinant DNA, wherein a DNA encoding a protein having DNA topoisomerase activity is bound to an expression vector, does not necessarily require a transcription terminator sequence, a transcription terminator sequence is preferably disposed immediately downstream of a structural gene.

Examples of such recombinant DNA include pStopA, pSparCE, pCG0304 and pCG1769, which will be described later.

As a host of the recombinant DNA, the parent strain of the microorganism used in the present invention can be used.

2. Process for Producing L-Glutamine or L-Glutamic Acid of the Present Invention By culturing a microorganism that can be prepared by the method 1 above in a medium to produce and accumulate L-glutamine or L-glutamic acid in a culture, and recovering L-glutamine or L-glutamic acid from the culture, L-glutamine or L-glutamic acid can be produced.

The medium used in the process of the present invention may be any of a synthetic medium and a natural medium, as far as it contains nutrients necessary for the growth of a microorganism of the present invention, and for L-glutamine or L-glutamic acid biosynthesis, such as a carbon source, a nitrogen source, and an inorganic salt.

As the carbon source, which may be any carbon source that can be utilized by the microorganism used, saccharides such as glucose, molasses, fructose, sucrose, maltose, and soybean hydrolyzates, alcohols such as ethanol and glycerol, organic acids such as acetic acid, lactic acid and succinic acid and the like can be mentioned.

As the nitrogen source, ammonia, various inorganic or organic ammonium salts such as ammonium chloride, ammonium sulfate, ammonium carbonate, and ammonium acetate, nitrogen compounds such as urea and amines, and nitrogen-containing organic substances such as meat extract, yeast extract, corn steep liquor, peptone, and soybean hydrolyzates, and the like can be used.

As the inorganic salt, potassium monohydrogen phosphate, potassium dihydrogen phosphate, ammonium sulfate, magnesium sulfate, sodium chloride, ferrous sulfate, calcium carbonate and the like can be used.

In addition, micronutrient sources such as biotin, thiamine, nicotinamide, and nicotinic acid can be added as required. These micronutrient sources can be substituted by medium additives such as meat extract, corn steep liquor and casamino acids.

Furthermore, a substance required by a microorganism of the present invention for the growth thereof (e.g., an amino acid required for an amino acid auxotrophic microorganism) can be added as required.

The culturing is performed under aerobic conditions like shaking culture or deep spinner culture. Culturing temperature is 20 to 50° C., preferably 20 to 42° C., and more preferably 28 to 38° C. The culturing is performed while keeping the pH of the medium in the range of 5 to 11, preferably in the near-neutral range of 6 to 9. Adjustments of the pH of the medium are performed using an inorganic or organic acid, an alkali solution, urea, calcium carbonate, ammonia, a pH buffer solution and the like.

Culturing time is 5 hours to 6 days, preferably 16 hours to 3 days.

The L-glutamine or L-glutamic acid accumulated in the culture can be recovered by an ordinary method of purification. For example, L-glutamine or L-glutamic acid can be recovered, after completion of the culturing, by removing cells and solid matter from the culture by centrifugation and the like, and then performing publicly known methods such as activated charcoal treatment, ion exchange resin treatment, concentration, and crystal fractionation in combination.

Examples of the invention of this application are shown below, to which, however, the invention is not limited.

Example 1

Preparation of *Escherichia coli* Having an Ability to Produce L-Glutamine, L-Glutamic Acid (1) Construction of yeiG Gene-Expressing Plasmid A yeiG gene-expressing plasmid was constructed according to the following method.

*Escherichia coli* JM101 strain was inoculated into an LB medium [10 g/l Bacto Tryptone (manufactured by Difco), 5 g/l yeast extract (manufactured by Difco), 5 g/l sodium chloride] and cultured at 30° C. overnight. After culture, a chromosomal DNA of the microorganism was isolated and purified by a method using saturated phenol described in Current Protocols in Molecular Biology.

Based on the nucleotide sequence shown in SEQ ID NO: 1, DNAs consisting of the nucleotide sequences shown in SEQ ID NOs: 3 and 4 were synthesized as primer DNAs for yeiG gene amplification, and PCR was performed using the synthesized DNAs as a primer set.

A reaction mixture (50 µL) containing chromosomal DNA (0.1 µg) as a template, each primer (0.5 µmol/L), Pyrobest DNA polymerase (2.5 units, manufactured by Takara Bio), 10× buffer for Pyrobest DNA polymerase (5 µL, manufactured by Takara Bio), and each 200 µmol/L dNTPs (dATP, dGTP, dCTP and dTTP) was prepared, and PCR was performed by repeating 30 times a step of 15 seconds at 96° C., 30 seconds at 55° C. and 1 min at 72° C.

Amplification of an about 0.8 kb DNA fragment was confirmed, and the DNA fragment was purified according to a conventional method.

The DNA fragment and an expression vectors pTrS30 containing and trp promoter [prepared from *Escherichia coli* JM109/pTrS30 (FERM BP-5407)] were respectively digested with Hind III and Sac I, DNA fragments were separated by agarose gel electrophoresis, and a restriction enzyme-digested DNA fragments were recovered respectively using a GENECLEAN II kit (manufactured by BIO 101).

The restriction enzyme-digested fragments of 0.8 kb fragment containing a yeiG gene and a pTrs30, which were obtained above, were ligated using a DNA ligation Kit Ver.2 (manufactured by Takara Bio).

The *Escherichia coli* DH5α strain (manufactured by Takara Bio) was transformed with the obtained ligated DNA, and the transformant was selected using ampicillin resistance as an index. A plasmid was extracted from the colony of the selected transformant according to a known method, and the structure thereof was analyzed using a restriction enzyme, by which the obtainment of an expression vector pTyeiG wherein a yeiG gene was ligated to the downstream of the trp promoter was confirmed.

(2) Preparation of proBA Gene-Disrupted *Escherichia coli* JM101

(a) Construction of Marker Gene for Gene Disruption

A cat gene and a sacB gene to be used as marker genes for gene disruption and gene substitution of *Escherichia coli* using homologous recombination were isolated according to the following method. Oligonucleotides consisting of the nucleotide sequences shown in SEQ ID NOs: 5 and 6 as primers for amplifying from about 200 bp upstream to about 60 bp downstream of the cat gene on cloning vector pHSG396 (manufactured by Takara Bio) and oligonucleotides consisting of the nucleotide sequences shown in SEQ ID NOs: 7 and 8 as primers for amplifying from about 300 bp upstream to about 20 bp downstream of the sacB gene of *Bacillus subtilis* 168 strain were synthesized. The oligonucleotides consisting of the nucleotide sequences shown in SEQ ID NOs: 5 and 7 were provided with Sal I recognition site.

Using oligonucleotides consisting of the nucleotide sequences shown in SEQ ID NOs: 5 and 6 as a primer set, and pHSG396 as a template, PCR was performed to give a DNA fragment containing the cat gene. PCR was performed using Pyrobest DNA polymerase (manufactured by Takara Bio) and according to the attached explanation. In addition, using oligonucleotides consisting of the nucleotide sequences shown in SEQ ID NOs: 7 and 8 as a primer set, and a genome DNA of a wild-type strain of *Bacillus subtilis* 168 strain, which was prepared according to a conventional method, as a template, PCR was performed to give a DNA fragment containing the sacB gene.

The DNA fragment containing the cat gene and the DNA fragment containing the sacB gene were respectively purified, and cleaved with Sal I. After a phenol/chloroform treatment and ethanol precipitation, the both were mixed at an equimolar ratio, and ligated using a DNA ligation Kit Ver.2 (manufactured by Takara Bio). The ligated reaction mixture was purified by a phenol/chloroform treatment and ethanol precipitation. Using the resulting mixture as a template, and oligonucleotides consisting of the nucleotide sequences shown in SEQ ID NOs: 6 and 8 as a primer set, PCR was performed. The obtained amplified DNA was purified using a Qiaquick PCR purification kit (manufactured by QIAGEN) to give a DNA fragment containing the cat gene and the sacB gene (cat-sacB fragment).

(b) Preparation of proBA Gene-Disrupted Strain

Using oligonucleotides consisting of the nucleotide sequences shown in SEQ ID NOs: 9 and 10, and oligonucleotides consisting of the nucleotide sequences shown in SEQ ID NOs: 12 and 14 each as a primer set, and a genome DNA of *Escherichia coli* JM101 strain prepared according to a conventional method as a template, the first PCR was performed to give amplified products.

The amplified products purified using a Qiaquick PCR purification kit (manufactured by QIAGEN) and the cat-sacB fragment were mixed at an equimolar ratio. Using the mixture as a template, the second PCR was performed to give an amplified product, which was purified again using a Qiaquick PCR purification kit (manufactured by QIAGEN). The purified DNA fragment was subjected to agarose electrophoresis, by which amplification of an about 4.6 kb DNA fragment containing a peripheral proBA region inserted with the cat-sacB fragment was confirmed.

Using oligonucleotides consisting of the nucleotide sequences shown in SEQ ID NOs: 9 and 11, and oligonucleotides shown in SEQ ID NOs: 13 and 14 as respective primer sets, and a genome DNA of JM101 strain as a template, the first PCR was performed to give amplified products.

The amplified products were purified using a Qiaquick PCR purification kit (manufactured by QIAGEN) and mixed at an equimolar ratio. Using the mixture as a template, the second PCR was performed to give an amplified product, which was purified again using a Qiaquick PCR purification kit (manufactured by QIAGEN). The purified DNA fragment was subjected to agarose electrophoresis, by which amplification of an about 2 kb DNA fragment containing a peripheral proBA region defective in proBA gene was confirmed.

Then, *Escherichia coli* JM101 strain was transformed with pKD46, spread on an LB agar medium containing 100 mg/L ampicillin, and cultivated at 30° C. to select *Escherichia coli* JM101 strain possessing pKD46 (hereinafter to be referred to as *Escherichia coli* JM101/pKD46).

The DNA fragment containing a peripheral proBA gene region inserted with the cat-sacB fragment obtained above was introduced into *Escherichia coli* JM101/pKD46, which was obtained by cultivation in the presence of 10 mmol/L L-arabinose and 50 µg/ml ampicillin, by an electric pulse method.

The obtained transformant was spread on an LB agar medium (LB+chloramphenicol+ampicillin) containing 25 µg/ml chloramphenicol and 50 µg/ml ampicillin, and cultured, and a chloramphenicol resistant colony was selected. Since a strain with homologous recombination shows chloramphenicol resistance and sucrose sensitivity, the selected colony was replicated onto an LB agar medium containing 10% sucrose, 25 µg/ml chloramphenicol and 50 µg/ml ampicillin (LB+sucrose+chloramphenicol+ampicillin) and LB+chloramphenicol+ampicillin, and a strain showing chloramphenicol resistance and sucrose sensitivity was selected.

The selected strain was subjected to colony PCR using oligonucleotides consisting of the nucleotide sequences shown in SEQ ID NOs: 7 and 9 as a primer set, by which insertion of the cat-sacB fragment into the site of the proBA gene was confirmed. The strain having the cat-sacB fragment inserted into the site of the proBA gene was cultured in the same manner as above to prepare a competent cell, and the DNA fragment containing a peripheral proBA region defective in proBA gene obtained above was introduced by the electric pulse method.

The obtained transformant was cultured in an LB+sucrose agar medium, and a sucrose resistant colony was selected. Since a strain with homologous recombination does not contain a cat-sacB fragment but shows chloramphenicol sensitivity and sucrose resistance, the selected colony was replicated onto an LB+chloramphenicol agar medium and LB+sucrose agar medium, and a strain showing chloramphenicol resistance and sucrose sensitivity was selected.

A strain showing ampicillin sensitivity, that is, a strain without pKD46, was selected from the selected strains, and the strain was subjected to colony PCR using oligonucleotides consisting of the nucleotide sequences shown in SEQ ID NOs: 9 and 14 as a primer set, by which proBA gene defect was confirmed.

A proBA gene-defective strain was obtained as mentioned above and named as *Escherichia coli* JP strain. The obtained JP strain was transformed with pTyeiG obtained in (1) to give a transformant having pTyeiG, which was named as JP/pTyeiG.

Example 2

Construction of *Escherichia coli* L-Glutamine-Producing Mutant Strain which is Resistant to DNA Gyrase Inhibitor (1) Construction of Nalidixic Acid Resistant Mutant Strain JP/pTyeiG obtained in Example 1 was inoculated in a large test tube containing LB+ampicillin medium, cultured to a exponential growth phase, and spread on an M9 agar plate medium containing nalidixic acid (5 mg/L) (0.6% disodium phosphate, 0.3% potassium monophosphate, 0.05% sodium chloride, 0.1%, 0.2% glucose, 0.00147% calcium chloride dihydrate, 0.05% magnesium sulfate heptahydrate, 0.001% vitamin B1, 1.6% Bacto Agar). The agar plate medium was cultured at 30° C. for 3-5 days, and the grown colonies were separated by bacterial extraction to give mutant strains which is resistant to nalidixic acid.

85 mutant strains obtained above were inoculated in a 8 ml LB medium containing 50 µg/ml ampicillin in a large test tube, and cultured at 30° C. for 17 hr. The culture medium was inoculated at 1% in a 8 ml medium containing 100 µg/ml ampicillin [16 g/L dipotassium hydrogen phosphate, 14 g/L potassium dihydrogen phosphate, 5 g/L ammonium sulfate, 1 g/L citric acid (anhydrous), 5 g/L casamino acid (manufactured by Difco), 10 g/L glucose, 10 mg/L vitamin B1, 25 mg/L magnesium sulfate heptahydrate, 50 mg/L iron sulfate heptahydrate, 100 mg/L L-proline, adjusted with 10 mol/L sodium hydroxide to pH 7.2, and glucose, vitamin B1, magnesium sulfate heptahydrate and iron sulfate heptahydrate were separately autoclaved and added] in a test tube, and cultured at 30° C. for 24 hr. The culture medium was centrifuged and a culture supernatant was obtained. The accumulated amounts of L-glutamine and L-glutamic acid in the culture supernatant were quantified by high performance liquid chromatography (HPLC), and productivity of L-glutamine and L-glutamic acid was evaluated.

As a result, of the 85 mutant strains, 50 strains showed higher productivity of L-glutamine and L-glutamic acid than the JP/pTyeiG strain. In addition, 3 strains that showed particularly high productivity of L-glutamine or L-glutamic acid were selected and named as NAR01, NAR02 and NAR03 strains.

Table 1 shows the results of the accumulated amounts of L-glutamine and L-glutamic acid in the culture supernatant of the NAR01 strain, NAR02 strain and NAR03 strain. As shown in Table 1, the NAR01, NAR02 and NAR02 strains having nalidixic acid resistance showed remarkably improved accumulation amounts of L-glutamine and L-glutamic acid as compared to the JP/pTyeiG strain free of nalidixic acid resistance.

TABLE 1

| strain | L-Gln (g/l) | L-Glu (g/l) |
| --- | --- | --- |
| JP/pTyeiG | 0.14 | 0.05 |
| NAR01 | 0.60 | 0.20 |
| NAR02 | 0.55 | 0.54 |
| NAR03 | 0.81 | 0.12 |

(2) Identification of Mutation Introduced into Gene Encoding DNA Gyrase

Chromosomal DNAs were prepared from the NAR01, NAR02 and NAR03 strains, and subjected to PCR using oligonucleotides consisting of the nucleotide sequences shown in SEQ ID NOs: 15 and 16, and oligonucleotides consisting of the nucleotide sequences shown in SEQ ID NOs: 17 and 18 as a primer set to give 2.8 kb DNA fragments containing gyrA of each mutant strain and 2.6 kb DNA fragments containing gyrB of each mutant strain. The nucleotide sequences of these DNA fragments were determined according to a conventional method, and a polypeptide encoded by the gyrA gene of the NAR01 strain showed a mutation of substitution of the 821st Gly residue (ggc) by Ser residue (agc) and a mutation of substitution of the 830th Asp residue (gat) by Asn residue (aat) (hereinafter to be referred to as G821S D830N). Similarly, a polypeptide encoded by the gyrB gene of the NAR02 strain showed a mutation of insertion of the Glu residue (gag) into the 466th thereof (hereinafter to be referred to as 466E) and a polypeptide encoded by the gyrA gene of the NAR03 strain showed a mutation of substitution of the 84th Ala residue (gcg) by Glu residue (gag) (hereinafter to be referred to as A84E).

Example 3

(1) Preparation of *Escherichia coli* Introduced with Mutation which is Resistant to DNA Gyrase Inhibitor The mutation on the gene encoding DNA gyrase (gyrA or gyrB) found in Example 2 was introduced into the JP strain obtained in Example 1 by the following method. PCR was performed using chromosomal DNA of NAR01 or NAR03 strain as a template and the oligonucleotides consisting of the nucleotide sequences shown in SEQ ID NOs: 15 and 16 as a primer set, to amplify a 2.8 kb DNA fragment containing G821S D830N mutation in gyrA, and a 2.8 kb DNA fragment containing A84E mutation in gyrA, which were purified using a Qiaquick PCR purification kit (manufactured by QIAGEN). Similarly, PCR was performed using chromosomal DNA of NAR02 strain as a template and oligonucleotides consisting of the nucleotide sequences shown in SEQ ID NOs: 17 and 18 as a primer set to amplify a 2.6 kb DNA fragment containing 466E mutation in gyrB, which was purified using a Qiaquick PCR purification kit (manufactured by QIAGEN).

JP strain was transformed with pKD46, spread on an LB agar medium containing 100 mg/L ampicillin, and cultivated at 30° C. to select *Escherichia coli* JP strain possessing pKD46 (hereinafter to be referred to as JP/pKD46). The DNA fragment containing mutated gyrA, gyrB obtained above was introduced into JP/pKD46, which was obtained by cultivation in the presence of 10 mmol/L L-arabinose and 50 μg/ml ampicillin, by an electric pulse method.

The obtained transformant was spread on an M9 agar plate medium containing nalidixic acid 5 mg/L and cultured, and a nalidixic acid resistant strain was selected. As for gyrA G821S D830N mutation, the selected colonies were subjected to colony PCR using the oligonucleotides consisting of the nucleotide sequences shown in SEQ ID NOs: 15 and 16 as a primer set to amplify a fragment containing gyrA. The nucleotide sequence of the DNA fragment was determined by a conventional method, and substitution of the 821st Gly residue (ggc) of gyrA gene by Ser residue (agc) and substitution of the 830th Asp residue (gat) by Asn residue (aat) were confirmed. As for gyrA A84E mutation, similarly, a fragment containing gyrA was amplified by colony PCR using the oligonucleotides consisting of the nucleotide sequences shown in SEQ ID NOs: 15 and 16 as a primer set to determine the nucleotide sequence, and a strain wherein the 84th Ala residue (gcg) of gyrA gene had been substituted by Glu residue (gag) was selected. As for gyrB 466E mutation, moreover, colony PCR was performed using the oligonucleotides consisting of the nucleotide sequences shown in SEQ ID NOs: 17 and 18 as a primer set, and a strain wherein Glu residue (gag) had been inserted into the 466th of gyrB gene was selected.

In the manner mentioned above, a strain wherein the 821st Gly residue (ggc) was substituted by Ser residue (agc) and the 830th Asp residue (gat) was substituted by Asn residue (aat) in the polypeptide encoded by gyrA gene was obtained, and named as *Escherichia coli* GYR1 strain. A strain wherein the 84th Ala residue (gcg) was substituted by Glu residue (gag) in the polypeptide encoded by gyrA gene was named as *Escherichia coli* GYR2 strain. A strain wherein a Glu residue (gag) was inserted into the 466th in the polypeptide encoded by gyrB gene was obtained, and named as *Escherichia coli* GYR3 strain.

(2) Confirmation of DNA Gyrase Activity of DNA Gyrase Mutation-Introduced Strain The GYR1 strain, GYR2 strain, GYR3 strain and JP strain obtained in (1) were transformed with pBR322, spread on an LB agar medium containing 100 mg/L ampicillin and cultured at 30° C., and *Escherichia coli* GYR1 strain possessing pBR322 (hereinafter to be referred to as GYR1/pBR322), *Escherichia coli* GYR2 strain possessing pBR322 (hereinafter to be referred to as GYR2/pBR322), *Escherichia coli* GYR3 strain possessing pBR322 (hereinafter to be referred to as GYR3/pBR322), and *Escherichia coli* JP strain possessing pBR322 (hereinafter to be referred to as JP/pBR322) were selected. These transformants (two sets for each) were cultured under conditions described in Example 2(1), and nalidixic acid was added to one of them to a concentration of 200 mg/L 10 min before discontinuation of the cultivation. After discontinuation of the culture, pBR322 was extracted from each culture by using a QIAspin miniprep kit (manufactured by QIAGEN). Based on the method reported in a document (Molecular Microbiology 23: 381-386, 1997), pBR322 extracted from each bacterial body was subjected to electrophoresis under chloroquine 2.5 mg/L, or 25 mg/L addition conditions and the superhelical structures were compared.

In the JP strain, when a treatment with nalidixic acid inhibited the DNA gyrase activity and decreased pBR322 superhelix, the DNA band shifted to the upper side by electrophoresis with chloroquine 2.5 mg/L, and shifted to the lower side by electrophoresis with chloroquine 25 mg/L. On the other hand, pBR322 extracted from GYR1, GYR2 and GYR3, which are mutant strains of DNA gyrase, showed, even under conditions free of a treatment with nalidixic acid, an electrophoresis pattern similar to that of JP strain with a treatment with nalidixic acid. The above-mentioned results have clarified that the ratio of DNA having a superhelical structure, from among the DNAs in the cell, decreased from that in the parent strain due to the mutation introduced into the DNA gyrase in GYR1, GYR2 and GYR3.

Moreover, it has also been clarified that the DNA gyrase activity of GYR1, GYR2 and GYR3 is decreased as compared to that of the parent strain.

Example 4

L-Glutamine Production Test of *Escherichia coli* DNA Gyrase Mutant Strain

The GYR1, GYR2 and GYR3 strains obtained in Example 3(1) were transformed with pTyeiG and pTrs30, spread on an LB agar medium containing 100 mg/L ampicillin and cultured at 30° C. to select *Escherichia coli* GYR1 strain possessing pTyeiG or pTrs30 (hereinafter to be referred to as GYR1/pTyeiG, GYR1/pTrs30), *Escherichia coli* GYR2 strain possessing pTyeiG or pTrs30 (hereinafter to be referred to as GYR2/pTyeiG, GYR2/pTrs30), and *Escherichia coli* GYR3 strain possessing pTyeiG or pTrs30 (hereinafter to be referred to as GYR3/pTyeiG, GYR3/pTrs30). These bacterial strains were cultured under the conditions similar to those in Example 3, and the accumulated amounts of the culture products in the culture supernatant were quantified by HPLC. The results are shown in Table 2. As shown in Table 2, the accumulated amounts of L-glutamine and L-glutamic acid remarkably increased by the introduction of a mutation for decreasing DNA gyrase activity.

TABLE 2

|  | L-Gln (g/l) | L-Glu (g/l) |
| --- | --- | --- |
| JP/pTrs30 | 0.00 | 0.05 |
| JP/pTyeiG | 0.19 | 0.00 |
| GYR1/pTrs30 | 0.00 | 0.47 |

TABLE 2-continued

|  | L-Gln (g/l) | L-Glu (g/l) |
|---|---|---|
| GYR1/pTyeiG | 0.51 | 0.10 |
| GYR2/pTrs30 | 0.00 | 0.44 |
| GYR2/pTyeiG | 0.72 | 0.05 |
| GYR3/pTrs30 | 0.00 | 0.62 |
| GYR3/pTyeiG | 0.52 | 0.20 |

Example 5

(1) Construction of *Escherichia coli* which Expresses DNA Gyrase Inhibitory Protein It has been reported that forcible expression of glutamate racemase (gene name murI) in *Escherichia coli* decreases plasmid replication efficiency and DNA gyrase activity (The Journal of Biological chemistry 277: 39070-39073, 2002).

PCR was performed using synthetic DNAs consisting of the nucleotide sequences shown in SEQ ID NOs: 21 and 22 as a primer set.

PCR was performed under the conditions similar to these in Example 1(1) except that the above-mentioned primer set was used as primer DNAs. The amplified DNA fragment obtained by PCR and pSTV28 were respectively digested with EcoRI and SalI, the both DNAs were ligated in the same manner as in Example 1(1), and *Escherichia coli* DH5α strain was transformed with the ligated DNA. An expression vector, wherein the murI gene is ligated to the downstream of the lac promoter, was created according to the above-mentioned method and named as pSmurI.

JP/pTyeiG strain obtained in Example 2(1) was transformed with pSTV28 and pSmurI, spread on an LB agar medium containing 100 mg/L ampicillin and 25 mg/L chloramphenicol and cultured at 30° C. to select *Escherichia coli* JP/pTyeiG strain possessing pSTV28 or pSmurI (hereinafter to be referred to as JP/pTyeiG/pSTV28 and JP/pTyeiG/pSmurI).

(2) L-Glutamine Production Test of *Escherichia coli* which Expresses DNA Gyrase Inhibitory Protein JP/pTyeiG/pSTV28 and JP/pTyeiG/pSmurI obtained in the above-mentioned (1) were cultured under the conditions described in Example 2(1), and the accumulated amounts of the culture products in the culture supernatant were quantified by HPLC. The results are shown in Table 3. As shown in Table 3, the accumulated amount of L-glutamine remarkably increased by expressing a protein having the activity to decrease DNA gyrase activity.

TABLE 3

|  | Gln (g/l) | Glu (g/l) |
|---|---|---|
| JP/pTyeiG/pSTV28 | 0.18 | 0.06 |
| JP/pTyeiG/pSMurI | 0.33 | 0.06 |

Example 6

(1) Construction of *Escherichia coli* which Expresses DNA Topoisomerase

A plasmid that expresses *Escherichia coli* type I DNA topoisomerase (gene name topA) and a plasmid that expresses type IV DNA topoisomerase (gene name parC, parE) were constructed by the following method.

PCR was performed using synthetic DNAs consisting of the nucleotide sequences shown in SEQ ID NOs: 25 and 26 as a primer set. PCR was performed under the conditions similar to those in Example 1(1) except that the above-mentioned primer set was used as primer DNAs. A 2.8 kbp DNA fragment obtained by PCR and pSTV28% were respectively digested with SacI and SalI, the both DNAs were ligated in the same manner as in Example 1(1), and *Escherichia coli* DH5α strain was transformed with the ligated DNA. An expression vector, wherein the topA gene is ligated to the downstream of the lac promoter, was created according to the above-mentioned method and named as pStopA.

Then, PCR was performed using synthetic DNAs consisting of the nucleotide sequences shown in SEQ ID NOs: 29 and 30 as a primer set to amplify a 2.3 kbp DNA fragment.

Similarly, PCR was performed using synthetic DNAs consisting of the nucleotide sequences shown in SEQ ID NOs: 33 and 34 as a primer set to give a 1.9 kbp DNA fragment. PCR was performed under the conditions similar to those in Example 1(1) except that the above-mentioned primer set was used as primer DNAs. The amplified products were purified using a Qiaquick PCR purification kit (manufactured by QIAGEN) and mixed at an equimolar ratio. Using the mixture as a template, the second PCR was performed to give an amplified product, which was purified again using a Qiaquick PCR purification kit (manufactured by QIAGEN). The amplified DNA fragment obtained by PCR and pSTV28 were respectively digested with EcoRI and SalI, the both DNAs were ligated in the same manner as in Example 1(1), and *Escherichia coli* DH5α strain was transformed with the ligated DNA. An expression vector, wherein the parC and parE genes are ligated to the downstream of the lac promoter, was constructed according to the above-mentioned method and named as pSparCE.

JP/pTyeiG strain obtained in Example 2(1) was transformed with pSTV28, pStopA, and pSparCE, spread on an LB agar medium containing 100 mg/L ampicillin and 25 mg/L chloramphenicol and cultivated at 30° C. to select *Escherichia coli* JP/pTyeiG strain possessing pSTV28 or pStopA or pSparCE (hereinafter to be referred to as JP/pTyeiG/pSTV28, JP/pTyeiG/pStopA and JP/pTyeiG/pSparCE).

(2) L-Glutamine Production Test of *Escherichia coli* which Expresses DNA Topoisomerase JP/pTyeiG/pSTV28, JP/pTyeiG/pStopA and JP/pTyeiG/pSparCE obtained in the above-mentioned (1) were cultured under the conditions described in Example 3, and the accumulated amounts of the culture products in the culture supernatant were quantified by HPLC. The results are shown in Table 4. As shown in Table 4, the accumulated amount of L-glutamine remarkably increased by over-expression of type I and type IV DNA topoisomerases.

TABLE 4

| bacterial strain | L-Gln (g/l) | L-Glu (g/l) |
|---|---|---|
| JP/pTyeiG/pSTV28 | 0.18 | 0.06 |
| JP/pTyeiG/pStopA | 0.47 | 0.05 |
| JP/pTyeiG/pSparCE | 0.55 | 0.06 |

Example 7

(1) Construction of *Corynebacterium glutamicum* DNA Topoisomerase Overexpressing Strain A chromosomal DNA of wild-type strain ATCC13032 strain of *Corynebacterium glutamicum* was prepared by the method of Saito et al. [Biochim. Biophys. Acta, 72, 619 (1963)].

PCR was performed using synthetic DNAs consisting of the nucleotide sequences shown in SEQ ID NOs: 37 and 38, or synthetic DNAs consisting of the nucleotide sequences shown in SEQ ID NOs: 41 and 42 as a primer set. PCR was performed under the conditions similar to those in Example 1(1) except that the chromosomal DNA of wild-type ATCC13032 strain of *Corynebacterium glutamicum* was used as a template, and the above-mentioned primer set was used as a primer, and an about 3.2 kbp fragment containing NCgl0304 and the upstream thereof and an about 2.5 kbp fragment containing NCgl1769 and the upstream thereof were amplified. These fragments were purified by a Qiaquick PCR purification kit (manufactured by QIAGEN) and digested with BamHI (manufactured by Takara Bio).

pCS299P (WO2000/63388) was cleaved with BamHI (manufactured by Takara Bio), applied to an alkaline phosphatase (manufactured by Takara Bio) treatment and agarose gel electrophoresis, and a pCS299P fragment was extracted and purified by GENECLEAN Kit (manufactured by BIO 101).

An about 3.2 kbp DNA fragment containing NCgl0304, and an about 2.5 kbp DNA fragment containing NCgl1769, which were obtained above and treated with BamHI, were cloned into the pCS299P fragment in the same manner as in Example 1(1).

A restriction enzyme cleavage analysis was performed to confirm that it was a plasmid having a structure wherein about 3.2 kbp DNA fragment containing NCgl0304, obtained above, was inserted into pCS299P, and the plasmid was named as pCG0304. Similarly, a plasmid having a structure wherein about 2.5 kbp DNA fragment containing NCgl1769, obtained above, was inserted into pCS299P, and the plasmid was named as pCG1769. GLA2 strain (WO2007/074857) was transformed with these plasmids by electroporation according to the method of Rest et al. [Appl. Microbiol. Biotech., 52, 541 (1999)], spread on a BY agar medium [medium containing bouillon 20 g, yeast extract (manufactured by Difco) 5 g, Bacto Agar (manufactured by Difco) 18 g in water 1 L, adjusted to pH 7.0] added with 25 mg/L kanamycin, and cultivated at 30° C. and *Corynebacterium glutamicum* GLA2 strain possessing pCG0304 or pCG1769 (hereinafter to be referred to as GLA2/pCG0304 and GLA2/pCG1769) was selected.

(2) L-Glutamine Production Test of *Corynebacterium glutamicum* DNA Topoisomerase Overexpressing Strain GLA2/pCG0304, GLA2/pCG1769 strains obtained in the above-mentioned (1) and, as a control, a strain wherein pCS299P was introduced into GLA2 strain (hereinafter to be referred to as GLA2/pCS299P) were cultured in a BYG agar medium [medium containing glucose 10 g, meat extract 7 g, peptone 10 g, sodium chloride 3 g, yeast extract (manufactured by Difco) 5 g, Bacto Agar (manufactured by Difco) 18 g in water 1 L, adjusted to pH 7.2] added with kanamycin (25 mg/L) at 30° C. for 24 hr, each bacterial strain was inoculated in a seed medium (6 ml) [medium containing glucose 50 g, bouillon 20 g, ammonium sulfate 5 g, urea 5 g, potassium dihydrogen phosphate 2 g, magnesium sulfate heptahydrate 0.5 g, iron sulfate heptahydrate 1 mg, copper sulfate tetrahydrate 0.4 mg, zinc sulfate heptahydrate 0.9 mg, manganese chloride tetrahydrate 0.07 mg, disodium tetraborate decahydrate 0.01 mg, hexaammonium heptamolybdate tetrahydrate 0.04 mg, thiamine hydrochloride 0.5 mg, biotin 0.1 mg in water 1 L, adjusted to pH 7.2, and added with calcium carbonate 10 g] added with kanamycin (200 mg/L) in a test tube, and cultured at 30° C. for 12 hr-16 hr.

The obtained seed culture solution was inoculated at 10% in a main culture medium (30 ml) [medium containing glucose 50 g, urea 2 g, ammonium sulfate 20 g, potassium dihydrogen phosphate 0.5 g, dipotassium hydrogen phosphate 0.5 g, magnesium sulfate heptahydrate 0.5 g, iron sulfate heptahydrate 2 mg, manganese sulfate pentahydrate 2.5 mg, thiamine hydrochloride 0.5 mg, biotin 0.1 mg or 0.001 mg to water 1 L, adjusted to pH 7.0, and added with calcium carbonate 20 g] added with kanamycin (200 mg/L) in a 300 ml conical flask with a baffle, and cultured at 30° C., 220 rpm for 16 hr-18 hr without completely consuming sugar.

After completion of the culture, bacterial body was removed from the culture by centrifugation, and the accumulated amounts of L-glutamine and L-glutamic acid in the supernatant were each quantified by HPLC. The results are shown in Table 5. As shown in Table 5, the accumulated amounts of L-glutamine, L-glutamic acid remarkably increased by overexpression of type I DNA topoisomerase, also in *Corynebacterium glutamicum*.

TABLE 5

|  | L-Gln (g/l) | L-Glu (g/l) |
| --- | --- | --- |
| GLA2/pCS299P | 5.8 | 2.5 |
| GLA2/pCG0304 | 8.4 | 3.9 |
| GLA2/pCG1769 | 8.0 | 3.1 |

Example 8

(1) Construction of *Corynebacterium glutamicum* L-Glutamine and L-Glutamic Acid-Producing Mutant Strain which is Resistant to DNA Gyrase Inhibitor GS2 strain (WO2007/074857) was inoculated in a BY medium (6 ml) [medium containing meat extract 7 g, peptone 10 g, sodium chloride 3 g, yeast extract (manufactured by Difco) 5 g in water 1 L, adjusted to pH 7.2] in a large test tube, and cultured overnight to give a seed culture solution. The seed culture solution was inoculated at 1% in a BY medium (6 ml) in a large test tube, and cultured at 30° C. up to the exponential growth phase. The bacterial body was washed with saline, spread on an MMYE medium (medium containing glucose 10 g, yeast extract 1 g, ammonium sulfate 1 g, potassium dihydrogen phosphate 1 g, dipotassium hydrogen phosphate 1 g, magnesium sulfate heptahydrate 0.3 g, iron sulfate heptahydrate 10 mg, manganese sulfate pentahydrate 3.6 mg, calcium chloride dehydrate 10 mg, calcium pantothenate 10 mg, thiamine hydrochloride 5 mg and biotin 0.03 mg in water 1 L, adjusted to pH 7.2) added with nalidixic acid (75 mg/L), and cultured at 30° C. for 3-5 days. The grown colonies were separated by bacterial extraction, and mutant GNA1 strain and GNA2 strain which is resistant to DNA gyrase inhibitor were obtained.

(2) L-Glutamine and L-Glutamic Acid Production Test of *Corynebacterium Glutamicum* L-Glutamine and L-Glutamic Acid-Producing Mutant Strain which is Resistant to DNA Gyrase Inhibitor GNA1 strain, GNA2 strain and GS2 strain obtained in the above-mentioned (1) were subjected to an L-glutamine and L-glutamic acid production test under a condition described in Example 7(2) using the medium less kanamycin. The results are shown in Table 6. As shown in Table 6, the accumulated amounts of L-glutamine and L-glutamic acid remarkably increased by imparting resistance to DNA gyrase inhibitor, also in *Corynebacterium glutamicum*.

TABLE 6

|      | L-Gln (g/l) | L-Glu (g/l) |
|------|-------------|-------------|
| GS2  | 0.31        | 0.00        |
| GNA1 | 6.40        | 4.01        |
| GNA2 | 5.35        | 4.54        |

INDUSTRIAL APPLICABILITY

According to the present invention, an efficient process for producing L-glutamine or L-glutamic acid using a microorganism can be provided.

Sequence Listing Free Text
SEQ ID NO:3—explanation of artificial sequence: synthetic DNA
SEQ ID NO:4—explanation of artificial sequence: synthetic DNA
SEQ ID NO:5—explanation of artificial sequence: synthetic DNA
SEQ ID NO:6—explanation of artificial sequence: synthetic DNA
SEQ ID NO:7—explanation of artificial sequence: synthetic DNA
SEQ ID NO:8—explanation of artificial sequence: synthetic DNA
SEQ ID NO:9—explanation of artificial sequence: synthetic DNA
SEQ ID NO:10—explanation of artificial sequence: synthetic DNA
SEQ ID NO:11—explanation of artificial sequence: synthetic DNA
SEQ ID NO:12—explanation of artificial sequence: synthetic DNA
SEQ ID NO:13—explanation of artificial sequence: synthetic DNA
SEQ ID NO:14—explanation of artificial sequence: synthetic DNA
SEQ ID NO:15—explanation of artificial sequence: synthetic DNA
SEQ ID NO:16—explanation of artificial sequence: synthetic DNA
SEQ ID NO:17—explanation of artificial sequence: synthetic DNA
SEQ ID NO:18—explanation of artificial sequence: synthetic DNA
SEQ ID NO:21—explanation of artificial sequence: synthetic DNA
SEQ ID NO:22—explanation of artificial sequence: synthetic DNA
SEQ ID NO:25—explanation of artificial sequence: synthetic DNA
SEQ ID NO:26—explanation of artificial sequence: synthetic DNA
SEQ ID NO:29—explanation of artificial sequence: synthetic DNA
SEQ ID NO:30—explanation of artificial sequence: synthetic DNA
SEQ ID NO:33—explanation of artificial sequence: synthetic DNA
SEQ ID NO:34—explanation of artificial sequence: synthetic DNA
SEQ ID NO:37—explanation of artificial sequence: synthetic DNA
SEQ ID NO:38—explanation of artificial sequence: synthetic DNA
SEQ ID NO:41—explanation of artificial sequence: synthetic DNA
SEQ ID NO:42—explanation of artificial sequence: synthetic DNA

The invention claimed is:

1. A process for producing L-glutamine or L-glutamic acid which comprises:
   (a) culturing in a medium bacteria, which have an ability to produce L-glutamine or L-glutamic acid, in which an ability to form a superhelical double-stranded DNA is decreased compared with that of the parent strain, and in which the production of L-glutamine or L-glutamic acid is increased compared with that of the parent strain,
   (b) producing and accumulating L-glutamine or L-glutamic acid in the medium, and
   (c) recovering L-glutamine or L-glutamic acid from the medium.

2. The process for producing L-glutamine or L-glutamic acid according to claim 1, wherein the bacteria are the bacteria in which DNA gyrase activity is decreased compared with that of the parent strain.

3. The process for producing L-glutamine or L-glutamic acid according to claim 2, wherein the bacteria in which DNA gyrase activity is decreased compared with that of the parent strain is the bacteria in which an activity of a DNA gyrase inhibitory protein is increased compared with that of the parent strain.

4. The process for producing L-glutamine or L-glutamic acid according to claim 1, wherein the bacteria are the bacteria in which topoisomerase activity is increased compared with that of the parent strain.

* * * * *

```
                              SEQUENCE LISTING

<160> NUMBER OF SEQ ID NOS: 50

<210> SEQ ID NO 1
<211> LENGTH: 1037
<212> TYPE: DNA
<213> ORGANISM: Escherichia coli
<220> FEATURE:
<221> NAME/KEY: CDS
<222> LOCATION: (101)..(937)

<400> SEQUENCE: 1
taaaacatcg ttatgcaaat acggaagtga aagttactca cagcacattg aataaacggt      60
atgatgaaga aattgcaaac aacacaacaa ggagccacgc atg gaa atg ctc gaa     115
                                            Met Glu Met Leu Glu
                                            1               5 gag cac cgc tgt ttt gaa ggc tgg cag caa cgc tgg cga cac gac tcc     163
Glu His Arg Cys Phe Glu Gly Trp Gln Gln Arg Trp Arg His Asp Ser
            10                  15                  20 agt acc tta aac tgc ccg atg acg ttc agt atc ttt ctc cct cca cct     211
```

```
                Ser Thr Leu Asn Cys Pro Met Thr Phe Ser Ile Phe Leu Pro Pro
                         25                  30                  35 cgt gat cac act ccg cca cca gtg ctg tac tgg ctt tcc gga tta acc          259
Arg Asp His Thr Pro Pro Pro Val Leu Tyr Trp Leu Ser Gly Leu Thr
             40                  45                  50 tgc aat gac gag aac ttc acc acc aag gcg ggt gcc cag cgg gta gcg          307
Cys Asn Asp Glu Asn Phe Thr Thr Lys Ala Gly Ala Gln Arg Val Ala
 55                  60                  65 gcg gaa ctg ggg att gta ctg gtg atg cca gac acc agc ccg cgc ggc          355
Ala Glu Leu Gly Ile Val Leu Val Met Pro Asp Thr Ser Pro Arg Gly
 70                  75                  80                  85 gaa aag gtt gcc aac gac gat ggc tac gat tta ggc cag ggc gca ggc          403
Glu Lys Val Ala Asn Asp Asp Gly Tyr Asp Leu Gly Gln Gly Ala Gly
                 90                  95                 100 ttt tat ctt aat gcc acg caa ccg ccg tgg gcg acg cat tac cgg atg          451
Phe Tyr Leu Asn Ala Thr Gln Pro Pro Trp Ala Thr His Tyr Arg Met
                105                 110                 115 tat gat tat ctg cgc gat gaa tta ccg gcg ctg gtt cag tcg caa ttt          499
Tyr Asp Tyr Leu Arg Asp Glu Leu Pro Ala Leu Val Gln Ser Gln Phe
                120                 125                 130 aat gtc agc gac cgc tgc gcc att agc ggt cac tca atg ggt ggt cac          547
Asn Val Ser Asp Arg Cys Ala Ile Ser Gly His Ser Met Gly Gly His
135                 140                 145 ggt gcg ctg att atg gcg ctg aaa aat ccg ggt aaa tac acc agc gtt          595
Gly Ala Leu Ile Met Ala Leu Lys Asn Pro Gly Lys Tyr Thr Ser Val
150                 155                 160                 165 tcg gcc ttt gcg cca att gtg aat ccg tgc agc gtc ccg tgg gga atc          643
Ser Ala Phe Ala Pro Ile Val Asn Pro Cys Ser Val Pro Trp Gly Ile
                170                 175                 180 aaa gcg ttt agc agc tat tta ggt gag gac aaa aat gca tgg ctg gaa          691
Lys Ala Phe Ser Ser Tyr Leu Gly Glu Asp Lys Asn Ala Trp Leu Glu
                185                 190                 195 tgg gac agt tgc gca ctg atg tat gcc agt aac gcg cag gat gcg atc          739
Trp Asp Ser Cys Ala Leu Met Tyr Ala Ser Asn Ala Gln Asp Ala Ile
                200                 205                 210 ccg acg ctt atc gat cag ggc gat aat gat cag ttt ctt gcc gac cag          787
Pro Thr Leu Ile Asp Gln Gly Asp Asn Asp Gln Phe Leu Ala Asp Gln
                215                 220                 225 ttg caa cct gcg gta ctg gca gaa gcc gcg cgc cag aaa gcg tgg ccg          835
Leu Gln Pro Ala Val Leu Ala Glu Ala Ala Arg Gln Lys Ala Trp Pro
230                 235                 240                 245 atg acg ctg cgt att cag ccg gga tat gat cac agt tac tac ttc atc          883
Met Thr Leu Arg Ile Gln Pro Gly Tyr Asp His Ser Tyr Tyr Phe Ile
                250                 255                 260 gcc tct ttt ata gag gat cac ctg cgc ttc cat gcg cag tat tta ctg          931
Ala Ser Phe Ile Glu Asp His Leu Arg Phe His Ala Gln Tyr Leu Leu
                265                 270                 275 aag tga aagtccgccc ggttcgccgg gcatcttctc atcagaagcg ataatccact          987
Lys gccataaagt aacgacgtcc gtcttcgtta tagctgtagt cgtcacgact                  1037

<210> SEQ ID NO 2
<211> LENGTH: 278
<212> TYPE: PRT
<213> ORGANISM: Escherichia coli

<400> SEQUENCE: 2

Met Glu Met Leu Glu Glu His Arg Cys Phe Glu Gly Trp Gln Gln Arg
 1               5                  10                  15

Trp Arg His Asp Ser Ser Thr Leu Asn Cys Pro Met Thr Phe Ser Ile
```

```
                    20                  25                  30
Phe Leu Pro Pro Pro Arg Asp His Thr Pro Pro Val Leu Tyr Trp
        35                  40                  45

Leu Ser Gly Leu Thr Cys Asn Asp Glu Asn Phe Thr Thr Lys Ala Gly
    50                  55                  60

Ala Gln Arg Val Ala Ala Glu Leu Gly Ile Val Leu Val Met Pro Asp
65                  70                  75                  80

Thr Ser Pro Arg Gly Glu Lys Val Ala Asn Asp Gly Tyr Asp Leu
                85                  90                  95

Gly Gln Gly Ala Gly Phe Tyr Leu Asn Ala Thr Gln Pro Pro Trp Ala
            100                 105                 110

Thr His Tyr Arg Met Tyr Asp Tyr Leu Arg Asp Glu Leu Pro Ala Leu
            115                 120                 125

Val Gln Ser Gln Phe Asn Val Ser Asp Arg Cys Ala Ile Ser Gly His
    130                 135                 140

Ser Met Gly Gly His Gly Ala Leu Ile Met Ala Leu Lys Asn Pro Gly
145                 150                 155                 160

Lys Tyr Thr Ser Val Ser Ala Phe Ala Pro Ile Val Asn Pro Cys Ser
                165                 170                 175

Val Pro Trp Gly Ile Lys Ala Phe Ser Ser Tyr Leu Gly Glu Asp Lys
            180                 185                 190

Asn Ala Trp Leu Glu Trp Asp Ser Cys Ala Leu Met Tyr Ala Ser Asn
            195                 200                 205

Ala Gln Asp Ala Ile Pro Thr Leu Ile Asp Gln Gly Asp Asn Asp Gln
    210                 215                 220

Phe Leu Ala Asp Gln Leu Gln Pro Ala Val Leu Ala Glu Ala Ala Arg
225                 230                 235                 240

Gln Lys Ala Trp Pro Met Thr Leu Arg Ile Gln Pro Gly Tyr Asp His
                245                 250                 255

Ser Tyr Tyr Phe Ile Ala Ser Phe Ile Glu Asp His Leu Arg Phe His
            260                 265                 270

Ala Gln Tyr Leu Leu Lys
        275

<210> SEQ ID NO 3
<211> LENGTH: 29
<212> TYPE: DNA
<213> ORGANISM: Artificial Sequence
<220> FEATURE:
<223> OTHER INFORMATION: Synthetic DNA

<400> SEQUENCE: 3
tttaagctta cacaacaagg agccacgca                                    29

<210> SEQ ID NO 4
<211> LENGTH: 29
<212> TYPE: DNA
<213> ORGANISM: Artificial Sequence
<220> FEATURE:
<223> OTHER INFORMATION: Synthetic DNA

<400> SEQUENCE: 4
tttgagctcc ggactttcac ttcagtaaa                                    29

<210> SEQ ID NO 5
<211> LENGTH: 29
<212> TYPE: DNA
<213> ORGANISM: Artificial Sequence
<220> FEATURE:
```

<223> OTHER INFORMATION: Synthetic DNA

<400> SEQUENCE: 5
tttgtcgaca gaataaataa atcctggtg                                29

<210> SEQ ID NO 6
<211> LENGTH: 20
<212> TYPE: DNA
<213> ORGANISM: Artificial Sequence
<220> FEATURE:
<223> OTHER INFORMATION: Synthetic DNA

<400> SEQUENCE: 6
cacttattca ggcgtagcac                                          20

<210> SEQ ID NO 7
<211> LENGTH: 29
<212> TYPE: DNA
<213> ORGANISM: Artificial Sequence
<220> FEATURE:
<223> OTHER INFORMATION: Synthetic DNA

<400> SEQUENCE: 7
tttgtcgact ttaggcccgt agtctgcaa                                29

<210> SEQ ID NO 8
<211> LENGTH: 20
<212> TYPE: DNA
<213> ORGANISM: Artificial Sequence
<220> FEATURE:
<223> OTHER INFORMATION: Synthetic DNA

<400> SEQUENCE: 8
tatcggcatt ttcttttgcg                                          20

<210> SEQ ID NO 9
<211> LENGTH: 20
<212> TYPE: DNA
<213> ORGANISM: Artificial Sequence
<220> FEATURE:
<223> OTHER INFORMATION: Synthetic DNA

<400> SEQUENCE: 9
tcgtatttca gacctgttgc                                          20

<210> SEQ ID NO 10
<211> LENGTH: 40
<212> TYPE: DNA
<213> ORGANISM: Artificial Sequence
<220> FEATURE:
<223> OTHER INFORMATION: Synthetic DNA

<400> SEQUENCE: 10
cgcaaaagaa aatgccgata gattctctgc cattcaattt                    40

<210> SEQ ID NO 11
<211> LENGTH: 40
<212> TYPE: DNA
<213> ORGANISM: Artificial Sequence
<220> FEATURE:
<223> OTHER INFORMATION: Synthetic DNA

<400> SEQUENCE: 11
tttgcatcac ccggttttat gattctctgc cattcaattt                    40

<210> SEQ ID NO 12

```
<211> LENGTH: 40
<212> TYPE: DNA
<213> ORGANISM: Artificial Sequence
<220> FEATURE:
<223> OTHER INFORMATION: Synthetic DNA

<400> SEQUENCE: 12
gtgctacgcc tgaataagtg ataaaaccgg gtgatgcaaa                              40

<210> SEQ ID NO 13
<211> LENGTH: 40
<212> TYPE: DNA
<213> ORGANISM: Artificial Sequence
<220> FEATURE:
<223> OTHER INFORMATION: Synthetic DNA

<400> SEQUENCE: 13
aaattgaatg gcagagaatc ataaaaccgg gtgatgcaaa                              40

<210> SEQ ID NO 14
<211> LENGTH: 20
<212> TYPE: DNA
<213> ORGANISM: Artificial Sequence
<220> FEATURE:
<223> OTHER INFORMATION: Synthetic DNA

<400> SEQUENCE: 14
ctgcgaagcc gacacccttg                                                   20

<210> SEQ ID NO 15
<211> LENGTH: 20
<212> TYPE: DNA
<213> ORGANISM: Artificial Sequence
<220> FEATURE:
<223> OTHER INFORMATION: Synthetic DNA

<400> SEQUENCE: 15
attggatgtg aataaagcgt                                                   20

<210> SEQ ID NO 16
<211> LENGTH: 20
<212> TYPE: DNA
<213> ORGANISM: Artificial Sequence
<220> FEATURE:
<223> OTHER INFORMATION: Synthetic DNA

<400> SEQUENCE: 16
actttaccgt gccctaatac                                                   20

<210> SEQ ID NO 17
<211> LENGTH: 20
<212> TYPE: DNA
<213> ORGANISM: Artificial Sequence
<220> FEATURE:
<223> OTHER INFORMATION: Synthetic DNA

<400> SEQUENCE: 17
gaacacgtta tagacatgtc                                                   20

<210> SEQ ID NO 18
<211> LENGTH: 20
<212> TYPE: DNA
<213> ORGANISM: Artificial Sequence
<220> FEATURE:
<223> OTHER INFORMATION: Synthetic DNA

<400> SEQUENCE: 18
```

```
cccttatccgg cctacaaaat                                                    20
```

<210> SEQ ID NO 19
<211> LENGTH: 858
<212> TYPE: DNA
<213> ORGANISM: Escherichia coli
<220> FEATURE:
<221> NAME/KEY: CDS
<222> LOCATION: (1)..(858)

<400> SEQUENCE: 19

```
atg gct acc aaa ctg cag gac ggg aat aca cct tgt ctg gca gct aca    48
Met Ala Thr Lys Leu Gln Asp Gly Asn Thr Pro Cys Leu Ala Ala Thr
1               5                  10                  15 cct tct gaa cca cgt ccc acc gtg ctg gtg ttt gac tcc ggc gtc ggt    96
Pro Ser Glu Pro Arg Pro Thr Val Leu Val Phe Asp Ser Gly Val Gly
            20                  25                  30 ggg ttg tcg gtc tat gac gag atc cgg cat ctc tta ccg gat ctc cat   144
Gly Leu Ser Val Tyr Asp Glu Ile Arg His Leu Leu Pro Asp Leu His
        35                  40                  45 tac att tat gct ttc gat aac gtc gct ttc ccg tat ggc gaa aaa agc   192
Tyr Ile Tyr Ala Phe Asp Asn Val Ala Phe Pro Tyr Gly Glu Lys Ser
    50                  55                  60 gaa gcg ttt att gtt gag cga gtg gtg gca att gtc acc gcg gtg caa   240
Glu Ala Phe Ile Val Glu Arg Val Val Ala Ile Val Thr Ala Val Gln
65                  70                  75                  80 gaa cgt tat ccc ctt gcg ctg gct gtg gtc gct tgc aac act gcc agt   288
Glu Arg Tyr Pro Leu Ala Leu Ala Val Val Ala Cys Asn Thr Ala Ser
                85                  90                  95 acc gtt tca ctt cct gca tta cgc gaa aag ttc gac ttc ccg gtt gtt   336
Thr Val Ser Leu Pro Ala Leu Arg Glu Lys Phe Asp Phe Pro Val Val
            100                 105                 110 ggt gtc gtg ccg gcg att aaa cct gct gca cgt ctg acg gca aat ggc   384
Gly Val Val Pro Ala Ile Lys Pro Ala Ala Arg Leu Thr Ala Asn Gly
        115                 120                 125 att gtc gga tta ctg gca acc cgc gga aca gtt aaa cgt tct tat act   432
Ile Val Gly Leu Leu Ala Thr Arg Gly Thr Val Lys Arg Ser Tyr Thr
    130                 135                 140 cat gag ctg atc gcg cgt ttc gct aat gaa tgc cag ata gaa atg ctg   480
His Glu Leu Ile Ala Arg Phe Ala Asn Glu Cys Gln Ile Glu Met Leu
145                 150                 155                 160 ggc tcg gca gag atg gtt gag ttg gct gaa gcg aag cta cat ggc gaa   528
Gly Ser Ala Glu Met Val Glu Leu Ala Glu Ala Lys Leu His Gly Glu
                165                 170                 175 gat gtt tct ctg gat gca cta aaa cgt atc cta cgc ccg tgg tta aga   576
Asp Val Ser Leu Asp Ala Leu Lys Arg Ile Leu Arg Pro Trp Leu Arg
            180                 185                 190 atg aaa gag ccg cca gat acc gtt gta ttg ggt tgc acc cat ttc cct   624
Met Lys Glu Pro Pro Asp Thr Val Val Leu Gly Cys Thr His Phe Pro
        195                 200                 205 cta cta caa gaa gaa ctg tta caa gtg ctg cca gag gga acc cgg ctg   672
Leu Leu Gln Glu Glu Leu Leu Gln Val Leu Pro Glu Gly Thr Arg Leu
    210                 215                 220 gtg gat tct ggc gca gcg att gct cgc gaa acg gcc tgg ttg tta gaa   720
Val Asp Ser Gly Ala Ala Ile Ala Arg Arg Thr Ala Trp Leu Leu Glu
225                 230                 235                 240 cat gaa gcc ccg gat gca aaa tct gcc gat gcg aat att gcc ttt tgt   768
His Glu Ala Pro Asp Ala Lys Ser Ala Asp Ala Asn Ile Ala Phe Cys
                245                 250                 255 atg gca atg acg cca gga gct gaa caa tta ttg ccc gtt tta cag cgt   816
Met Ala Met Thr Pro Gly Ala Glu Gln Leu Leu Pro Val Leu Gln Arg
            260                 265                 270
```

```
tac ggc ttc gaa acg ctc gaa aaa ctg gca gtt tta ggc tga          858
Tyr Gly Phe Glu Thr Leu Glu Lys Leu Ala Val Leu Gly
        275                 280                 285
```

<210> SEQ ID NO 20
<211> LENGTH: 285
<212> TYPE: PRT
<213> ORGANISM: Escherichia coli

<400> SEQUENCE: 20

```
Met Ala Thr Lys Leu Gln Asp Gly Asn Thr Pro Cys Leu Ala Ala Thr
1               5                   10                  15

Pro Ser Glu Pro Arg Pro Thr Val Leu Val Phe Asp Ser Gly Val Gly
            20                  25                  30

Gly Leu Ser Val Tyr Asp Glu Ile Arg His Leu Leu Pro Asp Leu His
        35                  40                  45

Tyr Ile Tyr Ala Phe Asp Asn Val Ala Phe Pro Tyr Gly Glu Lys Ser
    50                  55                  60

Glu Ala Phe Ile Val Glu Arg Val Val Ala Ile Val Thr Ala Val Gln
65                  70                  75                  80

Glu Arg Tyr Pro Leu Ala Leu Ala Val Ala Cys Asn Thr Ala Ser
                85                  90                  95

Thr Val Ser Leu Pro Ala Leu Arg Glu Lys Phe Asp Phe Pro Val Val
            100                 105                 110

Gly Val Val Pro Ala Ile Lys Pro Ala Ala Arg Leu Thr Ala Asn Gly
        115                 120                 125

Ile Val Gly Leu Leu Ala Thr Arg Gly Thr Val Lys Arg Ser Tyr Thr
    130                 135                 140

His Glu Leu Ile Ala Arg Phe Ala Asn Glu Cys Gln Ile Glu Met Leu
145                 150                 155                 160

Gly Ser Ala Glu Met Val Glu Leu Ala Glu Ala Lys Leu His Gly Glu
                165                 170                 175

Asp Val Ser Leu Asp Ala Leu Lys Arg Ile Leu Arg Pro Trp Leu Arg
            180                 185                 190

Met Lys Glu Pro Pro Asp Thr Val Val Leu Gly Cys Thr His Phe Pro
        195                 200                 205

Leu Leu Gln Glu Glu Leu Leu Gln Val Leu Pro Glu Gly Thr Arg Leu
    210                 215                 220

Val Asp Ser Gly Ala Ala Ile Ala Arg Arg Thr Ala Trp Leu Leu Glu
225                 230                 235                 240

His Glu Ala Pro Asp Ala Lys Ser Ala Asp Ala Asn Ile Ala Phe Cys
                245                 250                 255

Met Ala Met Thr Pro Gly Ala Glu Gln Leu Leu Pro Val Leu Gln Arg
            260                 265                 270

Tyr Gly Phe Glu Thr Leu Glu Lys Leu Ala Val Leu Gly
        275                 280                 285
```

<210> SEQ ID NO 21
<211> LENGTH: 29
<212> TYPE: DNA
<213> ORGANISM: Artificial Sequence
<220> FEATURE:
<223> OTHER INFORMATION: Synthetic DNA

<400> SEQUENCE: 21

```
tttgaattcg tgagcttgtg ggatcttgc                                  29
```

-continued

```
<210> SEQ ID NO 22
<211> LENGTH: 29
<212> TYPE: DNA
<213> ORGANISM: Artificial Sequence
<220> FEATURE:
<223> OTHER INFORMATION: Synthetic DNA

<400> SEQUENCE: 22
tttgtcgact cagcctaaaa ctgccagtt                                          29

<210> SEQ ID NO 23
<211> LENGTH: 2598
<212> TYPE: DNA
<213> ORGANISM: Escherichia coli
<220> FEATURE:
<221> NAME/KEY: CDS
<222> LOCATION: (1)..(2598)

<400> SEQUENCE: 23
```

| | | | | | | | | | | | | | | | | |
|---|---|---|---|---|---|---|---|---|---|---|---|---|---|---|---|---|
| atg | ggt | aaa | gct | ctt | gtc | atc | gtt | gag | tcc | ccg | gca | aaa | gcc | aaa | acg | 48 |
| Met | Gly | Lys | Ala | Leu | Val | Ile | Val | Glu | Ser | Pro | Ala | Lys | Ala | Lys | Thr | |
| 1 | | | | 5 | | | | | 10 | | | | | 15 | | |
| atc | aac | aag | tat | ctg | ggt | agt | gac | tac | gtg | gtg | aaa | tcc | agc | gtc | ggt | 96 |
| Ile | Asn | Lys | Tyr | Leu | Gly | Ser | Asp | Tyr | Val | Val | Lys | Ser | Ser | Val | Gly | |
| | | 20 | | | | | 25 | | | | | 30 | | | | |
| cac | atc | cgc | gat | ttg | ccg | acc | agt | ggc | tca | gct | gcc | aaa | aag | agt | gcc | 144 |
| His | Ile | Arg | Asp | Leu | Pro | Thr | Ser | Gly | Ser | Ala | Ala | Lys | Lys | Ser | Ala | |
| | 35 | | | | | 40 | | | | | 45 | | | | | |
| gac | tct | acc | tcc | acc | aag | acg | gct | aaa | aag | cct | aaa | aag | gat | gaa | cgt | 192 |
| Asp | Ser | Thr | Ser | Thr | Lys | Thr | Ala | Lys | Lys | Pro | Lys | Lys | Asp | Glu | Arg | |
| 50 | | | | | 55 | | | | | 60 | | | | | | |
| ggc | gct | ctc | gtc | aac | cgt | atg | ggg | gtt | gac | ccg | tgg | cac | aat | tgg | gag | 240 |
| Gly | Ala | Leu | Val | Asn | Arg | Met | Gly | Val | Asp | Pro | Trp | His | Asn | Trp | Glu | |
| 65 | | | | | 70 | | | | | 75 | | | | | 80 | |
| gcg | cac | tat | gaa | gtg | ttg | cct | ggt | aaa | gag | aag | gtc | gtc | tct | gaa | ctg | 288 |
| Ala | His | Tyr | Glu | Val | Leu | Pro | Gly | Lys | Glu | Lys | Val | Val | Ser | Glu | Leu | |
| | | | | 85 | | | | | 90 | | | | | 95 | | |
| aaa | caa | ctg | gct | gaa | aaa | gcc | gac | cac | atc | tat | ctc | gca | acc | gac | ctt | 336 |
| Lys | Gln | Leu | Ala | Glu | Lys | Ala | Asp | His | Ile | Tyr | Leu | Ala | Thr | Asp | Leu | |
| | | | 100 | | | | | 105 | | | | | 110 | | | |
| gac | cgc | gaa | ggg | gaa | gcc | att | gca | tgg | cac | ctg | cgg | gaa | gtg | att | ggg | 384 |
| Asp | Arg | Glu | Gly | Glu | Ala | Ile | Ala | Trp | His | Leu | Arg | Glu | Val | Ile | Gly | |
| | | 115 | | | | | 120 | | | | | 125 | | | | |
| ggt | gat | gat | gcg | cgc | tat | agc | cga | gtg | gtg | ttt | aac | gaa | att | act | aaa | 432 |
| Gly | Asp | Asp | Ala | Arg | Tyr | Ser | Arg | Val | Val | Phe | Asn | Glu | Ile | Thr | Lys | |
| | 130 | | | | | 135 | | | | | 140 | | | | | |
| aac | gcg | atc | cgc | cag | gca | ttt | aac | aaa | ccg | ggt | gag | ctg | aat | att | gat | 480 |
| Asn | Ala | Ile | Arg | Gln | Ala | Phe | Asn | Lys | Pro | Gly | Glu | Leu | Asn | Ile | Asp | |
| 145 | | | | | 150 | | | | | 155 | | | | | 160 | |
| cgt | gtt | aat | gcc | cag | cag | gcg | cgt | cgc | ttt | atg | gac | cgc | gtg | gtg | ggg | 528 |
| Arg | Val | Asn | Ala | Gln | Gln | Ala | Arg | Arg | Phe | Met | Asp | Arg | Val | Val | Gly | |
| | | | | 165 | | | | | 170 | | | | | 175 | | |
| tat | atg | gtt | tcg | ccg | ctg | cta | tgg | aaa | aag | atc | gct | cgt | ggc | ctg | tct | 576 |
| Tyr | Met | Val | Ser | Pro | Leu | Leu | Trp | Lys | Lys | Ile | Ala | Arg | Gly | Leu | Ser | |
| | | | 180 | | | | | 185 | | | | | 190 | | | |
| gcc | ggt | cgt | gtg | cag | tcg | gtg | gcg | gtt | cgc | ctg | gtg | gtc | gag | cgt | gag | 624 |
| Ala | Gly | Arg | Val | Gln | Ser | Val | Ala | Val | Arg | Leu | Val | Val | Glu | Arg | Glu | |
| | | 195 | | | | | 200 | | | | | 205 | | | | |
| cgt | gaa | att | aaa | gcg | ttc | gtg | ccg | gaa | gag | ttc | tgg | gaa | gtc | gat | gcc | 672 |
| Arg | Glu | Ile | Lys | Ala | Phe | Val | Pro | Glu | Glu | Phe | Trp | Glu | Val | Asp | Ala | |
| | 210 | | | | | 215 | | | | | 220 | | | | | |
| agc | acg | acc | acg | cca | tct | ggt | gaa | gcg | ttg | gcg | tta | cag | gtg | act | cat | 720 |
| Ser | Thr | Thr | Thr | Pro | Ser | Gly | Glu | Ala | Leu | Ala | Leu | Gln | Val | Thr | His | |

```
              225                 230                 235                 240 cag aac gac aaa ccg ttc cgt ccg gtc aac aaa gaa caa act cag gct       768
Gln Asn Asp Lys Pro Phe Arg Pro Val Asn Lys Glu Gln Thr Gln Ala
                245                 250                 255 gcg gta agt ctg ctg gaa aaa gcg cgc tac agc gtg ctg gaa cgt gaa       816
Ala Val Ser Leu Leu Glu Lys Ala Arg Tyr Ser Val Leu Glu Arg Glu
            260                 265                 270 gac aaa ccg aca acc agt aaa cct ggc gct cct ttt att acc tct acg       864
Asp Lys Pro Thr Thr Ser Lys Pro Gly Ala Pro Phe Ile Thr Ser Thr
        275                 280                 285 ctg caa caa gct gcc agc acc cgt ctt gga ttt ggc gtg aaa aaa acc       912
Leu Gln Gln Ala Ala Ser Thr Arg Leu Gly Phe Gly Val Lys Lys Thr
    290                 295                 300 atg atg atg gcg cag cgt ttg tat gaa gca ggc tat atc act tac atg       960
Met Met Met Ala Gln Arg Leu Tyr Glu Ala Gly Tyr Ile Thr Tyr Met
305                 310                 315                 320 cgt acc gac tcc act aac ctg agt cag gac gcg gta aat atg gtt cgc      1008
Arg Thr Asp Ser Thr Asn Leu Ser Gln Asp Ala Val Asn Met Val Arg
                325                 330                 335 ggt tat atc agc gat aat ttt ggt aag aaa tat ctg ccg gaa agt ccg      1056
Gly Tyr Ile Ser Asp Asn Phe Gly Lys Lys Tyr Leu Pro Glu Ser Pro
            340                 345                 350 aat cag tac gcc agc aaa gaa aac tca cag gaa gcg cac gaa gcg att      1104
Asn Gln Tyr Ala Ser Lys Glu Asn Ser Gln Glu Ala His Glu Ala Ile
        355                 360                 365 cgt cct tct gac gtc aat gtg atg gcg gaa tcg ctg aag gat atg gaa      1152
Arg Pro Ser Asp Val Asn Val Met Ala Glu Ser Leu Lys Asp Met Glu
    370                 375                 380 gca gat gcg cag aaa ctg tac cag tta atc tgg cgt cag ttc gtt gcc      1200
Ala Asp Ala Gln Lys Leu Tyr Gln Leu Ile Trp Arg Gln Phe Val Ala
385                 390                 395                 400 tgc cag atg acc cca gcg aaa tat gac tcc acg acg ctg acc gtt ggt      1248
Cys Gln Met Thr Pro Ala Lys Tyr Asp Ser Thr Thr Leu Thr Val Gly
                405                 410                 415 gcg ggc gat ttc cgc ctg aaa gca cgc ggt cgt att ttg cgt ttt gat      1296
Ala Gly Asp Phe Arg Leu Lys Ala Arg Gly Arg Ile Leu Arg Phe Asp
            420                 425                 430 ggc tgg aca aaa gtg atg cct gcg ttg cgt aaa ggc gat gaa gat cgc      1344
Gly Trp Thr Lys Val Met Pro Ala Leu Arg Lys Gly Asp Glu Asp Arg
        435                 440                 445 atc tta cca gca gtt aat aaa ggc gat gct ctg acg ctc gtt gaa ctt      1392
Ile Leu Pro Ala Val Asn Lys Gly Asp Ala Leu Thr Leu Val Glu Leu
    450                 455                 460 aca cca gcc cag cac ttt acc aag ccg cca gcc cgt ttc agt gaa gca      1440
Thr Pro Ala Gln His Phe Thr Lys Pro Pro Ala Arg Phe Ser Glu Ala
465                 470                 475                 480 tcg ctg gtt aaa gag ctg gaa aaa cgc ggt atc ggt cgt ccg tct acc      1488
Ser Leu Val Lys Glu Leu Glu Lys Arg Gly Ile Gly Arg Pro Ser Thr
                485                 490                 495 tat gcg tcg atc att tcg acc att cag gat cgt ggc tac gtg cga gta      1536
Tyr Ala Ser Ile Ile Ser Thr Ile Gln Asp Arg Gly Tyr Val Arg Val
            500                 505                 510 gaa aat cgt cgt ttc tat gcg gaa aaa atg ggc gaa atc gtc acc gat      1584
Glu Asn Arg Arg Phe Tyr Ala Glu Lys Met Gly Glu Ile Val Thr Asp
        515                 520                 525 cgc ctt gaa gaa aat ttc cgc gag tta atg aac tac gac ttt acc gcg      1632
Arg Leu Glu Glu Asn Phe Arg Glu Leu Met Asn Tyr Asp Phe Thr Ala
    530                 535                 540 cag atg gaa aac agc ctc gac cag gtg gca aat cac gaa gca gag tgg      1680
Gln Met Glu Asn Ser Leu Asp Gln Val Ala Asn His Glu Ala Glu Trp
```

-continued

```
           545                 550                 555                 560
aaa gct gta ctg gat cac ttc ttc tcg gat ttc acc cag cag tta gat         1728
Lys Ala Val Leu Asp His Phe Phe Ser Asp Phe Thr Gln Gln Leu Asp
                    565                 570                 575 aaa gct gaa aaa gat ccg gaa gag ggt ggt atg cgc ccg aac cag atg         1776
Lys Ala Glu Lys Asp Pro Glu Glu Gly Gly Met Arg Pro Asn Gln Met
                580                 585                 590 gtt ctg acc agc att gac tgc ccg act tgt ggt cgc aaa atg ggg att         1824
Val Leu Thr Ser Ile Asp Cys Pro Thr Cys Gly Arg Lys Met Gly Ile
            595                 600                 605 cgc aca gcg agc acc ggg gta ttc ctt ggc tgt tct ggc tat gcg ctg         1872
Arg Thr Ala Ser Thr Gly Val Phe Leu Gly Cys Ser Gly Tyr Ala Leu
        610                 615                 620 ccg ccg aaa gag cgt tgc aaa acc acc att aac ctg gtg ccg gaa aac         1920
Pro Pro Lys Glu Arg Cys Lys Thr Thr Ile Asn Leu Val Pro Glu Asn
625                 630                 635                 640 gaa gtg ctg aac gtg ctg gaa ggc gaa gat gct gaa acc aac gcg ctg         1968
Glu Val Leu Asn Val Leu Glu Gly Glu Asp Ala Glu Thr Asn Ala Leu
                    645                 650                 655 cgc gca aaa cgt cgt tgc ccg aaa tgc ggc acg gcg atg gac agc tat         2016
Arg Ala Lys Arg Arg Cys Pro Lys Cys Gly Thr Ala Met Asp Ser Tyr
                660                 665                 670 ctc atc gat ccg aaa cgt aag ttg cat gtc tgt ggt aat aac cca acc         2064
Leu Ile Asp Pro Lys Arg Lys Leu His Val Cys Gly Asn Asn Pro Thr
            675                 680                 685 tgc gac ggt tac gag atc gaa gag ggc gaa ttc cgc att aaa ggt tat         2112
Cys Asp Gly Tyr Glu Ile Glu Glu Gly Glu Phe Arg Ile Lys Gly Tyr
        690                 695                 700 gac ggc ccg atc gtt gag tgt gaa aaa tgt ggc tct gaa atg cac ctg         2160
Asp Gly Pro Ile Val Glu Cys Glu Lys Cys Gly Ser Glu Met His Leu
705                 710                 715                 720 aaa atg ggg cgt ttc ggt aaa tac atg gcc tgc acc aac gaa gag tgt         2208
Lys Met Gly Arg Phe Gly Lys Tyr Met Ala Cys Thr Asn Glu Glu Cys
                    725                 730                 735 aaa aac aca cgt aag att tta cgt aac ggc gaa gtg gca cca ccg aaa         2256
Lys Asn Thr Arg Lys Ile Leu Arg Asn Gly Glu Val Ala Pro Pro Lys
                740                 745                 750 gaa gat ccg gtg cca tta cct gag ctg ccg tgc gaa aaa tca gat gct         2304
Glu Asp Pro Val Pro Leu Pro Glu Leu Pro Cys Glu Lys Ser Asp Ala
            755                 760                 765 tat ttc gtg ctg cgt gac ggt gct gcc ggt gtg ttc ctg gct gcc aac         2352
Tyr Phe Val Leu Arg Asp Gly Ala Ala Gly Val Phe Leu Ala Ala Asn
        770                 775                 780 act ttc ccg aaa tcg cgt gaa acg cgt gcg cca ctg gtg gaa gag ctt         2400
Thr Phe Pro Lys Ser Arg Glu Thr Arg Ala Pro Leu Val Glu Glu Leu
785                 790                 795                 800 tat cgc ttc cgc gac cgt ctg ccg gaa aaa ctg cgt tat ctg gcc gat         2448
Tyr Arg Phe Arg Asp Arg Leu Pro Glu Lys Leu Arg Tyr Leu Ala Asp
                    805                 810                 815 gcg cca cag cag gat ccg gaa ggt aat aag acc atg gtt cgc ttt agc         2496
Ala Pro Gln Gln Asp Pro Glu Gly Asn Lys Thr Met Val Arg Phe Ser
                820                 825                 830 cgt aaa acc aaa cag caa tat gtc tct tcg gaa aaa gac gga aag gcg         2544
Arg Lys Thr Lys Gln Gln Tyr Val Ser Ser Glu Lys Asp Gly Lys Ala
            835                 840                 845 act ggc tgg tca gca ttt tat gtt gat ggc aaa tgg gtt gaa gga aaa         2592
Thr Gly Trp Ser Ala Phe Tyr Val Asp Gly Lys Trp Val Glu Gly Lys
        850                 855                 860 aaa taa                                                                  2598
Lys
```

865

<210> SEQ ID NO 24
<211> LENGTH: 865
<212> TYPE: PRT
<213> ORGANISM: Escherichia coli

<400> SEQUENCE: 24

Met Gly Lys Ala Leu Val Ile Val Glu Ser Pro Ala Lys Ala Lys Thr
1               5                   10                  15

Ile Asn Lys Tyr Leu Gly Ser Asp Tyr Val Val Lys Ser Ser Val Gly
            20                  25                  30

His Ile Arg Asp Leu Pro Thr Ser Gly Ser Ala Ala Lys Lys Ser Ala
        35                  40                  45

Asp Ser Thr Ser Thr Lys Thr Ala Lys Lys Pro Lys Lys Asp Glu Arg
    50                  55                  60

Gly Ala Leu Val Asn Arg Met Gly Val Asp Pro Trp His Asn Trp Glu
65                  70                  75                  80

Ala His Tyr Glu Val Leu Pro Gly Lys Glu Lys Val Val Ser Glu Leu
                85                  90                  95

Lys Gln Leu Ala Glu Lys Ala Asp His Ile Tyr Leu Ala Thr Asp Leu
            100                 105                 110

Asp Arg Glu Gly Glu Ala Ile Ala Trp His Leu Arg Glu Val Ile Gly
        115                 120                 125

Gly Asp Asp Ala Arg Tyr Ser Arg Val Val Phe Asn Glu Ile Thr Lys
    130                 135                 140

Asn Ala Ile Arg Gln Ala Phe Asn Lys Pro Gly Glu Leu Asn Ile Asp
145                 150                 155                 160

Arg Val Asn Ala Gln Gln Ala Arg Arg Phe Met Asp Arg Val Val Gly
                165                 170                 175

Tyr Met Val Ser Pro Leu Leu Trp Lys Lys Ile Ala Arg Gly Leu Ser
            180                 185                 190

Ala Gly Arg Val Gln Ser Val Ala Val Arg Leu Val Val Glu Arg Glu
        195                 200                 205

Arg Glu Ile Lys Ala Phe Val Pro Glu Glu Phe Trp Glu Val Asp Ala
    210                 215                 220

Ser Thr Thr Thr Pro Ser Gly Glu Ala Leu Ala Leu Gln Val Thr His
225                 230                 235                 240

Gln Asn Asp Lys Pro Phe Arg Pro Val Asn Lys Glu Gln Thr Gln Ala
                245                 250                 255

Ala Val Ser Leu Leu Glu Lys Ala Arg Tyr Ser Val Leu Glu Arg Glu
            260                 265                 270

Asp Lys Pro Thr Thr Ser Lys Pro Gly Ala Pro Phe Ile Thr Ser Thr
        275                 280                 285

Leu Gln Gln Ala Ala Ser Thr Arg Leu Gly Phe Gly Val Lys Lys Thr
    290                 295                 300

Met Met Met Ala Gln Arg Leu Tyr Glu Ala Gly Tyr Ile Thr Tyr Met
305                 310                 315                 320

Arg Thr Asp Ser Thr Asn Leu Ser Gln Asp Ala Val Asn Met Val Arg
                325                 330                 335

Gly Tyr Ile Ser Asp Asn Phe Gly Lys Lys Tyr Leu Pro Glu Ser Pro
            340                 345                 350

Asn Gln Tyr Ala Ser Lys Glu Asn Ser Gln Glu Ala His Glu Ala Ile
        355                 360                 365

Arg Pro Ser Asp Val Asn Val Met Ala Glu Ser Leu Lys Asp Met Glu

-continued

```
            370                 375                 380
Ala Asp Ala Gln Lys Leu Tyr Gln Leu Ile Trp Arg Gln Phe Val Ala
385                 390                 395                 400

Cys Gln Met Thr Pro Ala Lys Tyr Asp Ser Thr Thr Leu Thr Val Gly
                405                 410                 415

Ala Gly Asp Phe Arg Leu Lys Ala Arg Gly Arg Ile Leu Arg Phe Asp
                420                 425                 430

Gly Trp Thr Lys Val Met Pro Ala Leu Arg Lys Gly Asp Glu Asp Arg
                435                 440                 445

Ile Leu Pro Ala Val Asn Lys Gly Asp Ala Leu Thr Leu Val Glu Leu
    450                 455                 460

Thr Pro Ala Gln His Phe Thr Lys Pro Pro Ala Arg Phe Ser Glu Ala
465                 470                 475                 480

Ser Leu Val Lys Glu Leu Glu Lys Arg Gly Ile Gly Arg Pro Ser Thr
                485                 490                 495

Tyr Ala Ser Ile Ile Ser Thr Ile Gln Asp Arg Gly Tyr Val Arg Val
                500                 505                 510

Glu Asn Arg Arg Phe Tyr Ala Glu Lys Met Gly Glu Ile Val Thr Asp
                515                 520                 525

Arg Leu Glu Glu Asn Phe Arg Glu Leu Met Asn Tyr Asp Phe Thr Ala
    530                 535                 540

Gln Met Glu Asn Ser Leu Asp Gln Val Ala Asn His Glu Ala Glu Trp
545                 550                 555                 560

Lys Ala Val Leu Asp His Phe Phe Ser Asp Phe Thr Gln Gln Leu Asp
                565                 570                 575

Lys Ala Glu Lys Asp Pro Glu Glu Gly Gly Met Arg Pro Asn Gln Met
                580                 585                 590

Val Leu Thr Ser Ile Asp Cys Pro Thr Cys Gly Arg Lys Met Gly Ile
                595                 600                 605

Arg Thr Ala Ser Thr Gly Val Phe Leu Gly Cys Ser Gly Tyr Ala Leu
    610                 615                 620

Pro Pro Lys Glu Arg Cys Lys Thr Thr Ile Asn Leu Val Pro Glu Asn
625                 630                 635                 640

Glu Val Leu Asn Val Leu Glu Gly Gly Asp Ala Glu Thr Asn Ala Leu
                645                 650                 655

Arg Ala Lys Arg Arg Cys Pro Lys Cys Gly Thr Ala Met Asp Ser Tyr
                660                 665                 670

Leu Ile Asp Pro Lys Arg Lys Leu His Val Cys Gly Asn Asn Pro Thr
                675                 680                 685

Cys Asp Gly Tyr Glu Ile Glu Glu Gly Glu Phe Arg Ile Lys Gly Tyr
    690                 695                 700

Asp Gly Pro Ile Val Glu Cys Glu Lys Cys Gly Ser Glu Met His Leu
705                 710                 715                 720

Lys Met Gly Arg Phe Gly Lys Tyr Met Ala Cys Thr Asn Glu Glu Cys
                725                 730                 735

Lys Asn Thr Arg Lys Ile Leu Arg Asn Gly Glu Val Ala Pro Pro Lys
                740                 745                 750

Glu Asp Pro Val Pro Leu Pro Glu Leu Pro Cys Glu Lys Ser Asp Ala
                755                 760                 765

Tyr Phe Val Leu Arg Asp Gly Ala Ala Gly Val Phe Leu Ala Ala Asn
    770                 775                 780

Thr Phe Pro Lys Ser Arg Glu Thr Arg Ala Pro Leu Val Glu Glu Leu
785                 790                 795                 800
```

```
Tyr Arg Phe Arg Asp Arg Leu Pro Glu Lys Leu Arg Tyr Leu Ala Asp
                805                 810                 815

Ala Pro Gln Gln Asp Pro Glu Gly Asn Lys Thr Met Val Arg Phe Ser
            820                 825                 830

Arg Lys Thr Lys Gln Gln Tyr Val Ser Ser Glu Lys Asp Gly Lys Ala
        835                 840                 845

Thr Gly Trp Ser Ala Phe Tyr Val Asp Gly Lys Trp Val Glu Gly Lys
    850                 855                 860

Lys
865

<210> SEQ ID NO 25
<211> LENGTH: 29
<212> TYPE: DNA
<213> ORGANISM: Artificial Sequence
<220> FEATURE:
<223> OTHER INFORMATION: Synthetic DNA

<400> SEQUENCE: 25
tttgagctcg acattcgacc aaaattccg                                  29

<210> SEQ ID NO 26
<211> LENGTH: 34
<212> TYPE: DNA
<213> ORGANISM: Artificial Sequence
<220> FEATURE:
<223> OTHER INFORMATION: Synthetic DNA

<400> SEQUENCE: 26
tttgtcgact tattttttc cttcaaccca tttg                             34

<210> SEQ ID NO 27
<211> LENGTH: 2259
<212> TYPE: DNA
<213> ORGANISM: Escherichia coli
<220> FEATURE:
<221> NAME/KEY: CDS
<222> LOCATION: (1)..(2259)

<400> SEQUENCE: 27 atg agc gat atg gca gag cgc ctt gcg cta cat gaa ttt acg gaa aac     48
Met Ser Asp Met Ala Glu Arg Leu Ala Leu His Glu Phe Thr Glu Asn
1               5                   10                  15 gcc tac tta aac tac tcc atg tac gtg atc atg gac cgt gcg ttg ccg     96
Ala Tyr Leu Asn Tyr Ser Met Tyr Val Ile Met Asp Arg Ala Leu Pro
            20                  25                  30 ttt att ggt gat ggt ctg aaa cct gtt cag cgc cgc att gtg tat gcg    144
Phe Ile Gly Asp Gly Leu Lys Pro Val Gln Arg Arg Ile Val Tyr Ala
        35                  40                  45 atg tct gaa ctg ggc ctg aat gcc agc gcc aaa ttt aaa aaa tcg gcc    192
Met Ser Glu Leu Gly Leu Asn Ala Ser Ala Lys Phe Lys Lys Ser Ala
    50                  55                  60 cgt acc gtc ggt gac gta ctg ggt aaa tac cat ccg cac ggc gat agc    240
Arg Thr Val Gly Asp Val Leu Gly Lys Tyr His Pro His Gly Asp Ser
65                  70                  75                  80 gcc tgt tat gaa gcg atg gtc ctg atg gcg caa ccg ttc tct tac cgt    288
Ala Cys Tyr Glu Ala Met Val Leu Met Ala Gln Pro Phe Ser Tyr Arg
                85                  90                  95 tat ccg ctg gtt gat ggt cag ggg aac tgg ggc gcg ccg gac gat ccg    336
Tyr Pro Leu Val Asp Gly Gln Gly Asn Trp Gly Ala Pro Asp Asp Pro
            100                 105                 110 aaa tcg ttc gcg gca atg cgt tac acc gaa tcc cgg ttg tcg aaa tat    384
Lys Ser Phe Ala Ala Met Arg Tyr Thr Glu Ser Arg Leu Ser Lys Tyr
```

-continued

```
            115                 120                      125
tcc gag ctg cta ttg agc gag ctg ggg cag ggg acg gct gac tgg gtg       432
Ser Glu Leu Leu Leu Ser Glu Leu Gly Gln Gly Thr Ala Asp Trp Val
    130                 135                      140 cca aac ttc gac ggc act ttg cag gag ccg aaa atg cta cct gcc cgt       480
Pro Asn Phe Asp Gly Thr Leu Gln Glu Pro Lys Met Leu Pro Ala Arg
145                 150                      155                 160 ctg cca aac att ttg ctt aac ggc acc acc ggt att gcc gtc ggc atg       528
Leu Pro Asn Ile Leu Leu Asn Gly Thr Thr Gly Ile Ala Val Gly Met
            165                 170                      175 gcg acc gat att cca ccg cat aac ctg cgt gaa gtg gct cag gcg gca       576
Ala Thr Asp Ile Pro Pro His Asn Leu Arg Glu Val Ala Gln Ala Ala
                180                 185                      190 atc gca tta atc gac cag ccg aaa acc acg ctc gat cag ctg ctg gat       624
Ile Ala Leu Ile Asp Gln Pro Lys Thr Thr Leu Asp Gln Leu Leu Asp
        195                 200                      205 atc gtg cag ggg ccg gat tat ccg act gaa gcg gaa att atc act tcg       672
Ile Val Gln Gly Pro Asp Tyr Pro Thr Glu Ala Glu Ile Ile Thr Ser
    210                 215                      220 cgc gcc gag atc cgt aaa atc tac gag aac gga cgt ggt tca gtg cgt       720
Arg Ala Glu Ile Arg Lys Ile Tyr Glu Asn Gly Arg Gly Ser Val Arg
225                 230                      235                 240 atg cgc gcg gtg tgg aag aaa gaa gat ggc gcg gtg gtt atc agc gca       768
Met Arg Ala Val Trp Lys Lys Glu Asp Gly Ala Val Val Ile Ser Ala
            245                 250                      255 ttg ccg cat cag gtt tca ggt gcg cgc gta ctg gag caa att gct gcg       816
Leu Pro His Gln Val Ser Gly Ala Arg Val Leu Glu Gln Ile Ala Ala
                260                 265                      270 caa atg cgc aac aaa aag ctg ccg atg gtt gac gat ctg cgc gat gaa       864
Gln Met Arg Asn Lys Lys Leu Pro Met Val Asp Asp Leu Arg Asp Glu
        275                 280                      285 tct gac cac gag aac ccg acc cgc ctg gtg att gtg ccg cgt tcc aac       912
Ser Asp His Glu Asn Pro Thr Arg Leu Val Ile Val Pro Arg Ser Asn
    290                 295                      300 cgc gtg gat atg gat cag gtg atg aac cac ctc ttc gct acc acc gat       960
Arg Val Asp Met Asp Gln Val Met Asn His Leu Phe Ala Thr Thr Asp
305                 310                      315                 320 ctg gaa aag agc tat cgt att aac ctt aat atg atc ggt ctg gat ggt      1008
Leu Glu Lys Ser Tyr Arg Ile Asn Leu Asn Met Ile Gly Leu Asp Gly
            325                 330                      335 cgt ccg gcg gtg aaa aac ctg ctg gaa atc ctc tcc gaa tgg ctg gtg      1056
Arg Pro Ala Val Lys Asn Leu Leu Glu Ile Leu Ser Glu Trp Leu Val
                340                 345                      350 ttc cgc cgc gat acc gtg cgc cgc cga ctg aac tat cgt ctg gag aaa      1104
Phe Arg Arg Asp Thr Val Arg Arg Arg Leu Asn Tyr Arg Leu Glu Lys
        355                 360                      365 gtc ctc aag cgc ctg cat atc ctc gaa ggt ttg ctg gtg gcg ttt ctc      1152
Val Leu Lys Arg Leu His Ile Leu Glu Gly Leu Leu Val Ala Phe Leu
    370                 375                      380 aat atc gac gaa gtg att gag atc att cgt aat gaa gat gaa ccg aaa      1200
Asn Ile Asp Glu Val Ile Glu Ile Ile Arg Asn Glu Asp Glu Pro Lys
385                 390                      395                 400 ccg gcg ctg atg tcg cgg ttt ggc ctt acg gaa acc cag gcg gaa gcg      1248
Pro Ala Leu Met Ser Arg Phe Gly Leu Thr Glu Thr Gln Ala Glu Ala
            405                 410                      415 atc ctc gaa ctg aaa ctg cgt cat ctt gcc aaa ctg gaa gag atg aag      1296
Ile Leu Glu Leu Lys Leu Arg His Leu Ala Lys Leu Glu Glu Met Lys
                420                 425                      430 att cgc ggt gag cag agt gaa ctg gaa aaa gag cgc gac cag ttg cag      1344
Ile Arg Gly Glu Gln Ser Glu Leu Glu Lys Glu Arg Asp Gln Leu Gln
```

```
                      435                 440                 445
ggc att ttg gct tcc gag cgt aaa atg aat aac ctg ctg aag aaa gaa    1392
Gly Ile Leu Ala Ser Glu Arg Lys Met Asn Asn Leu Leu Lys Lys Glu
450                 455                 460 ctg cag gca gac gcg caa gcc tac ggt gac gat cgt cgt tcg ccg ttg    1440
Leu Gln Ala Asp Ala Gln Ala Tyr Gly Asp Asp Arg Arg Ser Pro Leu
465                 470                 475                 480 cag gaa cgc gaa gaa gcg aaa gcg atg agc gag cac gac atg ctg ccg    1488
Gln Glu Arg Glu Glu Ala Lys Ala Met Ser Glu His Asp Met Leu Pro
            485                 490                 495 tct gaa cct gtc acc att gtg ctg tcg cag atg ggc tgg gta cgc agc    1536
Ser Glu Pro Val Thr Ile Val Leu Ser Gln Met Gly Trp Val Arg Ser
500                 505                 510 gct aaa ggc cat gat atc gac gcg ccg ggc ctg aat tat aaa gcg ggt    1584
Ala Lys Gly His Asp Ile Asp Ala Pro Gly Leu Asn Tyr Lys Ala Gly
515                 520                 525 gat agc ttc aaa gcg gcg gtg aaa ggt aag agc aac caa ccg gta gtg    1632
Asp Ser Phe Lys Ala Ala Val Lys Gly Lys Ser Asn Gln Pro Val Val
530                 535                 540 ttt gtt gat tcc acc ggt cgt agc tat gcc att gac ccg att acg ctg    1680
Phe Val Asp Ser Thr Gly Arg Ser Tyr Ala Ile Asp Pro Ile Thr Leu
545                 550                 555                 560 ccg tcg gcg cgt ggt cag ggc gag ccg ctc acc ggc aaa tta acg ttg    1728
Pro Ser Ala Arg Gly Gln Gly Glu Pro Leu Thr Gly Lys Leu Thr Leu
                565                 570                 575 ccg cct ggg gcg acc gtt gac cat atg ctg atg gaa agc gac gat cag    1776
Pro Pro Gly Ala Thr Val Asp His Met Leu Met Glu Ser Asp Asp Gln
            580                 585                 590 aaa ctg ctg atg gct tcc gat gcg ggt tac ggt ttc gtc tgc acc ttt    1824
Lys Leu Leu Met Ala Ser Asp Ala Gly Tyr Gly Phe Val Cys Thr Phe
            595                 600                 605 aac gat ctg gtg gcg cgt aac cgt gca ggt aag gct ttg atc acc tta    1872
Asn Asp Leu Val Ala Arg Asn Arg Ala Gly Lys Ala Leu Ile Thr Leu
610                 615                 620 ccg gaa aat gcc cat gtt atg ccg ccg gtg gtg att gaa gat gct tcc    1920
Pro Glu Asn Ala His Val Met Pro Pro Val Val Ile Glu Asp Ala Ser
625                 630                 635                 640 gat atg ctg ctg gca atc act cag gca ggc cgt atg ttg atg ttc ccg    1968
Asp Met Leu Leu Ala Ile Thr Gln Ala Gly Arg Met Leu Met Phe Pro
                645                 650                 655 gta agt gat ctg ccg cag ctg tcg aag ggc aaa ggc aac aag att atc    2016
Val Ser Asp Leu Pro Gln Leu Ser Lys Gly Lys Gly Asn Lys Ile Ile
            660                 665                 670 aac att cca tcg gca gaa gcc gcg cgt gga gaa gat ggt ctg gcg caa    2064
Asn Ile Pro Ser Ala Glu Ala Ala Arg Gly Glu Asp Gly Leu Ala Gln
            675                 680                 685 ttg tac gtt ctg ccg ccg caa agc acg ctg acc att cat gtt ggg aaa    2112
Leu Tyr Val Leu Pro Pro Gln Ser Thr Leu Thr Ile His Val Gly Lys
690                 695                 700 cgc aaa att aaa ctg cgc ccg gaa gag tta cag aaa gtc act ggc gaa    2160
Arg Lys Ile Lys Leu Arg Pro Glu Glu Leu Gln Lys Val Thr Gly Glu
705                 710                 715                 720 cgt gga cgc cgc ggt acg ttg atg cgc ggt ttg cag cgt atc gat cgt    2208
Arg Gly Arg Arg Gly Thr Leu Met Arg Gly Leu Gln Arg Ile Asp Arg
                725                 730                 735 gtt gag atc gac tct cct cgc cgt gcc agc agc ggt gat agc gaa gag    2256
Val Glu Ile Asp Ser Pro Arg Arg Ala Ser Ser Gly Asp Ser Glu Glu
            740                 745                 750 taa                                                                 2259
```

```
<210> SEQ ID NO 28
<211> LENGTH: 752
<212> TYPE: PRT
<213> ORGANISM: Escherichia coli

<400> SEQUENCE: 28

Met Ser Asp Met Ala Glu Arg Leu Ala Leu His Glu Phe Thr Glu Asn
1               5                   10                  15

Ala Tyr Leu Asn Tyr Ser Met Tyr Val Ile Met Asp Arg Ala Leu Pro
            20                  25                  30

Phe Ile Gly Asp Gly Leu Lys Pro Val Gln Arg Arg Ile Val Tyr Ala
        35                  40                  45

Met Ser Glu Leu Gly Leu Asn Ala Ser Ala Lys Phe Lys Lys Ser Ala
    50                  55                  60

Arg Thr Val Gly Asp Val Leu Gly Lys Tyr His Pro His Gly Asp Ser
65                  70                  75                  80

Ala Cys Tyr Glu Ala Met Val Leu Met Ala Gln Pro Phe Ser Tyr Arg
                85                  90                  95

Tyr Pro Leu Val Asp Gly Gln Gly Asn Trp Gly Ala Pro Asp Asp Pro
            100                 105                 110

Lys Ser Phe Ala Ala Met Arg Tyr Thr Glu Ser Arg Leu Ser Lys Tyr
        115                 120                 125

Ser Glu Leu Leu Leu Ser Glu Leu Gly Gln Gly Thr Ala Asp Trp Val
    130                 135                 140

Pro Asn Phe Asp Gly Thr Leu Gln Glu Pro Lys Met Leu Pro Ala Arg
145                 150                 155                 160

Leu Pro Asn Ile Leu Leu Asn Gly Thr Gly Ile Ala Val Gly Met
                165                 170                 175

Ala Thr Asp Ile Pro Pro His Asn Leu Arg Glu Val Ala Gln Ala Ala
            180                 185                 190

Ile Ala Leu Ile Asp Gln Pro Lys Thr Thr Leu Asp Gln Leu Leu Asp
        195                 200                 205

Ile Val Gln Gly Pro Asp Tyr Pro Thr Glu Ala Glu Ile Ile Thr Ser
    210                 215                 220

Arg Ala Glu Ile Arg Lys Ile Tyr Glu Asn Gly Arg Gly Ser Val Arg
225                 230                 235                 240

Met Arg Ala Val Trp Lys Lys Glu Asp Gly Ala Val Val Ile Ser Ala
                245                 250                 255

Leu Pro His Gln Val Ser Gly Ala Arg Val Leu Glu Gln Ile Ala Ala
            260                 265                 270

Gln Met Arg Asn Lys Lys Leu Pro Met Val Asp Asp Leu Arg Asp Glu
        275                 280                 285

Ser Asp His Glu Asn Pro Thr Arg Leu Val Ile Val Pro Arg Ser Asn
    290                 295                 300

Arg Val Asp Met Asp Gln Val Met Asn His Leu Phe Ala Thr Thr Asp
305                 310                 315                 320

Leu Glu Lys Ser Tyr Arg Ile Asn Leu Asn Met Ile Gly Leu Asp Gly
                325                 330                 335

Arg Pro Ala Val Lys Asn Leu Leu Glu Ile Leu Ser Glu Trp Leu Val
            340                 345                 350

Phe Arg Arg Asp Thr Val Arg Arg Leu Asn Tyr Arg Leu Glu Lys
        355                 360                 365

Val Leu Lys Arg Leu His Ile Leu Glu Gly Leu Leu Val Ala Phe Leu
    370                 375                 380
```

Asn Ile Asp Glu Val Ile Glu Ile Ile Arg Asn Glu Asp Glu Pro Lys
385                 390                 395                 400

Pro Ala Leu Met Ser Arg Phe Gly Leu Thr Glu Thr Gln Ala Glu Ala
            405                 410                 415

Ile Leu Glu Leu Lys Leu Arg His Leu Ala Lys Leu Gly Glu Met Lys
        420                 425                 430

Ile Arg Gly Glu Gln Ser Glu Leu Gly Lys Glu Arg Asp Gln Leu Gln
    435                 440                 445

Gly Ile Leu Ala Ser Glu Arg Lys Met Asn Asn Leu Leu Lys Lys Glu
450                 455                 460

Leu Gln Ala Asp Ala Gln Ala Tyr Gly Asp Asp Arg Arg Ser Pro Leu
465                 470                 475                 480

Gln Glu Arg Glu Glu Ala Lys Ala Met Ser Glu His Asp Met Leu Pro
            485                 490                 495

Ser Glu Pro Val Thr Ile Val Leu Ser Gln Met Gly Trp Val Arg Ser
        500                 505                 510

Ala Lys Gly His Asp Ile Asp Ala Pro Gly Leu Asn Tyr Lys Ala Gly
    515                 520                 525

Asp Ser Phe Lys Ala Ala Val Lys Gly Lys Ser Asn Gln Pro Val Val
530                 535                 540

Phe Val Asp Ser Thr Gly Arg Ser Tyr Ala Ile Asp Pro Ile Thr Leu
545                 550                 555                 560

Pro Ser Ala Arg Gly Gln Gly Glu Pro Leu Thr Gly Lys Leu Thr Leu
            565                 570                 575

Pro Pro Gly Ala Thr Val Asp His Met Leu Met Glu Ser Asp Asp Gln
        580                 585                 590

Lys Leu Leu Met Ala Ser Asp Ala Gly Tyr Gly Phe Val Cys Thr Phe
    595                 600                 605

Asn Asp Leu Val Ala Arg Asn Arg Ala Gly Lys Ala Leu Ile Thr Leu
610                 615                 620

Pro Glu Asn Ala His Val Met Pro Val Val Ile Glu Asp Ala Ser
625                 630                 635                 640

Asp Met Leu Leu Ala Ile Thr Gln Ala Gly Arg Met Leu Met Phe Pro
            645                 650                 655

Val Ser Asp Leu Pro Gln Leu Ser Lys Gly Lys Gly Asn Lys Ile Ile
        660                 665                 670

Asn Ile Pro Ser Ala Glu Ala Arg Gly Glu Asp Gly Leu Ala Gln
    675                 680                 685

Leu Tyr Val Leu Pro Pro Gln Ser Thr Leu Thr Ile His Val Gly Lys
690                 695                 700

Arg Lys Ile Lys Leu Arg Pro Glu Glu Leu Gln Lys Val Thr Gly Glu
705                 710                 715                 720

Arg Gly Arg Arg Gly Thr Leu Met Arg Gly Leu Gln Arg Ile Asp Arg
            725                 730                 735

Val Glu Ile Asp Ser Pro Arg Arg Ala Ser Ser Gly Asp Ser Glu Glu
        740                 745                 750

<210> SEQ ID NO 29
<211> LENGTH: 30
<212> TYPE: DNA
<213> ORGANISM: Artificial Sequence
<220> FEATURE:
<223> OTHER INFORMATION: Synthetic DNA

<400> SEQUENCE: 29
tttgaattcg atgagcgata tggcagagcg                                    30

<210> SEQ ID NO 30
<211> LENGTH: 40
<212> TYPE: DNA
<213> ORGANISM: Artificial Sequence
<220> FEATURE:
<223> OTHER INFORMATION: Synthetic DNA

<400> SEQUENCE: 30
atggtttaag ttagtaattc ttactcttcg ctatcaccgc                                40

<210> SEQ ID NO 31
<211> LENGTH: 1893
<212> TYPE: DNA
<213> ORGANISM: Escherichia coli
<220> FEATURE:
<221> NAME/KEY: CDS
<222> LOCATION: (1)..(1893)

<400> SEQUENCE: 31

| atg | acg | caa | act | tat | aac | gct | gat | gcc | att | gag | gta | ctc | acc | ggg | ctt | 48 |
|---|---|---|---|---|---|---|---|---|---|---|---|---|---|---|---|---|
| Met | Thr | Gln | Thr | Tyr | Asn | Ala | Asp | Ala | Ile | Glu | Val | Leu | Thr | Gly | Leu | |
| 1 | | | | 5 | | | | | 10 | | | | | 15 | | |

| gag | ccg | gtt | cgc | cgt | cgt | ccg | ggg | atg | tat | acc | gat | acc | act | cgc | cct | 96 |
|---|---|---|---|---|---|---|---|---|---|---|---|---|---|---|---|---|
| Glu | Pro | Val | Arg | Arg | Arg | Pro | Gly | Met | Tyr | Thr | Asp | Thr | Thr | Arg | Pro | |
| | | | 20 | | | | | 25 | | | | | 30 | | | |

| aac | cat | ttg | ggg | caa | gaa | gtc | att | gat | aac | agt | gtg | gat | gaa | gca | ctg | 144 |
|---|---|---|---|---|---|---|---|---|---|---|---|---|---|---|---|---|
| Asn | His | Leu | Gly | Gln | Glu | Val | Ile | Asp | Asn | Ser | Val | Asp | Glu | Ala | Leu | |
| | | 35 | | | | | 40 | | | | | 45 | | | | |

| gcg | ggt | cac | gca | aaa | cgc | gtg | gac | gtt | att | tta | cat | gct | gac | cag | tcg | 192 |
|---|---|---|---|---|---|---|---|---|---|---|---|---|---|---|---|---|
| Ala | Gly | His | Ala | Lys | Arg | Val | Asp | Val | Ile | Leu | His | Ala | Asp | Gln | Ser | |
| 50 | | | | | 55 | | | | | 60 | | | | | | |

| tta | gaa | gtt | att | gac | gat | ggg | cgc | ggg | atg | ccg | gtg | gat | att | cac | ccg | 240 |
|---|---|---|---|---|---|---|---|---|---|---|---|---|---|---|---|---|
| Leu | Glu | Val | Ile | Asp | Asp | Gly | Arg | Gly | Met | Pro | Val | Asp | Ile | His | Pro | |
| 65 | | | | 70 | | | | | 75 | | | | | 80 | | |

| gaa | gag | ggt | gta | ccg | gcg | gtt | gaa | ctg | att | ctt | tgc | cgt | ctg | cat | gca | 288 |
|---|---|---|---|---|---|---|---|---|---|---|---|---|---|---|---|---|
| Glu | Glu | Gly | Val | Pro | Ala | Val | Glu | Leu | Ile | Leu | Cys | Arg | Leu | His | Ala | |
| | | | | 85 | | | | | 90 | | | | | 95 | | |

| ggc | ggt | aaa | ttc | tct | aac | aaa | aat | tac | cag | ttc | tct | ggc | ggc | ctg | cat | 336 |
|---|---|---|---|---|---|---|---|---|---|---|---|---|---|---|---|---|
| Gly | Gly | Lys | Phe | Ser | Asn | Lys | Asn | Tyr | Gln | Phe | Ser | Gly | Gly | Leu | His | |
| | | 100 | | | | | 105 | | | | | 110 | | | | |

| ggc | gtg | ggg | att | tcg | gtg | gtt | aac | gcc | ctg | tcg | aag | cgc | gta | gaa | gtt | 384 |
|---|---|---|---|---|---|---|---|---|---|---|---|---|---|---|---|---|
| Gly | Val | Gly | Ile | Ser | Val | Val | Asn | Ala | Leu | Ser | Lys | Arg | Val | Glu | Val | |
| | | | 115 | | | | | 120 | | | | | 125 | | | |

| aac | gtg | cgc | cgc | gat | ggt | cag | gtt | tat | aac | atc | gcc | ttt | gaa | aat | ggc | 432 |
|---|---|---|---|---|---|---|---|---|---|---|---|---|---|---|---|---|
| Asn | Val | Arg | Arg | Asp | Gly | Gln | Val | Tyr | Asn | Ile | Ala | Phe | Glu | Asn | Gly | |
| | 130 | | | | | 135 | | | | | 140 | | | | | |

| gaa | aag | gtg | cag | gat | tta | cag | gtt | gtc | ggc | act | tgc | ggt | aaa | cgc | aat | 480 |
|---|---|---|---|---|---|---|---|---|---|---|---|---|---|---|---|---|
| Glu | Lys | Val | Gln | Asp | Leu | Gln | Val | Val | Gly | Thr | Cys | Gly | Lys | Arg | Asn | |
| 145 | | | | | 150 | | | | | 155 | | | | | 160 | |

| act | ggt | acc | agt | gtg | cac | ttc | tgg | ccg | gat | gaa | acc | ttc | ttt | gac | agc | 528 |
|---|---|---|---|---|---|---|---|---|---|---|---|---|---|---|---|---|
| Thr | Gly | Thr | Ser | Val | His | Phe | Trp | Pro | Asp | Glu | Thr | Phe | Phe | Asp | Ser | |
| | | | | 165 | | | | | 170 | | | | | 175 | | |

| ccg | cga | ttt | tct | gtt | tca | cgc | ctg | acg | cat | gtg | ctg | aaa | gcc | aaa | gcg | 576 |
|---|---|---|---|---|---|---|---|---|---|---|---|---|---|---|---|---|
| Pro | Arg | Phe | Ser | Val | Ser | Arg | Leu | Thr | His | Val | Leu | Lys | Ala | Lys | Ala | |
| | | | 180 | | | | | 185 | | | | | 190 | | | |

| gta | ttg | tgc | cct | ggc | gtt | gag | atc | act | ttt | aaa | gat | gag | atc | aac | aat | 624 |
|---|---|---|---|---|---|---|---|---|---|---|---|---|---|---|---|---|
| Val | Leu | Cys | Pro | Gly | Val | Glu | Ile | Thr | Phe | Lys | Asp | Glu | Ile | Asn | Asn | |
| | | | 195 | | | | | 200 | | | | | 205 | | | |

| acc | gaa | caa | cgc | tgg | tgc | tat | cag | gac | ggt | ctg | aat | gat | tac | ctg | gcg | 672 |
|---|---|---|---|---|---|---|---|---|---|---|---|---|---|---|---|---|
| Thr | Glu | Gln | Arg | Trp | Cys | Tyr | Gln | Asp | Gly | Leu | Asn | Asp | Tyr | Leu | Ala | |
| | 210 | | | | | 215 | | | | | 220 | | | | | |

```
gaa gcg gta aat ggt ctg ccg acg ctg ccg gaa aaa ccg ttt atc ggt      720
Glu Ala Val Asn Gly Leu Pro Thr Leu Pro Glu Lys Pro Phe Ile Gly
225                 230                 235                 240 aat ttc gct ggt gat act gaa gct gtg gac tgg gcg cta ctg tgg ctg      768
Asn Phe Ala Gly Asp Thr Glu Ala Val Asp Trp Ala Leu Leu Trp Leu
                245                 250                 255 ccg gaa ggc ggt gaa ctg ctg acc gaa agc tac gtc aac ctt atc cca      816
Pro Glu Gly Gly Glu Leu Leu Thr Glu Ser Tyr Val Asn Leu Ile Pro
            260                 265                 270 acg atg cag ggc ggt acc cat gtt aat ggt ctg cgt cag ggc ctg ttg      864
Thr Met Gln Gly Gly Thr His Val Asn Gly Leu Arg Gln Gly Leu Leu
        275                 280                 285 gac gcg atg cgt gag ttc tgt gaa tac cgc aat att ctg ccg cgc ggt      912
Asp Ala Met Arg Glu Phe Cys Glu Tyr Arg Asn Ile Leu Pro Arg Gly
    290                 295                 300 gta aag ctg tcg gcg gaa gat atc tgg gat cgc tgc gcc tat gtg ctg      960
Val Lys Leu Ser Ala Glu Asp Ile Trp Asp Arg Cys Ala Tyr Val Leu
305                 310                 315                 320 tca gta aaa atg cag gat ccg cag ttt gcc ggg cag acg aaa gag cgt     1008
Ser Val Lys Met Gln Asp Pro Gln Phe Ala Gly Gln Thr Lys Glu Arg
                325                 330                 335 ctc tct tcg cgt caa tgc gcg gca ttc gtt tct ggc gtg gtg aaa gat     1056
Leu Ser Ser Arg Gln Cys Ala Ala Phe Val Ser Gly Val Val Lys Asp
            340                 345                 350 gcc ttt atc ctg tgg ctg aac cag aac gtt cag gcg gct gaa ctg ctg     1104
Ala Phe Ile Leu Trp Leu Asn Gln Asn Val Gln Ala Ala Glu Leu Leu
        355                 360                 365 gcg gag atg gcg att tcc agc gcc cag cgc cgt atg cgt gcg gcc aaa     1152
Ala Glu Met Ala Ile Ser Ser Ala Gln Arg Arg Met Arg Ala Ala Lys
    370                 375                 380 aaa gtg gtg cgt aaa aag ctg acc agc ggc ccg gcg ttg cct ggc aaa     1200
Lys Val Val Arg Lys Lys Leu Thr Ser Gly Pro Ala Leu Pro Gly Lys
385                 390                 395                 400 ctg gct gat tgt acc gcg cag gac ctt aac cgt acc gag ctg ttc ctt     1248
Leu Ala Asp Cys Thr Ala Gln Asp Leu Asn Arg Thr Glu Leu Phe Leu
                405                 410                 415 gtg gaa ggt gac tcc gca ggc gga tct gcc aag cag gcg cgc gat cgc     1296
Val Glu Gly Asp Ser Ala Gly Gly Ser Ala Lys Gln Ala Arg Asp Arg
            420                 425                 430 gaa tat cag gcg atc atg cca ctg aaa ggt aag atc ctt aac acc tgg     1344
Glu Tyr Gln Ala Ile Met Pro Leu Lys Gly Lys Ile Leu Asn Thr Trp
        435                 440                 445 gaa gtc tct tcc gac gaa gtg ctg gct tcg cag gaa gtg cac gat att     1392
Glu Val Ser Ser Asp Glu Val Leu Ala Ser Gln Glu Val His Asp Ile
    450                 455                 460 tcg gta gcg atc ggt atc gat cct gac agc gac gat ctg agc cag ctt     1440
Ser Val Ala Ile Gly Ile Asp Pro Asp Ser Asp Asp Leu Ser Gln Leu
465                 470                 475                 480 cgt tat ggc aaa atc tgt atc ctc gcg gat gcg gac tct gat ggt ctg     1488
Arg Tyr Gly Lys Ile Cys Ile Leu Ala Asp Ala Asp Ser Asp Gly Leu
                485                 490                 495 cac att gcc acg ctg ctc tgc gct ttg ttc gta aaa cat ttc cgc gcg     1536
His Ile Ala Thr Leu Leu Cys Ala Leu Phe Val Lys His Phe Arg Ala
            500                 505                 510 ttg gtg aaa cac ggt cac gtt tac gtc gca ctg cca ccg ctc tac cgt     1584
Leu Val Lys His Gly His Val Tyr Val Ala Leu Pro Pro Leu Tyr Arg
        515                 520                 525 att gat ctc ggg aaa gag gtt tat tac gcg ctg acg gaa gaa gag aaa     1632
Ile Asp Leu Gly Lys Glu Val Tyr Tyr Ala Leu Thr Glu Glu Glu Lys
    530                 535                 540
```

```
gag ggc gta ctt gag caa tta aaa cgc aag aaa ggc aag ccg aac gtc    1680
Glu Gly Val Leu Glu Gln Leu Lys Arg Lys Lys Gly Lys Pro Asn Val
545                 550                 555                 560 cag cgt ttt aaa ggt ctg ggg gaa atg aac ccg atg caa ttg cgc gaa    1728
Gln Arg Phe Lys Gly Leu Gly Glu Met Asn Pro Met Gln Leu Arg Glu
                565                 570                 575 acc acg ctt gat ccg aac act cgc cgt ctg gtg cag ttg act atc gat    1776
Thr Thr Leu Asp Pro Asn Thr Arg Arg Leu Val Gln Leu Thr Ile Asp
            580                 585                 590 gat gaa gac gat cag cgt act gac gcg atg atg gat atg ctg ctg gcg    1824
Asp Glu Asp Asp Gln Arg Thr Asp Ala Met Met Asp Met Leu Leu Ala
        595                 600                 605 aag aaa cgc tcg gaa gat cgc cgc aac tgg ttg caa gag aaa ggc gac    1872
Lys Lys Arg Ser Glu Asp Arg Arg Asn Trp Leu Gln Glu Lys Gly Asp
610                 615                 620 atg gcg gag att gag gtt taa                                        1893
Met Ala Glu Ile Glu Val
625                 630

<210> SEQ ID NO 32
<211> LENGTH: 630
<212> TYPE: PRT
<213> ORGANISM: Escherichia coli

<400> SEQUENCE: 32

Met Thr Gln Thr Tyr Asn Ala Asp Ala Ile Glu Val Leu Thr Gly Leu
1               5                   10                  15

Glu Pro Val Arg Arg Pro Gly Met Tyr Thr Asp Thr Thr Arg Pro
            20                  25                  30

Asn His Leu Gly Gln Glu Val Ile Asp Asn Ser Val Asp Glu Ala Leu
        35                  40                  45

Ala Gly His Ala Lys Arg Val Asp Val Ile Leu His Ala Asp Gln Ser
    50                  55                  60

Leu Glu Val Ile Asp Asp Gly Arg Gly Met Pro Val Asp Ile His Pro
65                  70                  75                  80

Glu Glu Gly Val Pro Ala Val Glu Leu Ile Leu Cys Arg Leu His Ala
                85                  90                  95

Gly Gly Lys Phe Ser Asn Lys Asn Tyr Gln Phe Ser Gly Gly Leu His
            100                 105                 110

Gly Val Gly Ile Ser Val Val Asn Ala Leu Ser Lys Arg Val Glu Val
        115                 120                 125

Asn Val Arg Arg Asp Gly Gln Val Tyr Asn Ile Ala Phe Glu Asn Gly
    130                 135                 140

Glu Lys Val Gln Asp Leu Gln Val Val Gly Thr Cys Gly Lys Arg Asn
145                 150                 155                 160

Thr Gly Thr Ser Val His Phe Trp Pro Asp Glu Thr Phe Phe Asp Ser
                165                 170                 175

Pro Arg Phe Ser Val Ser Arg Leu Thr His Val Leu Lys Ala Lys Ala
            180                 185                 190

Val Leu Cys Pro Gly Val Glu Ile Thr Phe Lys Asp Glu Ile Asn Asn
        195                 200                 205

Thr Glu Gln Arg Trp Cys Tyr Gln Asp Gly Leu Asn Asp Tyr Leu Ala
    210                 215                 220

Glu Ala Val Asn Gly Leu Pro Thr Leu Pro Glu Lys Pro Phe Ile Gly
225                 230                 235                 240

Asn Phe Ala Gly Asp Thr Glu Ala Val Asp Trp Ala Leu Leu Trp Leu
                245                 250                 255
```

```
Pro Glu Gly Gly Glu Leu Leu Thr Glu Ser Tyr Val Asn Leu Ile Pro
            260                 265                 270

Thr Met Gln Gly Gly Thr His Val Asn Gly Leu Arg Gln Gly Leu Leu
            275                 280                 285

Asp Ala Met Arg Glu Phe Cys Glu Tyr Arg Asn Ile Leu Pro Arg Gly
290                 295                 300

Val Lys Leu Ser Ala Glu Asp Ile Trp Asp Arg Cys Ala Tyr Val Leu
305                 310                 315                 320

Ser Val Lys Met Gln Asp Pro Gln Phe Ala Gly Gln Thr Lys Glu Arg
                325                 330                 335

Leu Ser Ser Arg Gln Cys Ala Ala Phe Val Ser Gly Val Val Lys Asp
            340                 345                 350

Ala Phe Ile Leu Trp Leu Asn Gln Asn Val Gln Ala Ala Glu Leu Leu
        355                 360                 365

Ala Glu Met Ala Ile Ser Ser Ala Gln Arg Arg Met Arg Ala Ala Lys
    370                 375                 380

Lys Val Val Arg Lys Lys Leu Thr Ser Gly Pro Ala Leu Pro Gly Lys
385                 390                 395                 400

Leu Ala Asp Cys Thr Ala Gln Asp Leu Asn Arg Thr Glu Leu Phe Leu
                405                 410                 415

Val Glu Gly Asp Ser Ala Gly Gly Ser Ala Lys Gln Ala Arg Asp Arg
            420                 425                 430

Glu Tyr Gln Ala Ile Met Pro Leu Lys Gly Lys Ile Leu Asn Thr Trp
        435                 440                 445

Glu Val Ser Ser Asp Glu Val Leu Ala Ser Gln Glu Val His Asp Ile
    450                 455                 460

Ser Val Ala Ile Gly Ile Asp Pro Asp Ser Asp Asp Leu Ser Gln Leu
465                 470                 475                 480

Arg Tyr Gly Lys Ile Cys Ile Leu Ala Asp Ala Asp Ser Asp Gly Leu
                485                 490                 495

His Ile Ala Thr Leu Leu Cys Ala Leu Phe Val Lys His Phe Arg Ala
            500                 505                 510

Leu Val Lys His Gly His Val Tyr Val Ala Leu Pro Pro Leu Tyr Arg
        515                 520                 525

Ile Asp Leu Gly Lys Glu Val Tyr Tyr Ala Leu Thr Glu Glu Glu Lys
    530                 535                 540

Glu Gly Val Leu Glu Gln Leu Lys Arg Lys Gly Lys Pro Asn Val
545                 550                 555                 560

Gln Arg Phe Lys Gly Leu Gly Glu Met Asn Pro Met Gln Leu Arg Glu
                565                 570                 575

Thr Thr Leu Asp Pro Asn Thr Arg Arg Leu Val Gln Leu Thr Ile Asp
            580                 585                 590

Asp Glu Asp Asp Gln Arg Thr Asp Ala Met Met Asp Met Leu Leu Ala
        595                 600                 605

Lys Lys Arg Ser Glu Asp Arg Arg Asn Trp Leu Gln Glu Lys Gly Asp
    610                 615                 620

Met Ala Glu Ile Glu Val
625                 630

<210> SEQ ID NO 33
<211> LENGTH: 40
<212> TYPE: DNA
<213> ORGANISM: Artificial Sequence
<220> FEATURE:
<223> OTHER INFORMATION: Synthetic DNA
```

-continued

```
<400> SEQUENCE: 33
gcggtgatag cgaagagtaa gaattactaa cttaaaccat                              40

<210> SEQ ID NO 34
<211> LENGTH: 29
<212> TYPE: DNA
<213> ORGANISM: Artificial Sequence
<220> FEATURE:
<223> OTHER INFORMATION: Synthetic DNA

<400> SEQUENCE: 34
tttgtcgact taaacctcaa tctccgcca                                         29

<210> SEQ ID NO 35
<211> LENGTH: 2991
<212> TYPE: DNA
<213> ORGANISM: Corynebacterium glutamicum
<220> FEATURE:
<221> NAME/KEY: CDS
<222> LOCATION: (1)..(2991)

<400> SEQUENCE: 35
```

| | | | | | | | | | | | | | | | | |
|---|---|---|---|---|---|---|---|---|---|---|---|---|---|---|---|---|
| gtg | gca | gat | acc | gca | ggc | acc | aca | gga | tcg | aaa | aag | aag | tac | ttg | gtg | 48 |
| Val | Ala | Asp | Thr | Ala | Gly | Thr | Thr | Gly | Ser | Lys | Lys | Lys | Tyr | Leu | Val | |
| 1 | | | | 5 | | | | | 10 | | | | | 15 | | |

| atc | gtc | gag | tcg | gcg | acc | aag | gct | aaa | aag | att | cag | cct | tac | ctt | ggc | 96 |
|---|---|---|---|---|---|---|---|---|---|---|---|---|---|---|---|---|
| Ile | Val | Glu | Ser | Ala | Thr | Lys | Ala | Lys | Lys | Ile | Gln | Pro | Tyr | Leu | Gly | |
| | | | 20 | | | | | 25 | | | | | 30 | | | |

| aac | gac | tac | atc | gtc | gag | gcc | tcc | gtt | ggt | cat | att | cgt | gat | ctg | cca | 144 |
|---|---|---|---|---|---|---|---|---|---|---|---|---|---|---|---|---|
| Asn | Asp | Tyr | Ile | Val | Glu | Ala | Ser | Val | Gly | His | Ile | Arg | Asp | Leu | Pro | |
| | | | 35 | | | | 40 | | | | | 45 | | | | |

| cgt | ggc | gct | gct | gac | atc | cct | gca | aag | tac | aag | aag | gag | cct | tgg | gct | 192 |
|---|---|---|---|---|---|---|---|---|---|---|---|---|---|---|---|---|
| Arg | Gly | Ala | Ala | Asp | Ile | Pro | Ala | Lys | Tyr | Lys | Lys | Glu | Pro | Trp | Ala | |
| | 50 | | | | | 55 | | | | | 60 | | | | | |

| cgt | ctt | ggt | gtg | gac | acc | gat | cgc | ggt | ttc | gcg | ccg | ctt | tat | gtg | gtg | 240 |
|---|---|---|---|---|---|---|---|---|---|---|---|---|---|---|---|---|
| Arg | Leu | Gly | Val | Asp | Thr | Asp | Arg | Gly | Phe | Ala | Pro | Leu | Tyr | Val | Val | |
| 65 | | | | | 70 | | | | | 75 | | | | | 80 | |

| agc | ccc | gat | aaa | aag | aag | aag | gtc | gct | gac | ctc | aag | gcg | aag | ctc | aag | 288 |
|---|---|---|---|---|---|---|---|---|---|---|---|---|---|---|---|---|
| Ser | Pro | Asp | Lys | Lys | Lys | Lys | Val | Ala | Asp | Leu | Lys | Ala | Lys | Leu | Lys | |
| | | | | 85 | | | | | 90 | | | | | 95 | | |

| ctc | gtt | gat | gag | ttg | ctg | ctg | gca | aca | gac | ccc | gac | cgt | gag | ggc | gag | 336 |
|---|---|---|---|---|---|---|---|---|---|---|---|---|---|---|---|---|
| Leu | Val | Asp | Glu | Leu | Leu | Leu | Ala | Thr | Asp | Pro | Asp | Arg | Glu | Gly | Glu | |
| | | | 100 | | | | | 105 | | | | | 110 | | | |

| gcg | att | gcg | tgg | cat | ttg | ctt | gag | gtg | ttg | aag | ccg | act | gtt | cct | gtg | 384 |
|---|---|---|---|---|---|---|---|---|---|---|---|---|---|---|---|---|
| Ala | Ile | Ala | Trp | His | Leu | Leu | Glu | Val | Leu | Lys | Pro | Thr | Val | Pro | Val | |
| | | 115 | | | | | 120 | | | | | 125 | | | | |

| cgt | cgc | atg | gtg | ttc | aat | gag | atc | acg | aag | cct | gcc | att | ttg | gct | gcg | 432 |
|---|---|---|---|---|---|---|---|---|---|---|---|---|---|---|---|---|
| Arg | Arg | Met | Val | Phe | Asn | Glu | Ile | Thr | Lys | Pro | Ala | Ile | Leu | Ala | Ala | |
| | 130 | | | | | 135 | | | | | 140 | | | | | |

| gcg | gaa | aac | act | cgt | gag | ctg | gat | gag | aac | ctg | gtg | gat | gcg | cag | gaa | 480 |
|---|---|---|---|---|---|---|---|---|---|---|---|---|---|---|---|---|
| Ala | Glu | Asn | Thr | Arg | Glu | Leu | Asp | Glu | Asn | Leu | Val | Asp | Ala | Gln | Glu | |
| 145 | | | | | 150 | | | | | 155 | | | | | 160 | |

| act | cgt | cgt | att | ctg | gac | cgt | ttg | tac | ggc | tat | gaa | gtc | tct | cct | gtg | 528 |
|---|---|---|---|---|---|---|---|---|---|---|---|---|---|---|---|---|
| Thr | Arg | Arg | Ile | Leu | Asp | Arg | Leu | Tyr | Gly | Tyr | Glu | Val | Ser | Pro | Val | |
| | | | 165 | | | | | 170 | | | | | 175 | | | |

| ctg | tgg | aaa | aag | gtc | atg | ccg | agg | ttg | tcg | gcg | ggc | cgt | gtg | cag | tcg | 576 |
|---|---|---|---|---|---|---|---|---|---|---|---|---|---|---|---|---|
| Leu | Trp | Lys | Lys | Val | Met | Pro | Arg | Leu | Ser | Ala | Gly | Arg | Val | Gln | Ser | |
| | | | 180 | | | | | 185 | | | | | 190 | | | |

| gtg | gca | acc | cgt | gtg | att | gtt | gag | cgg | gag | cgc | gag | cgc | atg | gcg | ttc | 624 |
|---|---|---|---|---|---|---|---|---|---|---|---|---|---|---|---|---|
| Val | Ala | Thr | Arg | Val | Ile | Val | Glu | Arg | Glu | Arg | Glu | Arg | Met | Ala | Phe | |
| | | 195 | | | | | 200 | | | | | 205 | | | | |

| gtg | tcg | gcg | gat | tat | tgg | gat | ctg | tcg | gcg | gag | ttt | aat | gcg | cgt | gaa | 672 |
|---|---|---|---|---|---|---|---|---|---|---|---|---|---|---|---|---|

```
                                              -continued

Val Ser Ala Asp Tyr Trp Asp Leu Ser Ala Glu Phe Asn Ala Arg Glu
    210                 215                 220 aac ggc aag gcg gat tcg gat aac ccg tcg tcg ttt act gcg cgt ttg      720
Asn Gly Lys Ala Asp Ser Asp Asn Pro Ser Ser Phe Thr Ala Arg Leu
225                 230                 235                 240 tcc acg att gat gga aac cgt gtt gct caa ggc cgt gat ttt aat gat      768
Ser Thr Ile Asp Gly Asn Arg Val Ala Gln Gly Arg Asp Phe Asn Asp
                245                 250                 255 cgg gga gag ctg acc tcg gag gct gtc gtc gtc gat aag cag cgt gct      816
Arg Gly Glu Leu Thr Ser Glu Ala Val Val Val Asp Lys Gln Arg Ala
            260                 265                 270 gag gcg tta gcc gag gct ttg gaa ggc cag gaa atg gcc gtc gtt ggg      864
Glu Ala Leu Ala Glu Ala Leu Glu Gly Gln Glu Met Ala Val Val Gly
        275                 280                 285 gtc gag gaa aag ccg tac acc cgt cgc cct tat gcg ccg ttt atg acc      912
Val Glu Glu Lys Pro Tyr Thr Arg Arg Pro Tyr Ala Pro Phe Met Thr
    290                 295                 300 tct acg ctg cag caa gag tct ggc cgc aag ctg cat tac act tct gag      960
Ser Thr Leu Gln Gln Glu Ser Gly Arg Lys Leu His Tyr Thr Ser Glu
305                 310                 315                 320 cgc acg atg cgt att gcg cag cgc ttg tat gaa aac ggc cat atc act     1008
Arg Thr Met Arg Ile Ala Gln Arg Leu Tyr Glu Asn Gly His Ile Thr
                325                 330                 335 tat atg cgt act gac tcg acc tcg ttg tcg gag cag ggc atg aag gct     1056
Tyr Met Arg Thr Asp Ser Thr Ser Leu Ser Glu Gln Gly Met Lys Ala
            340                 345                 350 gcg cgc gat cag gcg ttg gag ctg tac ggt gcg gaa tat gtt tcg ccg     1104
Ala Arg Asp Gln Ala Leu Glu Leu Tyr Gly Ala Glu Tyr Val Ser Pro
        355                 360                 365 agc cca cgt acc tat gac cgc aag gtg aag aac tcc cag gag gcc cac     1152
Ser Pro Arg Thr Tyr Asp Arg Lys Val Lys Asn Ser Gln Glu Ala His
    370                 375                 380 gag gcg att cgc cca gct ggt gaa act ttt gcg acc ccg ggc cag ctg     1200
Glu Ala Ile Arg Pro Ala Gly Glu Thr Phe Ala Thr Pro Gly Gln Leu
385                 390                 395                 400 cat ggc cag ttg gat gcg gaa gaa ttt aag ctc tat gag ctg att tgg     1248
His Gly Gln Leu Asp Ala Glu Glu Phe Lys Leu Tyr Glu Leu Ile Trp
                405                 410                 415 cag cgc act gtg gcc tcc cag atg gcc gat gcc aag ggc acg tcc atg     1296
Gln Arg Thr Val Ala Ser Gln Met Ala Asp Ala Lys Gly Thr Ser Met
            420                 425                 430 aag gtc acc atc ggt ggc acc gcg aag acc ggc gag aag act gag ttc     1344
Lys Val Thr Ile Gly Gly Thr Ala Lys Thr Gly Glu Lys Thr Glu Phe
        435                 440                 445 aac gcg acc ggc cgc acg ctg act ttc cct ggc ttc ctg cgc gct tac     1392
Asn Ala Thr Gly Arg Thr Leu Thr Phe Pro Gly Phe Leu Arg Ala Tyr
    450                 455                 460 gtg gaa acc acc cgc acc gcc gat ggc cgc gac gta gct gac aac gcc     1440
Val Glu Thr Thr Arg Thr Ala Asp Gly Arg Asp Val Ala Asp Asn Ala
465                 470                 475                 480 gaa aag cgt ctg cca ctg ctg tct gag ggc gat ctg ctc aag gtt ttg     1488
Glu Lys Arg Leu Pro Leu Leu Ser Glu Gly Asp Leu Leu Lys Val Leu
                485                 490                 495 agc atc gaa gcc gat ggt cac agc acc aat cca cct gcg cgc tac aca     1536
Ser Ile Glu Ala Asp Gly His Ser Thr Asn Pro Pro Ala Arg Tyr Thr
            500                 505                 510 gag gcg tcg ctg gtg aag aag atg gaa gat ctg ggc atc ggc cgt cct     1584
Glu Ala Ser Leu Val Lys Lys Met Glu Asp Leu Gly Ile Gly Arg Pro
        515                 520                 525 tcc act tat gca tcg atc att aag acg att cag gat cga ggc tac gtt     1632
```

-continued

| | | |
|---|---|---|
| Ser Thr Tyr Ala Ser Ile Ile Lys Thr Ile Gln Asp Arg Gly Tyr Val<br>530 535 540 | | |
| tat tcg cgt ggc aat gcg ctg gtg ccg tcc tgg gtc gcg ttc gcc gtg<br>Tyr Ser Arg Gly Asn Ala Leu Val Pro Ser Trp Val Ala Phe Ala Val<br>545 550 555 560 | 1680 | |
| gtc gga ttg ctt gaa gcc aac ttc acc tcg ctg gtg gat tac gat ttc<br>Val Gly Leu Leu Glu Ala Asn Phe Thr Ser Leu Val Asp Tyr Asp Phe<br>565 570 575 | 1728 | |
| acc tcc tcc atg gaa gat gag ctg gac aac atc gcc gca ggt cgc gag<br>Thr Ser Ser Met Glu Asp Glu Leu Asp Asn Ile Ala Ala Gly Arg Glu<br>580 585 590 | 1776 | |
| ggc cgc acg gag tgg ctc aac ggt ttc tac ttc ggc gat gcc gaa gcg<br>Gly Arg Thr Glu Trp Leu Asn Gly Phe Tyr Phe Gly Asp Ala Glu Ala<br>595 600 605 | 1824 | |
| gat cag tcc atg gct gaa tca gtt gcc cgc cag ggc ggt ttg aag gcg<br>Asp Gln Ser Met Ala Glu Ser Val Ala Arg Gln Gly Gly Leu Lys Ala<br>610 615 620 | 1872 | |
| ctt gtc gac gcg aac ctg gag cac atc gac gcg cgt tca gta aac tca<br>Leu Val Asp Ala Asn Leu Glu His Ile Asp Ala Arg Ser Val Asn Ser<br>625 630 635 640 | 1920 | |
| ctc aag ctt ttc gac gac gcc gaa ggc cgt gcc gtg aac gtt cga gtc<br>Leu Lys Leu Phe Asp Asp Ala Glu Gly Arg Ala Val Asn Val Arg Val<br>645 650 655 | 1968 | |
| gga cgc tac ggt ccg tac atc gag cgc atc gtg ggc acc acg gcg gaa<br>Gly Arg Tyr Gly Pro Tyr Ile Glu Arg Ile Val Gly Thr Thr Ala Glu<br>660 665 670 | 2016 | |
| ggc gag cca gaa ttt cag cgc gcc aac cta cct gag gaa acc acg cct<br>Gly Glu Pro Glu Phe Gln Arg Ala Asn Leu Pro Glu Glu Thr Thr Pro<br>675 680 685 | 2064 | |
| gat gag ctg acc ctc gag gtc gct gag aag ctc ttc gct acc cca caa<br>Asp Glu Leu Thr Leu Glu Val Ala Glu Lys Leu Phe Ala Thr Pro Gln<br>690 695 700 | 2112 | |
| ggt gga cgt gaa ctg ggc att aac cca gca aac ggt cgc atg gtg gtg<br>Gly Gly Arg Glu Leu Gly Ile Asn Pro Ala Asn Gly Arg Met Val Val<br>705 710 715 720 | 2160 | |
| gct aag gaa ggc cgc ttt ggt cca tac gtg atc gag cag gtc acg gac<br>Ala Lys Glu Gly Arg Phe Gly Pro Tyr Val Ile Glu Gln Val Thr Asp<br>725 730 735 | 2208 | |
| tca gag cgc gct ggc gcc gaa gcc caa gca gaa gaa gtc gtt gca gcg<br>Ser Glu Arg Ala Gly Ala Glu Ala Gln Ala Glu Glu Val Val Ala Ala<br>740 745 750 | 2256 | |
| gaa cga aaa gct gaa gac gaa caa cgt gcc acc gat gga atg cga ccc<br>Glu Arg Lys Ala Glu Asp Glu Gln Arg Ala Thr Asp Gly Met Arg Pro<br>755 760 765 | 2304 | |
| aag aac tgg gaa acc aag act gcc gca aac cag aag gaa aag cgc atc<br>Lys Asn Trp Glu Thr Lys Thr Ala Ala Asn Gln Lys Glu Lys Arg Ile<br>770 775 780 | 2352 | |
| aac cag ctg gtt gag gaa aac ctc aag cca gcg acc gca tcc ctg ttc<br>Asn Gln Leu Val Glu Glu Asn Leu Lys Pro Ala Thr Ala Ser Leu Phe<br>785 790 795 800 | 2400 | |
| agc ggc atg gaa cct gca acc gtg acc ctg gaa gaa gcc ctc aag ctg<br>Ser Gly Met Glu Pro Ala Thr Val Thr Leu Glu Glu Ala Leu Lys Leu<br>805 810 815 | 2448 | |
| ctg tcc ctg cca cgc gaa gta ggt gtc gat cct tcc gac aac gaa gtg<br>Leu Ser Leu Pro Arg Glu Val Gly Val Asp Pro Ser Asp Asn Glu Val<br>820 825 830 | 2496 | |
| atc acc gct caa aac gga cga tac ggc cct tat ctg aag aag ggt agc<br>Ile Thr Ala Gln Asn Gly Arg Tyr Gly Pro Tyr Leu Lys Lys Gly Ser<br>835 840 845 | 2544 | |
| gac tcc cgt tcc ctc aac agc gaa gag cag atc ttc acc gtc act ttg<br> | 2592 | |

```
                 Asp Ser Arg Ser Leu Asn Ser Glu Glu Gln Ile Phe Thr Val Thr Leu
                     850                 855                 860 gat gag gct cgc cgc atc tac gcc gaa cca aag cgt cgt gga cgc gcc      2640
Asp Glu Ala Arg Arg Ile Tyr Ala Glu Pro Lys Arg Arg Gly Arg Ala
865                 870                 875                 880 gct gct cag cca cca ctg aag caa ctt ggc gac aat gac gtt tcc ggc      2688
Ala Ala Gln Pro Pro Leu Lys Gln Leu Gly Asp Asn Asp Val Ser Gly
                885                 890                 895 aaa cca atg acc gtc aag gac gga cgt ttc ggc cca tac gtc acc gac      2736
Lys Pro Met Thr Val Lys Asp Gly Arg Phe Gly Pro Tyr Val Thr Asp
            900                 905                 910 ggc acc acc aac gcg tca ctg cgc aag ggc gat gtt cca gag tcc ctg      2784
Gly Thr Thr Asn Ala Ser Leu Arg Lys Gly Asp Val Pro Glu Ser Leu
        915                 920                 925 acc gat gcg cgt gcc aac gag tta ctt tcc gag cgt cgt gcc aag gaa      2832
Thr Asp Ala Arg Ala Asn Glu Leu Leu Ser Glu Arg Arg Ala Lys Glu
    930                 935                 940 gca gca gat ggc gga gct cct gcg aag aag acg tcc act aaa aag act      2880
Ala Ala Asp Gly Gly Ala Pro Ala Lys Lys Thr Ser Thr Lys Lys Thr
945                 950                 955                 960 gca gcc aag aag acc acg gct aaa aag aca aca gct aag aaa acc gtg      2928
Ala Ala Lys Lys Thr Thr Ala Lys Lys Thr Thr Ala Lys Lys Thr Val
                965                 970                 975 agg aag gct ccg ccg aaa acc acc aaa aac gtg gtg aag gcc ggc gct      2976
Arg Lys Ala Pro Pro Lys Thr Thr Lys Asn Val Val Lys Ala Gly Ala
            980                 985                 990 aag aag aag tcc taa                                                  2991
Lys Lys Lys Ser
        995

<210> SEQ ID NO 36
<211> LENGTH: 996
<212> TYPE: PRT
<213> ORGANISM: Corynebacterium glutamicum

<400> SEQUENCE: 36

Val Ala Asp Thr Ala Gly Thr Thr Gly Ser Lys Lys Lys Tyr Leu Val
1               5                   10                  15

Ile Val Glu Ser Ala Thr Lys Ala Lys Lys Ile Gln Pro Tyr Leu Gly
                20                  25                  30

Asn Asp Tyr Ile Val Glu Ala Ser Val Gly His Ile Arg Asp Leu Pro
            35                  40                  45

Arg Gly Ala Ala Asp Ile Pro Ala Lys Tyr Lys Lys Glu Pro Trp Ala
        50                  55                  60

Arg Leu Gly Val Asp Thr Asp Arg Gly Phe Ala Pro Leu Tyr Val Val
65                  70                  75                  80

Ser Pro Asp Lys Lys Lys Val Ala Asp Leu Lys Ala Lys Leu Lys
                85                  90                  95

Leu Val Asp Glu Leu Leu Leu Ala Thr Asp Pro Asp Arg Glu Gly Glu
            100                 105                 110

Ala Ile Ala Trp His Leu Leu Glu Val Leu Lys Pro Thr Val Pro Val
        115                 120                 125

Arg Arg Met Val Phe Asn Glu Ile Thr Lys Pro Ala Ile Leu Ala Ala
    130                 135                 140

Ala Glu Asn Thr Arg Glu Leu Asp Glu Asn Leu Val Asp Ala Gln Glu
145                 150                 155                 160

Thr Arg Arg Ile Leu Asp Arg Leu Tyr Gly Tyr Glu Val Ser Pro Val
                165                 170                 175
```

```
Leu Trp Lys Lys Val Met Pro Arg Leu Ser Ala Gly Arg Val Gln Ser
            180                 185                 190

Val Ala Thr Arg Val Ile Val Glu Arg Glu Arg Glu Arg Met Ala Phe
        195                 200                 205

Val Ser Ala Asp Tyr Trp Asp Leu Ser Ala Glu Phe Asn Ala Arg Glu
    210                 215                 220

Asn Gly Lys Ala Asp Ser Asp Asn Pro Ser Ser Phe Thr Ala Arg Leu
225                 230                 235                 240

Ser Thr Ile Asp Gly Asn Arg Val Ala Gln Gly Arg Asp Phe Asn Asp
                245                 250                 255

Arg Gly Glu Leu Thr Ser Glu Ala Val Val Asp Lys Gln Arg Ala
            260                 265                 270

Glu Ala Leu Ala Glu Ala Leu Glu Gly Gln Glu Met Ala Val Val Gly
        275                 280                 285

Val Glu Glu Lys Pro Tyr Thr Arg Arg Pro Tyr Ala Pro Phe Met Thr
    290                 295                 300

Ser Thr Leu Gln Gln Glu Ser Gly Arg Lys Leu His Tyr Thr Ser Glu
305                 310                 315                 320

Arg Thr Met Arg Ile Ala Gln Arg Leu Tyr Glu Asn Gly His Ile Thr
                325                 330                 335

Tyr Met Arg Thr Asp Ser Thr Ser Leu Ser Glu Gln Gly Met Lys Ala
            340                 345                 350

Ala Arg Asp Gln Ala Leu Glu Leu Tyr Gly Ala Glu Tyr Val Ser Pro
        355                 360                 365

Ser Pro Arg Thr Tyr Asp Arg Lys Val Lys Asn Ser Gln Glu Ala His
    370                 375                 380

Glu Ala Ile Arg Pro Ala Gly Glu Thr Phe Ala Thr Pro Gly Gln Leu
385                 390                 395                 400

His Gly Gln Leu Asp Ala Glu Glu Phe Lys Leu Tyr Glu Leu Ile Trp
                405                 410                 415

Gln Arg Thr Val Ala Ser Gln Met Ala Asp Ala Lys Gly Thr Ser Met
            420                 425                 430

Lys Val Thr Ile Gly Gly Thr Ala Lys Thr Gly Glu Lys Thr Glu Phe
        435                 440                 445

Asn Ala Thr Gly Arg Thr Leu Thr Phe Pro Gly Phe Leu Arg Ala Tyr
    450                 455                 460

Val Glu Thr Thr Arg Thr Ala Asp Gly Arg Asp Val Ala Asp Asn Ala
465                 470                 475                 480

Glu Lys Arg Leu Pro Leu Leu Ser Glu Gly Asp Leu Leu Lys Val Leu
                485                 490                 495

Ser Ile Glu Ala Asp Gly His Ser Thr Asn Pro Pro Ala Arg Tyr Thr
            500                 505                 510

Glu Ala Ser Leu Val Lys Lys Met Glu Asp Leu Gly Ile Gly Arg Pro
        515                 520                 525

Ser Thr Tyr Ala Ser Ile Ile Lys Thr Ile Gln Asp Arg Gly Tyr Val
    530                 535                 540

Tyr Ser Arg Gly Asn Ala Leu Val Pro Ser Trp Val Ala Phe Ala Val
545                 550                 555                 560

Val Gly Leu Leu Glu Ala Asn Phe Thr Ser Leu Val Asp Tyr Asp Phe
                565                 570                 575

Thr Ser Ser Met Glu Asp Glu Leu Asp Asn Ile Ala Ala Gly Arg Glu
            580                 585                 590

Gly Arg Thr Glu Trp Leu Asn Gly Phe Tyr Phe Gly Asp Ala Glu Ala
        595                 600                 605
```

```
Asp Gln Ser Met Ala Glu Ser Val Ala Arg Gln Gly Gly Leu Lys Ala
    610                 615                 620
Leu Val Asp Ala Asn Leu Glu His Ile Asp Ala Arg Ser Val Asn Ser
625                 630                 635                 640
Leu Lys Leu Phe Asp Asp Ala Glu Gly Arg Ala Val Asn Val Arg Val
                645                 650                 655
Gly Arg Tyr Gly Pro Tyr Ile Glu Arg Ile Val Gly Thr Thr Ala Glu
                660                 665                 670
Gly Glu Pro Glu Phe Gln Arg Ala Asn Leu Pro Glu Thr Thr Pro
            675                 680                 685
Asp Glu Leu Thr Leu Glu Val Ala Glu Lys Leu Phe Ala Thr Pro Gln
            690                 695                 700
Gly Gly Arg Glu Leu Gly Ile Asn Pro Ala Asn Gly Arg Met Val Val
705                 710                 715                 720
Ala Lys Glu Gly Arg Phe Gly Pro Tyr Val Ile Glu Gln Val Thr Asp
                725                 730                 735
Ser Glu Arg Ala Gly Ala Glu Ala Gln Ala Glu Val Val Ala Ala
                740                 745                 750
Glu Arg Lys Ala Glu Asp Gln Arg Ala Thr Asp Gly Met Arg Pro
            755                 760                 765
Lys Asn Trp Glu Thr Lys Thr Ala Ala Asn Gln Lys Glu Lys Arg Ile
770                 775                 780
Asn Gln Leu Val Glu Glu Asn Leu Lys Pro Ala Thr Ala Ser Leu Phe
785                 790                 795                 800
Ser Gly Met Glu Pro Ala Thr Val Thr Leu Glu Glu Ala Leu Lys Leu
                805                 810                 815
Leu Ser Leu Pro Arg Glu Val Gly Val Asp Pro Ser Asp Asn Glu Val
                820                 825                 830
Ile Thr Ala Gln Asn Gly Arg Tyr Gly Pro Tyr Leu Lys Lys Gly Ser
            835                 840                 845
Asp Ser Arg Ser Leu Asn Ser Glu Glu Gln Ile Phe Thr Val Thr Leu
            850                 855                 860
Asp Glu Ala Arg Arg Ile Tyr Ala Glu Pro Lys Arg Gly Arg Ala
865                 870                 875                 880
Ala Ala Gln Pro Pro Leu Lys Gln Leu Gly Asp Asn Asp Val Ser Gly
                885                 890                 895
Lys Pro Met Thr Val Lys Asp Gly Arg Phe Gly Pro Tyr Val Thr Asp
                900                 905                 910
Gly Thr Thr Asn Ala Ser Leu Arg Lys Gly Asp Val Pro Glu Ser Leu
            915                 920                 925
Thr Asp Ala Arg Ala Asn Glu Leu Leu Ser Glu Arg Arg Ala Lys Glu
            930                 935                 940
Ala Ala Asp Gly Gly Ala Pro Ala Lys Lys Thr Ser Thr Lys Lys Thr
945                 950                 955                 960
Ala Ala Lys Lys Thr Thr Ala Lys Lys Thr Thr Ala Lys Lys Thr Val
                965                 970                 975
Arg Lys Ala Pro Pro Lys Thr Thr Lys Asn Val Val Lys Ala Gly Ala
                980                 985                 990
Lys Lys Lys Ser
        995

<210> SEQ ID NO 37
<211> LENGTH: 29
<212> TYPE: DNA
```

<213> ORGANISM: Artificial Sequence
<220> FEATURE:
<223> OTHER INFORMATION: Synthetic DNA

<400> SEQUENCE: 37
tttggatcct atgttcttcc cccgcgaag                              29

<210> SEQ ID NO 38
<211> LENGTH: 29
<212> TYPE: DNA
<213> ORGANISM: Artificial Sequence
<220> FEATURE:
<223> OTHER INFORMATION: Synthetic DNA

<400> SEQUENCE: 38
tttggatcct taggacttct tcttagcgc                              29

<210> SEQ ID NO 39
<211> LENGTH: 2280
<212> TYPE: DNA
<213> ORGANISM: Corynebacterium glutamicum
<220> FEATURE:
<221> NAME/KEY: CDS
<222> LOCATION: (1)..(2280)

<400> SEQUENCE: 39

```
ttg aca att gga att ttg acg gag aaa gct tcg gct gcg aaa aac ttt      48
Leu Thr Ile Gly Ile Leu Thr Glu Lys Ala Ser Ala Ala Lys Asn Phe
 1               5                  10                  15 gcg aaa gcc ctc ggt gga ccc tct ggc act tat aac ggc gag aag tac      96
Ala Lys Ala Leu Gly Gly Pro Ser Gly Thr Tyr Asn Gly Glu Lys Tyr
             20                  25                  30 gtt att gct gca gcc agc ggg cac ctt tat gaa ttt gtc gag cca gaa     144
Val Ile Ala Ala Ala Ser Gly His Leu Tyr Glu Phe Val Glu Pro Glu
         35                  40                  45 gag atg gtg cca cca agc tat gcc gat aag atc ggc ggc tac tgg gat     192
Glu Met Val Pro Pro Ser Tyr Ala Asp Lys Ile Gly Gly Tyr Trp Asp
     50                  55                  60 ctg gct aag ctg ccg tgg gat gag acg cag ttt ttg tgg tca cgc gag     240
Leu Ala Lys Leu Pro Trp Asp Glu Thr Gln Phe Leu Trp Ser Arg Glu
 65                  70                  75                  80 caa aag cac ggt gca gct aac acg att gca cgc att aag aaa acc ttg     288
Gln Lys His Gly Ala Ala Asn Thr Ile Ala Arg Ile Lys Lys Thr Leu
                 85                  90                  95 agc agc tgc acc acc att gtg atc gga tca gat att gat ccc acg ggc     336
Ser Ser Cys Thr Thr Ile Val Ile Gly Ser Asp Ile Asp Pro Thr Gly
            100                 105                 110 gaa ggt gat ctg ttg gcg tgg gag att atc gct gag ctg ggg tta gac     384
Glu Gly Asp Leu Leu Ala Trp Glu Ile Ile Ala Glu Leu Gly Leu Asp
        115                 120                 125 acc aag aag att cag cgt atg gaa ttt gtt gat gag gcg ccg gcc tcg     432
Thr Lys Lys Ile Gln Arg Met Glu Phe Val Asp Glu Ala Pro Ala Ser
    130                 135                 140 att cag cag gcg ttt atc aac cgc cgc gat gtg acc tcc atg cat gac     480
Ile Gln Gln Ala Phe Ile Asn Arg Arg Asp Val Thr Ser Met His Asp
145                 150                 155                 160 gag ccc aat tat ctt aag gcg gaa ttc cga tca cgc ttt gat ttg ctg     528
Glu Pro Asn Tyr Leu Lys Ala Glu Phe Arg Ser Arg Phe Asp Leu Leu
                165                 170                 175 tcg atg cag tgg act cgc ggt gcc acc aaa gtg cta gag acc act ggt     576
Ser Met Gln Trp Thr Arg Gly Ala Thr Lys Val Leu Glu Thr Thr Gly
            180                 185                 190 cgg cgt gca gtg ttg cgc aat ggt cgc ctg aaa tct gcc atg gtt gcg     624
```

-continued

```
          Arg Arg Ala Val Leu Arg Asn Gly Arg Leu Lys Ser Ala Met Val Ala
                  195                 200                 205 att gtg ggg cag ggc tta gat gcg tac aac gat tat aaa aag att cct        672
Ile Val Gly Gln Gly Leu Asp Ala Tyr Asn Asp Tyr Lys Lys Ile Pro
210                 215                 220 ttt tat caa aac cgc ttc att gat gat cac ggt gta agt tac gtc aac        720
Phe Tyr Gln Asn Arg Phe Ile Asp Asp His Gly Val Ser Tyr Val Asn
225                 230                 235                 240 ccc gag gaa ccg cgt tat aag act tgc gac gag gta cca cag ctt tat        768
Pro Glu Glu Pro Arg Tyr Lys Thr Cys Asp Glu Val Pro Gln Leu Tyr
                245                 250                 255 aag gct agt gcg gtc gaa tgc tat gag aag agc atg aaa aag acc gcg        816
Lys Ala Ser Ala Val Glu Cys Tyr Glu Lys Ser Met Lys Lys Thr Ala
            260                 265                 270 cca cca cgt cta ctt gac ctg gcg agc ctg tcg gcc ctg ctg tct aaa        864
Pro Pro Arg Leu Leu Asp Leu Ala Ser Leu Ser Ala Leu Leu Ser Lys
        275                 280                 285 gag ggc ttt agc gca aag aac gtg ctt aag act tat cag cag atg tac        912
Glu Gly Phe Ser Ala Lys Asn Val Leu Lys Thr Tyr Gln Gln Met Tyr
290                 295                 300 gag gcg cag gtc gtg tct tat ccg cgt acc gag gat aag acg att acc        960
Glu Ala Gln Val Val Ser Tyr Pro Arg Thr Glu Asp Lys Thr Ile Thr
305                 310                 315                 320 cct gag cag ttt aag gaa cta gcg ccg ttg gtc gat aag atc gcc ggc       1008
Pro Glu Gln Phe Lys Glu Leu Ala Pro Leu Val Asp Lys Ile Ala Gly
                325                 330                 335 ctg gtt ggt gtg aac ccg gct gac ctt acg cac cga cag cca cgg tcc       1056
Leu Val Gly Val Asn Pro Ala Asp Leu Thr His Arg Gln Pro Arg Ser
            340                 345                 350 acg cat gtt aag ccc aag ggt gca cac ggc gcc aac cgt ccg ggt ttg       1104
Thr His Val Lys Pro Lys Gly Ala His Gly Ala Asn Arg Pro Gly Leu
        355                 360                 365 aat gtg ccg acc agt att gca gcg gtg aaa acc acc tac ggt gtg ctc       1152
Asn Val Pro Thr Ser Ile Ala Ala Val Lys Thr Thr Tyr Gly Val Leu
370                 375                 380 gga cag cgc att tat gaa gtg ctc gct aag agc tat ctc acg atg ctg       1200
Gly Gln Arg Ile Tyr Glu Val Leu Ala Lys Ser Tyr Leu Thr Met Leu
385                 390                 395                 400 gca gag gat tac ctc tat gag cac caa aaa ggc cgc gtc gtg gat tac       1248
Ala Glu Asp Tyr Leu Tyr Glu His Gln Lys Gly Arg Val Val Asp Tyr
                405                 410                 415 cca gcg ttt ctc ggt aca gca aat gtg cca aag tcc ttg ggt tgg aaa       1296
Pro Ala Phe Leu Gly Thr Ala Asn Val Pro Lys Ser Leu Gly Trp Lys
            420                 425                 430 ggt att ttc gac gta gac gct gag gct gat gat gat gct gcc ggc agt       1344
Gly Ile Phe Asp Val Asp Ala Glu Ala Asp Asp Asp Ala Ala Gly Ser
        435                 440                 445 gat gca gca cag cag ggg att ggt act cgt gct gag cca gaa gtg ttt       1392
Asp Ala Ala Gln Gln Gly Ile Gly Thr Arg Ala Glu Pro Glu Val Phe
450                 455                 460 gag ggt ttt ccg cag cga cca ccg cat ccg tca atg acg tgg ttg atg       1440
Glu Gly Phe Pro Gln Arg Pro Pro His Pro Ser Met Thr Trp Leu Met
465                 470                 475                 480 aaa cag ctc gat aag cat gat gtc ggt acc ggt gcg aca cga acg agc       1488
Lys Gln Leu Asp Lys His Asp Val Gly Thr Gly Ala Thr Arg Thr Ser
                485                 490                 495 acc tat gcc gag gtc aca gcc ggc aag tca gca ttg ctc aaa gaa acg       1536
Thr Tyr Ala Glu Val Thr Ala Gly Lys Ser Ala Leu Leu Lys Glu Thr
            500                 505                 510 cgt ggc aaa gtc act atg act gac gca ggg caa ctg aat tat ctg ctg       1584
Arg Gly Lys Val Thr Met Thr Asp Ala Gly Gln Leu Asn Tyr Leu Leu
```

```
Arg Gly Lys Val Thr Met Thr Asp Ala Gly Gln Leu Asn Tyr Leu Leu
        515                 520                 525 ctt cct ggc acc cac att ggc gac ctc aaa ctt acc gag cgc gtt tat      1632
Leu Pro Gly Thr His Ile Gly Asp Leu Lys Leu Thr Glu Arg Val Tyr
530                 535                 540 gcc gat atg gca gcg gtt gct gct ggt gaa aag act gca gag cag gca      1680
Ala Asp Met Ala Ala Val Ala Ala Gly Glu Lys Thr Ala Glu Gln Ala
545                 550                 555                 560 ctg gaa cca gtt aaa cag tgg gtc gaa gaa gat att gcg acc atg acc      1728
Leu Glu Pro Val Lys Gln Trp Val Glu Glu Asp Ile Ala Thr Met Thr
            565                 570                 575 cgt aac gca aaa aac atc ccc caa gaa cta gga aag aaa ctc atg act      1776
Arg Asn Ala Lys Asn Ile Pro Gln Glu Leu Gly Lys Lys Leu Met Thr
                580                 585                 590 act act ttt acc cct tct gtc aag cac tcc ggc acc tgg aac ggt gag      1824
Thr Thr Phe Thr Pro Ser Val Lys His Ser Gly Thr Trp Asn Gly Glu
            595                 600                 605 cag gtg agc ttt aag aag gtc tac tgc ggg cat gaa ttt agc gat gca      1872
Gln Val Ser Phe Lys Lys Val Tyr Cys Gly His Glu Phe Ser Asp Ala
610                 615                 620 gaa tgc gag gcg ttg ctg cgc ggt gag gag ctc acc att acc gat gcc      1920
Glu Cys Glu Ala Leu Leu Arg Gly Glu Glu Leu Thr Ile Thr Asp Ala
625                 630                 635                 640 atg att ggt gga cag atc acg aca gtc acc ggc aag ctg gcg cat caa      1968
Met Ile Gly Gly Gln Ile Thr Thr Val Thr Gly Lys Leu Ala His Gln
            645                 650                 655 agc ttt aac aaa gac ggc aag acc att aag ttc ttt ggg ttt aag ggg      2016
Ser Phe Asn Lys Asp Gly Lys Thr Ile Lys Phe Phe Gly Phe Lys Gly
            660                 665                 670 cag gtt gat cgc att gcc tct gca gac cca gct gtg tac gcg gtg ggt      2064
Gln Val Asp Arg Ile Ala Ser Ala Asp Pro Ala Val Tyr Ala Val Gly
        675                 680                 685 gtg tgg aag gtt gag ggt gaa aag att cgc ttc aag cgc gta tgg ggt      2112
Val Trp Lys Val Glu Gly Glu Lys Ile Arg Phe Lys Arg Val Trp Gly
690                 695                 700 ggt cac aag ttc acc gac aag gag atc gcc gat ctg ctt gag ggc cgc      2160
Gly His Lys Phe Thr Asp Lys Glu Ile Ala Asp Leu Leu Glu Gly Arg
705                 710                 715                 720 gag att gct ttt gat gcc atg tcg aag gcc aag aag ccg tac acc gct      2208
Glu Ile Ala Phe Asp Ala Met Ser Lys Ala Lys Lys Pro Tyr Thr Ala
                725                 730                 735 cgg gga tcg ctg cag cgc ggc gag tac aac ggt aat tcg ttc gtc ggc      2256
Arg Gly Ser Leu Gln Arg Gly Glu Tyr Asn Gly Asn Ser Phe Val Gly
            740                 745                 750 ttc cag ctc gca cca cgc gat taa                                      2280
Phe Gln Leu Ala Pro Arg Asp
        755

<210> SEQ ID NO 40
<211> LENGTH: 759
<212> TYPE: PRT
<213> ORGANISM: Corynebacterium glutamicum

<400> SEQUENCE: 40

Leu Thr Ile Gly Ile Leu Thr Glu Lys Ala Ser Ala Ala Lys Asn Phe
1               5                   10                  15

Ala Lys Ala Leu Gly Gly Pro Ser Gly Thr Tyr Asn Gly Glu Lys Tyr
            20                  25                  30

Val Ile Ala Ala Ala Ser Gly His Leu Tyr Glu Phe Val Glu Pro Glu
        35                  40                  45
```

```
Glu Met Val Pro Pro Ser Tyr Ala Asp Lys Ile Gly Gly Tyr Trp Asp
 50                  55                  60

Leu Ala Lys Leu Pro Trp Asp Glu Thr Gln Phe Leu Trp Ser Arg Glu
 65                  70                  75                  80

Gln Lys His Gly Ala Ala Asn Thr Ile Ala Arg Ile Lys Lys Thr Leu
                 85                  90                  95

Ser Ser Cys Thr Thr Ile Val Ile Gly Ser Asp Ile Asp Pro Thr Gly
            100                 105                 110

Glu Gly Asp Leu Leu Ala Trp Glu Ile Ile Ala Glu Leu Gly Leu Asp
            115                 120                 125

Thr Lys Lys Ile Gln Arg Met Glu Phe Val Asp Glu Ala Pro Ala Ser
    130                 135                 140

Ile Gln Gln Ala Phe Ile Asn Arg Arg Asp Val Thr Ser Met His Asp
145                 150                 155                 160

Glu Pro Asn Tyr Leu Lys Ala Glu Phe Arg Ser Arg Phe Asp Leu Leu
                165                 170                 175

Ser Met Gln Trp Thr Arg Gly Ala Thr Lys Val Leu Glu Thr Thr Gly
            180                 185                 190

Arg Arg Ala Val Leu Arg Asn Gly Arg Leu Lys Ser Ala Met Val Ala
        195                 200                 205

Ile Val Gly Gln Gly Leu Asp Ala Tyr Asn Asp Tyr Lys Lys Ile Pro
    210                 215                 220

Phe Tyr Gln Asn Arg Phe Ile Asp Asp His Gly Val Ser Tyr Val Asn
225                 230                 235                 240

Pro Glu Glu Pro Arg Tyr Lys Thr Cys Asp Glu Val Pro Gln Leu Tyr
                245                 250                 255

Lys Ala Ser Ala Val Glu Cys Tyr Glu Lys Ser Met Lys Lys Thr Ala
            260                 265                 270

Pro Pro Arg Leu Leu Asp Leu Ala Ser Leu Ser Ala Leu Leu Ser Lys
        275                 280                 285

Glu Gly Phe Ser Ala Lys Asn Val Leu Lys Thr Tyr Gln Gln Met Tyr
    290                 295                 300

Glu Ala Gln Val Val Ser Tyr Pro Arg Thr Glu Asp Lys Thr Ile Thr
305                 310                 315                 320

Pro Glu Gln Phe Lys Glu Leu Ala Pro Leu Val Asp Lys Ile Ala Gly
                325                 330                 335

Leu Val Gly Val Asn Pro Ala Asp Leu Thr His Arg Gln Pro Arg Ser
            340                 345                 350

Thr His Val Lys Pro Lys Gly Ala His Gly Ala Asn Arg Pro Gly Leu
        355                 360                 365

Asn Val Pro Thr Ser Ile Ala Ala Val Lys Thr Thr Tyr Gly Val Leu
    370                 375                 380

Gly Gln Arg Ile Tyr Glu Val Leu Ala Lys Ser Tyr Leu Thr Met Leu
385                 390                 395                 400

Ala Glu Asp Tyr Leu Tyr Glu His Gln Lys Gly Arg Val Val Asp Tyr
                405                 410                 415

Pro Ala Phe Leu Gly Thr Ala Asn Val Pro Lys Ser Leu Gly Trp Lys
            420                 425                 430

Gly Ile Phe Asp Val Asp Ala Glu Ala Asp Asp Ala Ala Gly Ser
        435                 440                 445

Asp Ala Ala Gln Gln Gly Ile Gly Thr Arg Ala Glu Pro Glu Val Phe
    450                 455                 460

Glu Gly Phe Pro Gln Arg Pro Pro His Pro Ser Met Thr Trp Leu Met
465                 470                 475                 480
```

-continued

Lys Gln Leu Asp Lys His Asp Val Gly Thr Ala Thr Arg Thr Ser
                485                 490                 495
Thr Tyr Ala Glu Val Thr Ala Gly Lys Ser Ala Leu Leu Lys Glu Thr
            500                 505                 510
Arg Gly Lys Val Thr Met Thr Asp Ala Gly Gln Leu Asn Tyr Leu Leu
            515                 520                 525
Leu Pro Gly Thr His Ile Gly Asp Leu Lys Leu Thr Glu Arg Val Tyr
        530                 535                 540
Ala Asp Met Ala Ala Val Ala Ala Gly Glu Lys Thr Ala Glu Gln Ala
545                 550                 555                 560
Leu Glu Pro Val Lys Gln Trp Val Glu Asp Ile Ala Thr Met Thr
                565                 570                 575
Arg Asn Ala Lys Asn Ile Pro Gln Glu Leu Gly Lys Lys Leu Met Thr
            580                 585                 590
Thr Thr Phe Thr Pro Ser Val Lys His Ser Gly Thr Trp Asn Gly Glu
        595                 600                 605
Gln Val Ser Phe Lys Lys Val Tyr Cys Gly His Glu Phe Ser Asp Ala
        610                 615                 620
Glu Cys Glu Ala Leu Leu Arg Gly Glu Leu Thr Ile Thr Asp Ala
625                 630                 635                 640
Met Ile Gly Gly Gln Ile Thr Thr Val Thr Gly Lys Leu Ala His Gln
                645                 650                 655
Ser Phe Asn Lys Asp Gly Lys Thr Ile Lys Phe Phe Gly Phe Lys Gly
                660                 665                 670
Gln Val Asp Arg Ile Ala Ser Ala Asp Pro Ala Val Tyr Ala Val Gly
        675                 680                 685
Val Trp Lys Val Glu Gly Glu Lys Ile Arg Phe Lys Arg Val Trp Gly
    690                 695                 700
Gly His Lys Phe Thr Asp Lys Glu Ile Ala Asp Leu Leu Gly Arg
705                 710                 715                 720
Glu Ile Ala Phe Asp Ala Met Ser Lys Ala Lys Lys Pro Tyr Thr Ala
                725                 730                 735
Arg Gly Ser Leu Gln Arg Gly Glu Tyr Asn Gly Asn Ser Phe Val Gly
            740                 745                 750
Phe Gln Leu Ala Pro Arg Asp
        755

<210> SEQ ID NO 41
<211> LENGTH: 29
<212> TYPE: DNA
<213> ORGANISM: Artificial Sequence
<220> FEATURE:
<223> OTHER INFORMATION: Synthetic DNA

<400> SEQUENCE: 41
tttggatccg gcactggcag aggtgctag                                29

<210> SEQ ID NO 42
<211> LENGTH: 29
<212> TYPE: DNA
<213> ORGANISM: Artificial Sequence
<220> FEATURE:
<223> OTHER INFORMATION: Synthetic DNA

<400> SEQUENCE: 42
tttggatcct taatcgcgtg gtgcgagct                                29

```
<210> SEQ ID NO 43
<211> LENGTH: 2628
<212> TYPE: DNA
<213> ORGANISM: Escherichia coli
<220> FEATURE:
<221> NAME/KEY: CDS
<222> LOCATION: (1)..(2628)

<400> SEQUENCE: 43 atg agc gac ctt gcg aga gaa att aca ccg gtc aac att gag gaa gag      48
Met Ser Asp Leu Ala Arg Glu Ile Thr Pro Val Asn Ile Glu Glu Glu
1               5                   10                  15 ctg aag agc tcc tat ctg gat tat gcg atg tcg gtc att gtt ggc cgt      96
Leu Lys Ser Ser Tyr Leu Asp Tyr Ala Met Ser Val Ile Val Gly Arg
            20                  25                  30 gcg ctg cca gat gtc cga gat ggc ctg aag ccg gta cac cgt cgc gta     144
Ala Leu Pro Asp Val Arg Asp Gly Leu Lys Pro Val His Arg Arg Val
        35                  40                  45 ctt tac gcc atg aac gta cta ggc aat gac tgg aac aaa gcc tat aaa     192
Leu Tyr Ala Met Asn Val Leu Gly Asn Asp Trp Asn Lys Ala Tyr Lys
    50                  55                  60 aaa tct gcc cgt gtc gtt ggt gac gta atc ggt aaa tac cat ccc cat     240
Lys Ser Ala Arg Val Val Gly Asp Val Ile Gly Lys Tyr His Pro His
65                  70                  75                  80 ggt gac tcg gcg gtc tat gac acg atc gtc cgc atg gcg cag cca ttc     288
Gly Asp Ser Ala Val Tyr Asp Thr Ile Val Arg Met Ala Gln Pro Phe
                85                  90                  95 tcg ctg cgt tat atg ctg gta gac ggt cag ggt aac ttc ggt tct atc     336
Ser Leu Arg Tyr Met Leu Val Asp Gly Gln Gly Asn Phe Gly Ser Ile
            100                 105                 110 gac ggc gac tct gcg gcg gca atg cgt tat acg gaa atc cgt ctg gcg     384
Asp Gly Asp Ser Ala Ala Ala Met Arg Tyr Thr Glu Ile Arg Leu Ala
        115                 120                 125 aaa att gcc cat gaa ctg atg gcc gat ctc gaa aaa gag acg gtc gat     432
Lys Ile Ala His Glu Leu Met Ala Asp Leu Glu Lys Glu Thr Val Asp
    130                 135                 140 ttc gtt gat aac tat gac ggc acg gaa aaa att ccg gac gtc atg cca     480
Phe Val Asp Asn Tyr Asp Gly Thr Glu Lys Ile Pro Asp Val Met Pro
145                 150                 155                 160 acc aaa att cct aac ctg ctg gtg aac ggt tct tcc ggt atc gcc gta     528
Thr Lys Ile Pro Asn Leu Leu Val Asn Gly Ser Ser Gly Ile Ala Val
                165                 170                 175 ggt atg gca acc aac atc ccg ccg cac aac ctg acg gaa gtc atc aac     576
Gly Met Ala Thr Asn Ile Pro Pro His Asn Leu Thr Glu Val Ile Asn
            180                 185                 190 ggt tgt ctg gcg tat att gat gat gaa gac atc agc att gaa ggg ctg     624
Gly Cys Leu Ala Tyr Ile Asp Asp Glu Asp Ile Ser Ile Glu Gly Leu
        195                 200                 205 atg gaa cac atc ccg ggg ccg gac ttc ccg acg gcg gca atc att aac     672
Met Glu His Ile Pro Gly Pro Asp Phe Pro Thr Ala Ala Ile Ile Asn
    210                 215                 220 ggt cgt cgc ggt att gaa gaa gct tac cgt acc ggt cgc ggc aag gtg     720
Gly Arg Arg Gly Ile Glu Glu Ala Tyr Arg Thr Gly Arg Gly Lys Val
225                 230                 235                 240 tat atc cgc gct cgc gca gaa gtg gaa gtt gac gcc aaa acc ggt cgt     768
Tyr Ile Arg Ala Arg Ala Glu Val Glu Val Asp Ala Lys Thr Gly Arg
                245                 250                 255 gaa acc att atc gtc cac gaa att ccg tat cag gta aac aaa gcg cgc     816
Glu Thr Ile Ile Val His Glu Ile Pro Tyr Gln Val Asn Lys Ala Arg
            260                 265                 270 ctg atc gag aag att gcg gaa ctg gta aaa gaa aaa cgc gtg gaa ggc     864
Leu Ile Glu Lys Ile Ala Glu Leu Val Lys Glu Lys Arg Val Glu Gly
```

```
                    275                 280                 285
atc agc gcg ctg cgt gac gag tct gac aaa gac ggt atg cgc atc gtg      912
Ile Ser Ala Leu Arg Asp Glu Ser Asp Lys Asp Gly Met Arg Ile Val
290                 295                 300 att gaa gtg aaa cgc gat gcg gtc ggt gaa gtt gtg ctc aac aac ctc      960
Ile Glu Val Lys Arg Asp Ala Val Gly Glu Val Val Leu Asn Asn Leu
305                 310                 315                 320 tac tcc cag acc cag ttg cag gtt tct ttc ggt atc aac atg gtg gca     1008
Tyr Ser Gln Thr Gln Leu Gln Val Ser Phe Gly Ile Asn Met Val Ala
                325                 330                 335 ttg cac cat ggt cag ccg aag atc atg aac ctg aaa gac atc atc gcg     1056
Leu His His Gly Gln Pro Lys Ile Met Asn Leu Lys Asp Ile Ile Ala
            340                 345                 350 gcg ttt gtt cgt cac cgc cgt gaa gtg gtg acc cgt cgt act att ttc     1104
Ala Phe Val Arg His Arg Arg Glu Val Val Thr Arg Arg Thr Ile Phe
        355                 360                 365 gaa ctg cgt aaa gct cgc gat cgt gct cat atc ctt gaa gca tta gcc     1152
Glu Leu Arg Lys Ala Arg Asp Arg Ala His Ile Leu Glu Ala Leu Ala
    370                 375                 380 gtg gcg ctg gcg aac atc gac ccg atc atc gaa ctg atc cgt cat gcg     1200
Val Ala Leu Ala Asn Ile Asp Pro Ile Ile Glu Leu Ile Arg His Ala
385                 390                 395                 400 ccg acg cct gca gaa gcg aaa act gcg ctg gtt gct aat ccg tgg cag     1248
Pro Thr Pro Ala Glu Ala Lys Thr Ala Leu Val Ala Asn Pro Trp Gln
                405                 410                 415 ctg ggc aac gtt gcc gcg atg ctc gaa cgt gct ggc gac gat gct gcg     1296
Leu Gly Asn Val Ala Ala Met Leu Glu Arg Ala Gly Asp Asp Ala Ala
            420                 425                 430 cgt ccg gaa tgg ctg gag cca gag ttc ggc gtg cgt gat ggt ctg tac     1344
Arg Pro Glu Trp Leu Glu Pro Glu Phe Gly Val Arg Asp Gly Leu Tyr
        435                 440                 445 tac ctg acc gaa cag caa gct cag gcg att ctg gat ctg cgt ttg cag     1392
Tyr Leu Thr Glu Gln Gln Ala Gln Ala Ile Leu Asp Leu Arg Leu Gln
    450                 455                 460 aaa ctg acc ggt ctt gag cac gaa aaa ctg ctc gac gaa tac aaa gag     1440
Lys Leu Thr Gly Leu Glu His Glu Lys Leu Leu Asp Glu Tyr Lys Glu
465                 470                 475                 480 ctg ctg gat cag atc gcg gaa ctg ttg cgt att ctt ggt agc gcc gat     1488
Leu Leu Asp Gln Ile Ala Glu Leu Leu Arg Ile Leu Gly Ser Ala Asp
                485                 490                 495 cgt ctg atg gaa gtg atc cgt gaa gag ctg gag ctg gtt cgt gaa cag     1536
Arg Leu Met Glu Val Ile Arg Glu Glu Leu Glu Leu Val Arg Glu Gln
            500                 505                 510 ttc ggt gac aaa cgt cgt act gaa atc acc gcc aac agc gca gac atc     1584
Phe Gly Asp Lys Arg Arg Thr Glu Ile Thr Ala Asn Ser Ala Asp Ile
        515                 520                 525 aac ctg gaa gat ctg atc acc cag gaa gat gtg gtc gtg acg ctc tct     1632
Asn Leu Glu Asp Leu Ile Thr Gln Glu Asp Val Val Val Thr Leu Ser
    530                 535                 540 cac cag ggc tac gtt aag tat cag ccg ctt tct gaa tac gaa gcg cag     1680
His Gln Gly Tyr Val Lys Tyr Gln Pro Leu Ser Glu Tyr Glu Ala Gln
545                 550                 555                 560 cgt cgt ggc ggg aaa ggt aaa tct gcc gca cgt att aaa gaa gaa gac     1728
Arg Arg Gly Gly Lys Gly Lys Ser Ala Ala Arg Ile Lys Glu Glu Asp
                565                 570                 575 ttt atc gac cga ctg ctg gtg gcg aac act cac gac cat att ctg tgc     1776
Phe Ile Asp Arg Leu Leu Val Ala Asn Thr His Asp His Ile Leu Cys
            580                 585                 590 ttc tcc agc cgt ggt cgc gtc tat tcg atg aaa gtt tat cag ttg ccg     1824
Phe Ser Ser Arg Gly Arg Val Tyr Ser Met Lys Val Tyr Gln Leu Pro
```

```
gaa gcc act cgt ggc gcg cgc ggt cgt ccg atc gtc aac ctg ctg ccg      1872
Glu Ala Thr Arg Gly Ala Arg Gly Arg Pro Ile Val Asn Leu Leu Pro
610                 615                 620 ctg gag cag gac gaa cgt atc act gcg atc ctg cca gtg acc gag ttt      1920
Leu Glu Gln Asp Glu Arg Ile Thr Ala Ile Leu Pro Val Thr Glu Phe
625                 630                 635                 640 gaa gaa ggc gtg aaa gtc ttc atg gcg acc gct aac ggt acc gtg aag      1968
Glu Glu Gly Val Lys Val Phe Met Ala Thr Ala Asn Gly Thr Val Lys
                645                 650                 655 aaa act gtc ctc acc gag ttc aac cgt ctg cgt acc gcc ggt aaa gtg      2016
Lys Thr Val Leu Thr Glu Phe Asn Arg Leu Arg Thr Ala Gly Lys Val
            660                 665                 670 gcg atc aaa ctg gtt gac ggc gat gag ctg atc ggc gtt gac ctg acc      2064
Ala Ile Lys Leu Val Asp Gly Asp Glu Leu Ile Gly Val Asp Leu Thr
        675                 680                 685 agc ggc gaa gac gaa gta atg ctg ttc tcc gct gaa ggt aaa gtg gtg      2112
Ser Gly Glu Asp Glu Val Met Leu Phe Ser Ala Glu Gly Lys Val Val
    690                 695                 700 cgc ttt aaa gag tct tct gtc cgt gcg atg ggc tgc aac acc acc ggt      2160
Arg Phe Lys Glu Ser Ser Val Arg Ala Met Gly Cys Asn Thr Thr Gly
705                 710                 715                 720 gtt cgc ggt att cgc tta ggt gaa ggc gat aaa gtc gtc tct ctg atc      2208
Val Arg Gly Ile Arg Leu Gly Glu Gly Asp Lys Val Val Ser Leu Ile
                725                 730                 735 gtg cct cgt ggc gat ggc gca atc ctc acc gca acg caa aac ggt tac      2256
Val Pro Arg Gly Asp Gly Ala Ile Leu Thr Ala Thr Gln Asn Gly Tyr
            740                 745                 750 ggt aaa cgt acc gca gtg gcg gaa tac cca acc aag tcg cgt gcg acg      2304
Gly Lys Arg Thr Ala Val Ala Glu Tyr Pro Thr Lys Ser Arg Ala Thr
        755                 760                 765 aaa ggg gtt atc tcc atc aag gtt acc gaa cgt aac ggt tta gtt gtt      2352
Lys Gly Val Ile Ser Ile Lys Val Thr Glu Arg Asn Gly Leu Val Val
    770                 775                 780 ggc gcg gta cag gta gat gac tgc gac cag atc atg atg atc acc gat      2400
Gly Ala Val Gln Val Asp Asp Cys Asp Gln Ile Met Met Ile Thr Asp
785                 790                 795                 800 gcc ggt acg ctg gta cgt act cgc gtt tcg gaa atc agc atc gtg ggc      2448
Ala Gly Thr Leu Val Arg Thr Arg Val Ser Glu Ile Ser Ile Val Gly
                805                 810                 815 cgt aac acc cag ggc gtg atc ctc atc cgt act gcg gaa gat gaa aac      2496
Arg Asn Thr Gln Gly Val Ile Leu Ile Arg Thr Ala Glu Asp Glu Asn
            820                 825                 830 gta gtg ggt ctg caa cgt gtt gct gaa ccg gtt gac gag gaa gat ctg      2544
Val Val Gly Leu Gln Arg Val Ala Glu Pro Val Asp Glu Glu Asp Leu
        835                 840                 845 gat acc atc gac ggc agt gcc gcg gaa ggg gac gat gaa atc gct ccg      2592
Asp Thr Ile Asp Gly Ser Ala Ala Glu Gly Asp Asp Glu Ile Ala Pro
    850                 855                 860 gaa gtg gac gtt gac gac gag cca gaa gaa gaa taa                      2628
Glu Val Asp Val Asp Asp Glu Pro Glu Glu Glu
865                 870                 875

<210> SEQ ID NO 44
<211> LENGTH: 875
<212> TYPE: PRT
<213> ORGANISM: Escherichia coli

<400> SEQUENCE: 44

Met Ser Asp Leu Ala Arg Glu Ile Thr Pro Val Asn Ile Glu Glu Glu
1               5                   10                  15
```

```
Leu Lys Ser Ser Tyr Leu Asp Tyr Ala Met Ser Val Ile Val Gly Arg
            20                  25                  30

Ala Leu Pro Asp Val Arg Asp Gly Leu Lys Pro Val His Arg Arg Val
            35                  40                  45

Leu Tyr Ala Met Asn Val Leu Gly Asn Asp Trp Asn Lys Ala Tyr Lys
 50                  55                  60

Lys Ser Ala Arg Val Val Gly Asp Val Ile Gly Lys Tyr His Pro His
 65                  70                  75                  80

Gly Asp Ser Ala Val Tyr Asp Thr Ile Val Arg Met Ala Gln Pro Phe
                 85                  90                  95

Ser Leu Arg Tyr Met Leu Val Asp Gly Gln Gly Asn Phe Gly Ser Ile
            100                 105                 110

Asp Gly Asp Ser Ala Ala Ala Met Arg Tyr Thr Glu Ile Arg Leu Ala
            115                 120                 125

Lys Ile Ala His Glu Leu Met Ala Asp Leu Glu Lys Glu Thr Val Asp
130                 135                 140

Phe Val Asp Asn Tyr Asp Gly Thr Glu Lys Ile Pro Asp Val Met Pro
145                 150                 155                 160

Thr Lys Ile Pro Asn Leu Leu Val Asn Gly Ser Ser Gly Ile Ala Val
            165                 170                 175

Gly Met Ala Thr Asn Ile Pro Pro His Asn Leu Thr Glu Val Ile Asn
            180                 185                 190

Gly Cys Leu Ala Tyr Ile Asp Asp Glu Asp Ile Ser Ile Glu Gly Leu
            195                 200                 205

Met Glu His Ile Pro Gly Pro Asp Phe Pro Thr Ala Ala Ile Ile Asn
210                 215                 220

Gly Arg Arg Gly Ile Glu Glu Ala Tyr Arg Thr Gly Arg Gly Lys Val
225                 230                 235                 240

Tyr Ile Arg Ala Arg Ala Glu Val Glu Val Asp Ala Lys Thr Gly Arg
            245                 250                 255

Glu Thr Ile Ile Val His Glu Ile Pro Tyr Gln Val Asn Lys Ala Arg
            260                 265                 270

Leu Ile Glu Lys Ile Ala Glu Leu Val Lys Glu Lys Arg Val Glu Gly
            275                 280                 285

Ile Ser Ala Leu Arg Asp Glu Ser Asp Lys Asp Gly Met Arg Ile Val
            290                 295                 300

Ile Glu Val Lys Arg Asp Ala Val Gly Glu Val Val Leu Asn Asn Leu
305                 310                 315                 320

Tyr Ser Gln Thr Gln Leu Gln Val Ser Phe Gly Ile Asn Met Val Ala
            325                 330                 335

Leu His His Gly Gln Pro Lys Ile Met Asn Leu Lys Asp Ile Ile Ala
            340                 345                 350

Ala Phe Val Arg His Arg Arg Glu Val Val Thr Arg Arg Thr Ile Phe
            355                 360                 365

Glu Leu Arg Lys Ala Arg Asp Arg Ala His Ile Leu Glu Ala Leu Ala
            370                 375                 380

Val Ala Leu Ala Asn Ile Asp Pro Ile Ile Glu Leu Ile Arg His Ala
385                 390                 395                 400

Pro Thr Pro Ala Glu Ala Lys Thr Ala Leu Val Ala Asn Pro Trp Gln
            405                 410                 415

Leu Gly Asn Val Ala Ala Met Leu Glu Arg Ala Gly Asp Asp Ala Ala
            420                 425                 430

Arg Pro Glu Trp Leu Glu Pro Glu Phe Gly Val Arg Asp Gly Leu Tyr
```

```
                435                 440                 445
Tyr Leu Thr Glu Gln Gln Ala Gln Ala Ile Leu Asp Leu Arg Leu Gln
450                 455                 460
Lys Leu Thr Gly Leu Glu His Glu Lys Leu Leu Asp Glu Tyr Lys Glu
465                 470                 475                 480
Leu Leu Asp Gln Ile Ala Glu Leu Leu Arg Ile Leu Gly Ser Ala Asp
                485                 490                 495
Arg Leu Met Glu Val Ile Arg Glu Leu Glu Leu Val Arg Glu Gln
                500                 505                 510
Phe Gly Asp Lys Arg Arg Thr Glu Ile Thr Ala Asn Ser Ala Asp Ile
                515                 520                 525
Asn Leu Glu Asp Leu Ile Thr Gln Asp Val Val Thr Leu Ser
530                 535                 540
His Gln Gly Tyr Val Lys Tyr Gln Pro Leu Ser Glu Tyr Glu Ala Gln
545                 550                 555                 560
Arg Arg Gly Gly Lys Gly Lys Ser Ala Ala Arg Ile Lys Glu Glu Asp
                565                 570                 575
Phe Ile Asp Arg Leu Leu Val Ala Asn Thr His Asp His Ile Leu Cys
                580                 585                 590
Phe Ser Ser Arg Gly Arg Val Tyr Ser Met Lys Val Tyr Gln Leu Pro
                595                 600                 605
Glu Ala Thr Arg Gly Ala Arg Gly Arg Pro Ile Val Asn Leu Leu Pro
610                 615                 620
Leu Glu Gln Asp Glu Arg Ile Thr Ala Ile Leu Pro Val Thr Glu Phe
625                 630                 635                 640
Glu Glu Gly Val Lys Val Phe Met Ala Thr Ala Asn Gly Thr Val Lys
                645                 650                 655
Lys Thr Val Leu Thr Glu Phe Asn Arg Leu Arg Thr Ala Gly Lys Val
                660                 665                 670
Ala Ile Lys Leu Val Asp Gly Asp Glu Leu Ile Gly Val Asp Leu Thr
                675                 680                 685
Ser Gly Glu Asp Glu Val Met Leu Phe Ser Ala Glu Gly Lys Val Val
690                 695                 700
Arg Phe Lys Glu Ser Ser Val Arg Ala Met Gly Cys Asn Thr Thr Gly
705                 710                 715                 720
Val Arg Gly Ile Arg Leu Gly Glu Gly Asp Lys Val Val Ser Leu Ile
                725                 730                 735
Val Pro Arg Gly Asp Gly Ala Ile Leu Thr Ala Thr Gln Asn Gly Tyr
                740                 745                 750
Gly Lys Arg Thr Ala Val Ala Glu Tyr Pro Thr Lys Ser Arg Ala Thr
                755                 760                 765
Lys Gly Val Ile Ser Ile Lys Val Thr Glu Arg Asn Gly Leu Val Val
770                 775                 780
Gly Ala Val Gln Val Asp Asp Cys Asp Gln Ile Met Met Ile Thr Asp
785                 790                 795                 800
Ala Gly Thr Leu Val Arg Thr Arg Val Ser Glu Ile Ser Ile Val Gly
                805                 810                 815
Arg Asn Thr Gln Gly Val Ile Leu Ile Arg Thr Ala Glu Asp Glu Asn
                820                 825                 830
Val Val Gly Leu Gln Arg Val Ala Glu Pro Val Asp Glu Glu Asp Leu
                835                 840                 845
Asp Thr Ile Asp Gly Ser Ala Glu Gly Asp Asp Glu Ile Ala Pro
850                 855                 860
```

```
Glu Val Asp Val Asp Asp Glu Pro Glu Glu Glu
865                 870                 875

<210> SEQ ID NO 45
<211> LENGTH: 2415
<212> TYPE: DNA
<213> ORGANISM: Escherichia coli
<220> FEATURE:
<221> NAME/KEY: CDS
<222> LOCATION: (1)..(2415)

<400> SEQUENCE: 45 atg tcg aat tct tat gac tcc tcc agt atc aaa gtc ctg aaa ggg ctg     48
Met Ser Asn Ser Tyr Asp Ser Ser Ser Ile Lys Val Leu Lys Gly Leu
1               5                   10                  15 gat gcg gtg cgt aag cgc ccg ggt atg tat atc ggc gac acg gat gac     96
Asp Ala Val Arg Lys Arg Pro Gly Met Tyr Ile Gly Asp Thr Asp Asp
            20                  25                  30 ggc acc ggt ctg cac cac atg gta ttc gag gtg gta gat aac gct atc    144
Gly Thr Gly Leu His His Met Val Phe Glu Val Val Asp Asn Ala Ile
        35                  40                  45 gac gaa gcg ctc gcg ggt cac tgt aaa gaa att atc gtc acc att cac    192
Asp Glu Ala Leu Ala Gly His Cys Lys Glu Ile Ile Val Thr Ile His
50                  55                  60 gcc gat aac tct gtc tct gta cag gat gac ggg cgg ggc att ccg acc    240
Ala Asp Asn Ser Val Ser Val Gln Asp Asp Gly Arg Gly Ile Pro Thr
65                  70                  75                  80 ggt att cac ccg gaa gag ggc gta tcg gcg gcg gaa gtg atc atg acc    288
Gly Ile His Pro Glu Glu Gly Val Ser Ala Ala Glu Val Ile Met Thr
                85                  90                  95 gtt ctg cac gca ggc ggt aaa ttt gac gat aac tcc tat aaa gtg tcc    336
Val Leu His Ala Gly Gly Lys Phe Asp Asp Asn Ser Tyr Lys Val Ser
            100                 105                 110 ggc ggt ctg cac ggc gtt ggt gtt tcg gta gta aac gcc ctg tcg caa    384
Gly Gly Leu His Gly Val Gly Val Ser Val Val Asn Ala Leu Ser Gln
        115                 120                 125 aaa ctg gag ctg gtt atc cag cgc gag ggt aaa att cac cgt cag atc    432
Lys Leu Glu Leu Val Ile Gln Arg Glu Gly Lys Ile His Arg Gln Ile
130                 135                 140 tac gaa cac ggt gta ccg cag gcc ccg ctg gcg gtt acc ggc gag act    480
Tyr Glu His Gly Val Pro Gln Ala Pro Leu Ala Val Thr Gly Glu Thr
145                 150                 155                 160 gaa aaa acc ggc acc atg gtg cgt ttc tgg ccc agc ctc gaa acc ttc    528
Glu Lys Thr Gly Thr Met Val Arg Phe Trp Pro Ser Leu Glu Thr Phe
                165                 170                 175 acc aat gtg acc gag ttc gaa tat gaa att ctg gcg aaa cgt ctg cgt    576
Thr Asn Val Thr Glu Phe Glu Tyr Glu Ile Leu Ala Lys Arg Leu Arg
            180                 185                 190 gag ttg tcg ttc ctc aac tcc ggc gtt tcc att cgt ctg cgc gac aag    624
Glu Leu Ser Phe Leu Asn Ser Gly Val Ser Ile Arg Leu Arg Asp Lys
        195                 200                 205 cgc gac ggc aaa gaa gac cac ttc cac tat gaa ggc ggc atc aag gcg    672
Arg Asp Gly Lys Glu Asp His Phe His Tyr Glu Gly Gly Ile Lys Ala
210                 215                 220 ttc gtt gaa tat ctg aac aag aac aaa acg ccg atc cac ccg aat atc    720
Phe Val Glu Tyr Leu Asn Lys Asn Lys Thr Pro Ile His Pro Asn Ile
225                 230                 235                 240 ttc tac ttc tcc act gaa aaa gac ggt att ggc gtc gaa gtg gcg ttg    768
Phe Tyr Phe Ser Thr Glu Lys Asp Gly Ile Gly Val Glu Val Ala Leu
                245                 250                 255 cag tgg aac gat ggc ttc cag gaa aac atc tac tgc ttt acc aac aac    816
Gln Trp Asn Asp Gly Phe Gln Glu Asn Ile Tyr Cys Phe Thr Asn Asn
```

-continued

```
                    260                 265                 270
att ccg cag cgt gac ggc ggt act cac ctg gca ggc ttc cgt gcg gcg      864
Ile Pro Gln Arg Asp Gly Gly Thr His Leu Ala Gly Phe Arg Ala Ala
        275                 280                 285 atg acc cgt acc ctg aac gcc tac atg gac aaa gaa ggc tac agc aaa      912
Met Thr Arg Thr Leu Asn Ala Tyr Met Asp Lys Glu Gly Tyr Ser Lys
290                 295                 300 aaa gcc aaa gtc agc gcc acc ggt gac gat gcg cgt gaa ggc ctg att      960
Lys Ala Lys Val Ser Ala Thr Gly Asp Asp Ala Arg Glu Gly Leu Ile
305                 310                 315                 320 gcg gtc gtt tcc gtg aaa gtg ccg gac ccg aaa ttc tcc tcc cag acc     1008
Ala Val Val Ser Val Lys Val Pro Asp Pro Lys Phe Ser Ser Gln Thr
                325                 330                 335 aaa gac aaa ctg gtt tct tct gag gtg aaa tcg gcg gtt gaa cag cag     1056
Lys Asp Lys Leu Val Ser Ser Glu Val Lys Ser Ala Val Glu Gln Gln
        340                 345                 350 atg aac gaa ctg ctg gca gaa tac ctg ctg gaa aac cca acc gac gcg     1104
Met Asn Glu Leu Leu Ala Glu Tyr Leu Leu Glu Asn Pro Thr Asp Ala
                355                 360                 365 aaa atc gtg gtt ggc aaa att atc gat gct gcc cgt gcc cgt gaa gcg     1152
Lys Ile Val Val Gly Lys Ile Ile Asp Ala Ala Arg Ala Arg Glu Ala
370                 375                 380 gcg cgt cgc gcg cgt gaa atg acc cgc cgt aaa ggt gcg ctc gac tta     1200
Ala Arg Arg Ala Arg Glu Met Thr Arg Arg Lys Gly Ala Leu Asp Leu
385                 390                 395                 400 gcg ggc ctg ccg ggc aaa ctg gca gac tgc cag gaa cgc gat ccg gcg     1248
Ala Gly Leu Pro Gly Lys Leu Ala Asp Cys Gln Glu Arg Asp Pro Ala
                405                 410                 415 ctt tcc gaa ctg tac ctg gtg gaa ggg gac tcc gcg ggc ggc tct gcg     1296
Leu Ser Glu Leu Tyr Leu Val Glu Gly Asp Ser Ala Gly Gly Ser Ala
                420                 425                 430 aag cag ggg cgt aac cgc aag aac cag gcg att ctg ccg ctg aag ggt     1344
Lys Gln Gly Arg Asn Arg Lys Asn Gln Ala Ile Leu Pro Leu Lys Gly
        435                 440                 445 aaa atc ctc aac gtc gag aaa gcg cgc ttc gat aag atg ctc tct tct     1392
Lys Ile Leu Asn Val Glu Lys Ala Arg Phe Asp Lys Met Leu Ser Ser
450                 455                 460 cag gaa gtg gcg acg ctt atc acc gcg ctt ggc tgt ggt atc ggt cgt     1440
Gln Glu Val Ala Thr Leu Ile Thr Ala Leu Gly Cys Gly Ile Gly Arg
465                 470                 475                 480 gac gag tac aac ccg gac aaa ctg cgt tat cac agc atc atc atc atg     1488
Asp Glu Tyr Asn Pro Asp Lys Leu Arg Tyr His Ser Ile Ile Ile Met
                485                 490                 495 acc gat gcg gac gtc gac ggc tcg cac att cgt acg ctg ctg ttg acc     1536
Thr Asp Ala Asp Val Asp Gly Ser His Ile Arg Thr Leu Leu Leu Thr
                500                 505                 510 ttc ttc tat cgt cag atg ccg gaa atc gtt gaa cgc ggt cac gtc tac     1584
Phe Phe Tyr Arg Gln Met Pro Glu Ile Val Glu Arg Gly His Val Tyr
        515                 520                 525 atc gct cag ccg ccg ctg tac aaa gtg aag aaa ggc aag cag gaa cag     1632
Ile Ala Gln Pro Pro Leu Tyr Lys Val Lys Lys Gly Lys Gln Glu Gln
530                 535                 540 tac att aaa gac gac gaa gcg atg gat cag tac cag atc tct atc gcg     1680
Tyr Ile Lys Asp Asp Glu Ala Met Asp Gln Tyr Gln Ile Ser Ile Ala
545                 550                 555                 560 ctg gac ggc gca acg ctg cac acc aac gcc agt gca ccg gca ttg gct     1728
Leu Asp Gly Ala Thr Leu His Thr Asn Ala Ser Ala Pro Ala Leu Ala
                565                 570                 575 ggc gaa gcg tta gag aaa ctg gta tct gag tac aac gcg acg cag aaa     1776
Gly Glu Ala Leu Glu Lys Leu Val Ser Glu Tyr Asn Ala Thr Gln Lys
```

-continued

```
                          580                 585                 590
atg atc aat cgt atg gag cgt cgt tat ccg aaa gca atg ctg aaa gag      1824
Met Ile Asn Arg Met Glu Arg Arg Tyr Pro Lys Ala Met Leu Lys Glu
        595                 600                 605 ctt atc tat cag ccg acg ttg acg gaa gct gac ctt tct gat gag cag      1872
Leu Ile Tyr Gln Pro Thr Leu Thr Glu Ala Asp Leu Ser Asp Glu Gln
610                 615                 620 acc gtt acc cgc tgg gtg aac gcg ctg gtc agc gaa ctg aac gac aaa      1920
Thr Val Thr Arg Trp Val Asn Ala Leu Val Ser Glu Leu Asn Asp Lys
625                 630                 635                 640 gaa cag cac ggc agc cag tgg aag ttt gat gtt cac acc aat gct gag      1968
Glu Gln His Gly Ser Gln Trp Lys Phe Asp Val His Thr Asn Ala Glu
                645                 650                 655 caa aac ctg ttc gag ccg att gtt cgc gtg cgt acc cac ggt gtg gat      2016
Gln Asn Leu Phe Glu Pro Ile Val Arg Val Arg Thr His Gly Val Asp
            660                 665                 670 act gac tat ccg ctg gat cac gag ttt atc acc ggt ggc gaa tat cgt      2064
Thr Asp Tyr Pro Leu Asp His Glu Phe Ile Thr Gly Gly Glu Tyr Arg
        675                 680                 685 cgt atc tgc acg ctg ggt gag aaa ctg cgt ggc ttg ctg gaa gaa gat      2112
Arg Ile Cys Thr Leu Gly Glu Lys Leu Arg Gly Leu Leu Glu Glu Asp
690                 695                 700 gcg ttt atc gaa cgt ggc gag cgt cgt cag ccg gta gcc agc ttc gag      2160
Ala Phe Ile Glu Arg Gly Glu Arg Arg Gln Pro Val Ala Ser Phe Glu
705                 710                 715                 720 cag gcg ctg gac tgg ctg gtg aaa gag tcc cgt cgc ggc ctc tcc atc      2208
Gln Ala Leu Asp Trp Leu Val Lys Glu Ser Arg Arg Gly Leu Ser Ile
                725                 730                 735 cag cgt tat aaa ggt ctg ggc gag atg aac ccg gaa cag ctg tgg gaa      2256
Gln Arg Tyr Lys Gly Leu Gly Glu Met Asn Pro Glu Gln Leu Trp Glu
            740                 745                 750 acc act atg gac ccg gaa agt cgt cgt atg ctg cgc gtt acc gtt aaa      2304
Thr Thr Met Asp Pro Glu Ser Arg Arg Met Leu Arg Val Thr Val Lys
        755                 760                 765 gat gcg att gct gcc gac cag ttg ttc acc acg ctg atg ggc gac gcc      2352
Asp Ala Ile Ala Ala Asp Gln Leu Phe Thr Thr Leu Met Gly Asp Ala
770                 775                 780 gtt gaa ccg cgc cgt gcg ttt att gaa gag aac gcc ctg aaa gcg gcg      2400
Val Glu Pro Arg Arg Ala Phe Ile Glu Glu Asn Ala Leu Lys Ala Ala
785                 790                 795                 800 aat atc gat att taa                                                  2415
Asn Ile Asp Ile
```

<210> SEQ ID NO 46
<211> LENGTH: 804
<212> TYPE: PRT
<213> ORGANISM: Escherichia coli

<400> SEQUENCE: 46

```
Met Ser Asn Ser Tyr Asp Ser Ser Ile Lys Val Leu Lys Gly Leu
1               5                   10                  15

Asp Ala Val Arg Lys Arg Pro Gly Met Tyr Ile Gly Asp Thr Asp Asp
                20                  25                  30

Gly Thr Gly Leu His His Met Val Phe Glu Val Val Asp Asn Ala Ile
            35                  40                  45

Asp Glu Ala Leu Ala Gly His Cys Lys Glu Ile Ile Val Thr Ile His
        50                  55                  60

Ala Asp Asn Ser Val Ser Val Gln Asp Asp Gly Arg Gly Ile Pro Thr
65                  70                  75                  80
```

```
Gly Ile His Pro Glu Glu Gly Val Ser Ala Ala Glu Val Ile Met Thr
                85                  90                  95

Val Leu His Ala Gly Gly Lys Phe Asp Asp Asn Ser Tyr Lys Val Ser
            100                 105                 110

Gly Gly Leu His Gly Val Gly Val Ser Val Val Asn Ala Leu Ser Gln
            115                 120                 125

Lys Leu Glu Leu Val Ile Gln Arg Glu Gly Lys Ile His Arg Gln Ile
        130                 135                 140

Tyr Glu His Gly Val Pro Gln Ala Pro Leu Ala Val Thr Gly Glu Thr
145                 150                 155                 160

Glu Lys Thr Gly Thr Met Val Arg Phe Trp Pro Ser Leu Glu Thr Phe
                165                 170                 175

Thr Asn Val Thr Glu Phe Glu Tyr Glu Ile Leu Ala Lys Arg Leu Arg
            180                 185                 190

Glu Leu Ser Phe Leu Asn Ser Gly Val Ser Ile Arg Leu Arg Asp Lys
            195                 200                 205

Arg Asp Gly Lys Glu Asp His Phe His Tyr Glu Gly Gly Ile Lys Ala
        210                 215                 220

Phe Val Glu Tyr Leu Asn Lys Asn Lys Thr Pro Ile His Pro Asn Ile
225                 230                 235                 240

Phe Tyr Phe Ser Thr Glu Lys Asp Gly Ile Gly Val Glu Val Ala Leu
                245                 250                 255

Gln Trp Asn Asp Gly Phe Gln Glu Asn Ile Tyr Cys Phe Thr Asn Asn
            260                 265                 270

Ile Pro Gln Arg Asp Gly Thr His Leu Ala Gly Phe Arg Ala Ala
        275                 280                 285

Met Thr Arg Thr Leu Asn Ala Tyr Met Asp Lys Glu Gly Tyr Ser Lys
        290                 295                 300

Lys Ala Lys Val Ser Ala Thr Gly Asp Asp Ala Arg Glu Gly Leu Ile
305                 310                 315                 320

Ala Val Val Ser Val Lys Val Pro Asp Pro Lys Phe Ser Ser Gln Thr
                325                 330                 335

Lys Asp Lys Leu Val Ser Ser Glu Val Lys Ser Ala Val Glu Gln Gln
            340                 345                 350

Met Asn Glu Leu Leu Ala Glu Tyr Leu Leu Glu Asn Pro Thr Asp Ala
        355                 360                 365

Lys Ile Val Val Gly Lys Ile Ile Asp Ala Ala Arg Ala Arg Glu Ala
        370                 375                 380

Ala Arg Arg Ala Arg Glu Met Thr Arg Arg Lys Gly Ala Leu Asp Leu
385                 390                 395                 400

Ala Gly Leu Pro Gly Lys Leu Ala Asp Cys Gln Glu Arg Asp Pro Ala
                405                 410                 415

Leu Ser Glu Leu Tyr Leu Val Glu Gly Asp Ser Ala Gly Gly Ser Ala
            420                 425                 430

Lys Gln Gly Arg Asn Arg Lys Asn Gln Ala Ile Leu Pro Leu Lys Gly
        435                 440                 445

Lys Ile Leu Asn Val Glu Lys Ala Arg Phe Asp Lys Met Leu Ser Ser
450                 455                 460

Gln Glu Val Ala Thr Leu Ile Thr Ala Leu Gly Cys Gly Ile Gly Arg
465                 470                 475                 480

Asp Glu Tyr Asn Pro Asp Lys Leu Arg Tyr His Ser Ile Ile Met Thr
                485                 490                 495

Thr Asp Ala Asp Val Asp Gly Ser His Ile Arg Thr Leu Leu Leu Thr
            500                 505                 510
```

```
Phe Phe Tyr Arg Gln Met Pro Glu Ile Val Glu Arg Gly His Val Tyr
            515                 520                 525

Ile Ala Gln Pro Pro Leu Tyr Lys Val Lys Gly Lys Gln Glu Gln
        530                 535                 540

Tyr Ile Lys Asp Asp Glu Ala Met Asp Gln Tyr Gln Ile Ser Ile Ala
545                 550                 555                 560

Leu Asp Gly Ala Thr Leu His Thr Asn Ala Ser Ala Pro Ala Leu Ala
                565                 570                 575

Gly Glu Ala Leu Glu Lys Leu Val Ser Glu Tyr Asn Ala Thr Gln Lys
            580                 585                 590

Met Ile Asn Arg Met Glu Arg Arg Tyr Pro Lys Ala Met Leu Lys Glu
        595                 600                 605

Leu Ile Tyr Gln Pro Thr Leu Thr Glu Ala Asp Leu Ser Asp Glu Gln
    610                 615                 620

Thr Val Thr Arg Trp Val Asn Ala Leu Val Ser Glu Leu Asn Asp Lys
625                 630                 635                 640

Glu Gln His Gly Ser Gln Trp Lys Phe Asp Val His Thr Asn Ala Glu
                645                 650                 655

Gln Asn Leu Phe Glu Pro Ile Val Arg Val Arg Thr His Gly Val Asp
            660                 665                 670

Thr Asp Tyr Pro Leu Asp His Glu Phe Ile Thr Gly Gly Glu Tyr Arg
        675                 680                 685

Arg Ile Cys Thr Leu Gly Glu Lys Leu Arg Gly Leu Leu Glu Asp
    690                 695                 700

Ala Phe Ile Glu Arg Gly Glu Arg Arg Gln Pro Val Ala Ser Phe Glu
705                 710                 715                 720

Gln Ala Leu Asp Trp Leu Val Lys Glu Ser Arg Gly Leu Ser Ile
                725                 730                 735

Gln Arg Tyr Lys Gly Leu Gly Glu Met Asn Pro Glu Gln Leu Trp Glu
            740                 745                 750

Thr Thr Met Asp Pro Glu Ser Arg Arg Met Leu Arg Val Thr Val Lys
        755                 760                 765

Asp Ala Ile Ala Ala Asp Gln Leu Phe Thr Thr Leu Met Gly Asp Ala
770                 775                 780

Val Glu Pro Arg Arg Ala Phe Ile Glu Glu Asn Ala Leu Lys Ala Ala
785                 790                 795                 800

Asn Ile Asp Ile

<210> SEQ ID NO 47
<211> LENGTH: 2571
<212> TYPE: DNA
<213> ORGANISM: Corynebacterium glutamicum
<220> FEATURE:
<221> NAME/KEY: CDS
<222> LOCATION: (1)..(2571)

<400> SEQUENCE: 47 gtg agc gac gac aat acc gga caa ttt gac cgc gtt aat ccc att gat      48
Val Ser Asp Asp Asn Thr Gly Gln Phe Asp Arg Val Asn Pro Ile Asp
1               5                   10                  15 atc aat gag gaa atg cag tcg agc tac atc gac tac gcg atg tca gtc      96
Ile Asn Glu Glu Met Gln Ser Ser Tyr Ile Asp Tyr Ala Met Ser Val
                20                  25                  30 atc gtc gga cgt gcc ctc cca gag gtg cgc gac ggc ctg aag cca gtc     144
Ile Val Gly Arg Ala Leu Pro Glu Val Arg Asp Gly Leu Lys Pro Val
            35                  40                  45
```

-continued

| | | |
|---|---|---|
| cac cgc cgc gtc ttg tac gcg atg ttc gac aac ggc tac cgc ccc gac<br>His Arg Arg Val Leu Tyr Ala Met Phe Asp Asn Gly Tyr Arg Pro Asp<br>50                         55                        60 | 192 |
| cgc agc tac gtg aag tct gca aaa cca gtg gca gac acc atg ggt aac<br>Arg Ser Tyr Val Lys Ser Ala Lys Pro Val Ala Asp Thr Met Gly Asn<br>65                     70                    75                        80 | 240 |
| ttc cac cca cac ggc gac acc gca att tat gac acg ttg gtg cgc atg<br>Phe His Pro His Gly Asp Thr Ala Ile Tyr Asp Thr Leu Val Arg Met<br>                 85                    90                       95 | 288 |
| gct cag cca tgg tcc atg cga tac ccg ctg gta gac ggc cag ggt aac<br>Ala Gln Pro Trp Ser Met Arg Tyr Pro Leu Val Asp Gly Gln Gly Asn<br>                100                   105                      110 | 336 |
| ttc ggt tcc cgc ggc aac gac ggc cct gca gca atg cgt tac acc gag<br>Phe Gly Ser Arg Gly Asn Asp Gly Pro Ala Ala Met Arg Tyr Thr Glu<br>                115                   120                      125 | 384 |
| tgc cgc atg acc cca ctg gcc atg gag atg gtg cgc gac atc cgc gaa<br>Cys Arg Met Thr Pro Leu Ala Met Glu Met Val Arg Asp Ile Arg Glu<br>130                       135                      140 | 432 |
| aac acc gtc aac ttc tca cca aac tac gac ggt aaa acc ctc gaa cca<br>Asn Thr Val Asn Phe Ser Pro Asn Tyr Asp Gly Lys Thr Leu Glu Pro<br>145                       150                    155                    160 | 480 |
| gac gtt ttg cca tcg cgc gtt cca aac ttg ttg atg aac ggt tcg ggc<br>Asp Val Leu Pro Ser Arg Val Pro Asn Leu Leu Met Asn Gly Ser Gly<br>                165                   170                      175 | 528 |
| ggc att gcg gtc ggc atg gcc acc aac atc cca ccg cac aac ctc aac<br>Gly Ile Ala Val Gly Met Ala Thr Asn Ile Pro Pro His Asn Leu Asn<br>                    180                   185 | 576 |
| gag ctt gcc gac gcc atc ttc tgg ctc ctg gaa aac cca gac gcc gaa<br>Glu Leu Ala Asp Ala Ile Phe Trp Leu Leu Glu Asn Pro Asp Ala Glu<br>                195                   200                      205 | 624 |
| gaa tcc gaa gct ctc gaa gcc tgc atg aag ttt gtg aag ggc cca gac<br>Glu Ser Glu Ala Leu Glu Ala Cys Met Lys Phe Val Lys Gly Pro Asp<br>210                       215                    220 | 672 |
| ttc cca acc gct ggc ctc atc atc ggt gac aag ggc atc cac gat gcc<br>Phe Pro Thr Ala Gly Leu Ile Ile Gly Asp Lys Gly Ile His Asp Ala<br>225                       230                    235                    240 | 720 |
| tac acc acc ggc cgc ggc tcc atc cgc atg cgc ggt gtc acc tcc atc<br>Tyr Thr Thr Gly Arg Gly Ser Ile Arg Met Arg Gly Val Thr Ser Ile<br>                245                   250                      255 | 768 |
| gag gag gaa ggc aac cgc acc gtc atc gtt atc acc gag ctg cca tac<br>Glu Glu Glu Gly Asn Arg Thr Val Ile Val Ile Thr Glu Leu Pro Tyr<br>                    260                   265                      270 | 816 |
| cag gtc aac ccg gat aac ctg atc tct aat atc gcg gag cag gtg cgc<br>Gln Val Asn Pro Asp Asn Leu Ile Ser Asn Ile Ala Glu Gln Val Arg<br>                275                   280                      285 | 864 |
| gac ggc aag ctc gtg ggc atc tcc aag att gaa gat gaa tcc tcc gac<br>Asp Gly Lys Leu Val Gly Ile Ser Lys Ile Glu Asp Glu Ser Ser Asp<br>290                       295                    300 | 912 |
| cgc gtc ggc atg cgc att gtg gtc acc ctc aag cgc gac gca gtt gcc<br>Arg Val Gly Met Arg Ile Val Val Thr Leu Lys Arg Asp Ala Val Ala<br>305                       310                    315                    320 | 960 |
| cgc gtg gtg ctg aac aac ctg ttc aag cac tcc cag ctg caa gcc aac<br>Arg Val Val Leu Asn Asn Leu Phe Lys His Ser Gln Leu Gln Ala Asn<br>                325                   330                      335 | 1008 |
| ttt ggt gcg aac atg ctc tcc atc gtc gat ggc gtg cca cgc acc ctt<br>Phe Gly Ala Asn Met Leu Ser Ile Val Asp Gly Val Pro Arg Thr Leu<br>                    340                   345                      350 | 1056 |
| cgc ctg gac cag atg ctg cgc tac tac gtg gca cac cag atc gaa gtc<br>Arg Leu Asp Gln Met Leu Arg Tyr Tyr Val Ala His Gln Ile Glu Val<br>                355                   360                      365 | 1104 |

```
atc gtg cgc cgc acc caa tac cgc ctc gac aag gct gaa gag cgc gcc       1152
Ile Val Arg Arg Thr Gln Tyr Arg Leu Asp Lys Ala Glu Glu Arg Ala
    370                 375                 380 cac ctc ctc cgc ggc ctg gtc aag gcc ctg gac atg ctg gac gag gtc       1200
His Leu Leu Arg Gly Leu Val Lys Ala Leu Asp Met Leu Asp Glu Val
385                 390                 395                 400 atc gcg ctc atc cgc cgc agc cca acc cca gat gaa gcc cgc acc ggc       1248
Ile Ala Leu Ile Arg Arg Ser Pro Thr Pro Asp Glu Ala Arg Thr Gly
                405                 410                 415 ctc atg tcg ctt ctc gac gtc gac gag gcg cag gct gac gca att ctg       1296
Leu Met Ser Leu Leu Asp Val Asp Glu Ala Gln Ala Asp Ala Ile Leu
            420                 425                 430 gca atg cag ctg cgt cgc ctg gcg gca ctg gaa cgc caa aag atc atc       1344
Ala Met Gln Leu Arg Arg Leu Ala Ala Leu Glu Arg Gln Lys Ile Ile
        435                 440                 445 gat gag ctc gct gaa atc gag ctg gaa atc gct gac ctg aag gcc atc       1392
Asp Glu Leu Ala Glu Ile Glu Leu Glu Ile Ala Asp Leu Lys Ala Ile
450                 455                 460 ctg gca agc cca gaa cgt cag cgc acc atc gtt cgc gat gag ctg acc       1440
Leu Ala Ser Pro Glu Arg Gln Arg Thr Ile Val Arg Asp Glu Leu Thr
465                 470                 475                 480 gaa atc gtg gaa aag tac ggc gac gag cgt cgt tcc cag atc atc gct       1488
Glu Ile Val Glu Lys Tyr Gly Asp Glu Arg Arg Ser Gln Ile Ile Ala
                485                 490                 495 gcc acc ggc gac gtg tct gaa gaa gac ctc att gcg cgt gaa aac gtt       1536
Ala Thr Gly Asp Val Ser Glu Glu Asp Leu Ile Ala Arg Glu Asn Val
            500                 505                 510 gtc atc acc att acc tcc acc ggt tac gca aag cgc acc aag gtc gat       1584
Val Ile Thr Ile Thr Ser Thr Gly Tyr Ala Lys Arg Thr Lys Val Asp
        515                 520                 525 gcc tac aag tcg caa aag cgt ggc ggc aag ggt gtt cgt ggc gca gag       1632
Ala Tyr Lys Ser Gln Lys Arg Gly Gly Lys Gly Val Arg Gly Ala Glu
    530                 535                 540 ctc aag caa gat gac att gtt cgt cac ttc ttc gtc agc tcc acc cac       1680
Leu Lys Gln Asp Asp Ile Val Arg His Phe Phe Val Ser Ser Thr His
545                 550                 555                 560 gac tgg att ttg ttc ttc acc aac tac ggt cgc gtg tac cgc ctc aag       1728
Asp Trp Ile Leu Phe Phe Thr Asn Tyr Gly Arg Val Tyr Arg Leu Lys
                565                 570                 575 gca ttc gaa ctt cca gag gca tcc cgc acc gca cgt gga cag cac gtg       1776
Ala Phe Glu Leu Pro Glu Ala Ser Arg Thr Ala Arg Gly Gln His Val
            580                 585                 590 gcc aac ctt ctg gaa ttc caa cct ggt gag caa atc gcc cag gtc atc       1824
Ala Asn Leu Leu Glu Phe Gln Pro Gly Glu Gln Ile Ala Gln Val Ile
        595                 600                 605 cag ttg gaa agc tac aac gac ttc cca tac ctg gtg ctc gca acc gca       1872
Gln Leu Glu Ser Tyr Asn Asp Phe Pro Tyr Leu Val Leu Ala Thr Ala
    610                 615                 620 cac ggt cgc gtg aag aag tcc cgc ctg ctc gac tac gaa tca gca cgt       1920
His Gly Arg Val Lys Lys Ser Arg Leu Leu Asp Tyr Glu Ser Ala Arg
625                 630                 635                 640 tcc ggt ggc ctc atc gcc atc aac ctg aac gag gac gat cgc ctc atc       1968
Ser Gly Gly Leu Ile Ala Ile Asn Leu Asn Glu Asp Asp Arg Leu Ile
                645                 650                 655 ggc gcc gca ctt tgc ggt gaa gaa gac gat ctg ctg ctg gtc tct gaa       2016
Gly Ala Ala Leu Cys Gly Glu Glu Asp Asp Leu Leu Leu Val Ser Glu
            660                 665                 670 ttc gga cag tcc atc cgc ttc acc gcc gac gat gag cag ctc cgc ccc       2064
Phe Gly Gln Ser Ile Arg Phe Thr Ala Asp Asp Glu Gln Leu Arg Pro
        675                 680                 685
```

```
atg ggc cgc gcc acc gcc ggt gtc aag ggc atg cgc ttc cgc gac aac    2112
Met Gly Arg Ala Thr Ala Gly Val Lys Gly Met Arg Phe Arg Asp Asn
    690             695                 700 gac caa ctg ctg tcc atg tcc gtg gtc cgc gac ggc gaa ttc ctc ctc    2160
Asp Gln Leu Leu Ser Met Ser Val Val Arg Asp Gly Glu Phe Leu Leu
705                 710                 715                 720 gtt gcc acc tcc ggc ggc tac ggc aag cgc acc cca ctt gag gat tac    2208
Val Ala Thr Ser Gly Gly Tyr Gly Lys Arg Thr Pro Leu Glu Asp Tyr
                725                 730                 735 tcc acc cag ggc cgt ggt ggc ctc ggc gtg gtg acc ttc aag tac acc    2256
Ser Thr Gln Gly Arg Gly Gly Leu Gly Val Val Thr Phe Lys Tyr Thr
            740                 745                 750 ccg aag cgc ggt cgc ctc gtc agc gcc atc gca gtt gag gaa gat gac    2304
Pro Lys Arg Gly Arg Leu Val Ser Ala Ile Ala Val Glu Glu Asp Asp
        755                 760                 765 gag atc ttc gcc atc acc tcc gcc ggc ggc gtt gtt cgc acc gaa gtc    2352
Glu Ile Phe Ala Ile Thr Ser Ala Gly Gly Val Val Arg Thr Glu Val
    770                 775                 780 aag cag atc cga cca tcc tcc cgt gca aca atg ggt gtt cga ctg gtc    2400
Lys Gln Ile Arg Pro Ser Ser Arg Ala Thr Met Gly Val Arg Leu Val
785                 790                 795                 800 aac ttg gaa gaa ggt gta gaa ctg ctt gcc atc gac aag aac gtc gaa    2448
Asn Leu Glu Glu Gly Val Glu Leu Leu Ala Ile Asp Lys Asn Val Glu
                805                 810                 815 gac cag ggc gaa gca tcc gca gaa gca gta gca aag ggt gca gtc gaa    2496
Asp Gln Gly Glu Ala Ser Ala Glu Ala Val Ala Lys Gly Ala Val Glu
            820                 825                 830 gga cca gca tcc aag act gct gcc gaa gaa acc gac tcc gtt gac aac    2544
Gly Pro Ala Ser Lys Thr Ala Ala Glu Glu Thr Asp Ser Val Asp Asn
        835                 840                 845 gga tcc gac gaa aac ggc gag gaa taa                                2571
Gly Ser Asp Glu Asn Gly Glu Glu
    850                 855

<210> SEQ ID NO 48
<211> LENGTH: 856
<212> TYPE: PRT
<213> ORGANISM: Corynebacterium glutamicum

<400> SEQUENCE: 48

Val Ser Asp Asp Asn Thr Gly Gln Phe Asp Arg Val Asn Pro Ile Asp
1               5                   10                  15

Ile Asn Glu Glu Met Gln Ser Ser Tyr Ile Asp Tyr Ala Met Ser Val
            20                  25                  30

Ile Val Gly Arg Ala Leu Pro Glu Val Arg Asp Gly Leu Lys Pro Val
        35                  40                  45

His Arg Arg Val Leu Tyr Ala Met Phe Asp Asn Gly Tyr Arg Pro Asp
    50                  55                  60

Arg Ser Tyr Val Lys Ser Ala Lys Pro Val Ala Asp Thr Met Gly Asn
65                  70                  75                  80

Phe His Pro His Gly Asp Thr Ala Ile Tyr Asp Thr Leu Val Arg Met
                85                  90                  95

Ala Gln Pro Trp Ser Met Arg Tyr Pro Leu Val Asp Gly Gln Gly Asn
            100                 105                 110

Phe Gly Ser Arg Gly Asn Asp Gly Pro Ala Ala Met Arg Tyr Thr Glu
        115                 120                 125

Cys Arg Met Thr Pro Leu Ala Met Glu Met Val Arg Asp Ile Arg Glu
    130                 135                 140

Asn Thr Val Asn Phe Ser Pro Asn Tyr Asp Gly Lys Thr Leu Glu Pro
```

-continued

```
            145                 150                 155                 160
Asp Val Leu Pro Ser Arg Val Pro Asn Leu Met Asn Gly Ser Gly
                    165                 170                 175

Gly Ile Ala Val Gly Met Ala Thr Asn Ile Pro Pro His Asn Leu Asn
                180                 185                 190

Glu Leu Ala Asp Ala Ile Phe Trp Leu Leu Glu Asn Pro Asp Ala Glu
            195                 200                 205

Glu Ser Glu Ala Leu Glu Ala Cys Met Lys Phe Val Lys Gly Pro Asp
        210                 215                 220

Phe Pro Thr Ala Gly Leu Ile Ile Gly Asp Lys Gly Ile His Asp Ala
225                 230                 235                 240

Tyr Thr Thr Gly Arg Gly Ser Ile Arg Met Arg Gly Val Thr Ser Ile
                245                 250                 255

Glu Glu Glu Gly Asn Arg Thr Val Ile Val Ile Thr Glu Leu Pro Tyr
            260                 265                 270

Gln Val Asn Pro Asp Asn Leu Ile Ser Asn Ile Ala Glu Gln Val Arg
        275                 280                 285

Asp Gly Lys Leu Val Gly Ile Ser Lys Ile Glu Asp Glu Ser Ser Asp
    290                 295                 300

Arg Val Gly Met Arg Ile Val Val Thr Leu Lys Arg Asp Ala Val Ala
305                 310                 315                 320

Arg Val Val Leu Asn Asn Leu Phe Lys His Ser Gln Leu Gln Ala Asn
                325                 330                 335

Phe Gly Ala Asn Met Leu Ser Ile Val Asp Gly Val Pro Arg Thr Leu
            340                 345                 350

Arg Leu Asp Gln Met Leu Arg Tyr Tyr Val Ala His Gln Ile Glu Val
        355                 360                 365

Ile Val Arg Arg Thr Gln Tyr Arg Leu Asp Lys Ala Glu Glu Arg Ala
    370                 375                 380

His Leu Leu Arg Gly Leu Val Lys Ala Leu Asp Met Leu Asp Glu Val
385                 390                 395                 400

Ile Ala Leu Ile Arg Arg Ser Pro Thr Pro Asp Glu Ala Arg Thr Gly
                405                 410                 415

Leu Met Ser Leu Leu Asp Val Asp Glu Ala Gln Ala Asp Ala Ile Leu
            420                 425                 430

Ala Met Gln Leu Arg Arg Leu Ala Ala Leu Glu Arg Gln Lys Ile Ile
        435                 440                 445

Asp Glu Leu Ala Glu Ile Glu Leu Glu Ile Ala Asp Leu Lys Ala Ile
    450                 455                 460

Leu Ala Ser Pro Glu Arg Gln Arg Thr Ile Val Arg Asp Glu Leu Thr
465                 470                 475                 480

Glu Ile Val Glu Lys Tyr Gly Asp Glu Arg Arg Ser Gln Ile Ile Ala
                485                 490                 495

Ala Thr Gly Asp Val Ser Glu Glu Asp Leu Ile Ala Arg Glu Asn Val
            500                 505                 510

Val Ile Thr Ile Thr Ser Thr Gly Tyr Ala Lys Arg Thr Lys Val Asp
        515                 520                 525

Ala Tyr Lys Ser Gln Lys Arg Gly Gly Lys Gly Val Arg Gly Ala Glu
    530                 535                 540

Leu Lys Gln Asp Asp Ile Val Arg His Phe Val Ser Ser Thr His
545                 550                 555                 560

Asp Trp Ile Leu Phe Phe Thr Asn Tyr Gly Arg Val Tyr Arg Leu Lys
                565                 570                 575
```

```
Ala Phe Glu Leu Pro Glu Ala Ser Arg Thr Ala Arg Gly Gln His Val
                580                 585                 590

Ala Asn Leu Leu Glu Phe Gln Pro Gly Glu Gln Ile Ala Gln Val Ile
            595                 600                 605

Gln Leu Glu Ser Tyr Asn Asp Phe Pro Tyr Leu Val Leu Ala Thr Ala
        610                 615                 620

His Gly Arg Val Lys Lys Ser Arg Leu Leu Asp Tyr Glu Ser Ala Arg
625                 630                 635                 640

Ser Gly Gly Leu Ile Ala Ile Asn Leu Asn Glu Asp Asp Arg Leu Ile
                645                 650                 655

Gly Ala Ala Leu Cys Gly Glu Glu Asp Asp Leu Leu Val Ser Glu
            660                 665                 670

Phe Gly Gln Ser Ile Arg Phe Thr Ala Asp Asp Glu Gln Leu Arg Pro
        675                 680                 685

Met Gly Arg Ala Thr Ala Gly Val Lys Gly Met Arg Phe Arg Asp Asn
690                 695                 700

Asp Gln Leu Leu Ser Met Ser Val Val Arg Asp Gly Glu Phe Leu Leu
705                 710                 715                 720

Val Ala Thr Ser Gly Gly Tyr Gly Lys Arg Thr Pro Leu Glu Asp Tyr
                725                 730                 735

Ser Thr Gln Gly Arg Gly Gly Leu Gly Val Val Thr Phe Lys Tyr Thr
            740                 745                 750

Pro Lys Arg Gly Arg Leu Val Ser Ala Ile Ala Val Glu Glu Asp Asp
        755                 760                 765

Glu Ile Phe Ala Ile Thr Ser Ala Gly Val Val Arg Thr Glu Val
770                 775                 780

Lys Gln Ile Arg Pro Ser Ser Arg Ala Thr Met Gly Val Arg Leu Val
785                 790                 795                 800

Asn Leu Glu Glu Gly Val Glu Leu Leu Ala Ile Asp Lys Asn Val Glu
                805                 810                 815

Asp Gln Gly Glu Ala Ser Ala Glu Val Ala Lys Gly Ala Val Glu
            820                 825                 830

Gly Pro Ala Ser Lys Thr Ala Ala Glu Glu Thr Asp Ser Val Asp Asn
        835                 840                 845

Gly Ser Asp Glu Asn Gly Glu Glu
    850                 855

<210> SEQ ID NO 49
<211> LENGTH: 2136
<212> TYPE: DNA
<213> ORGANISM: Corynebacterium glutamicum
<220> FEATURE:
<221> NAME/KEY: CDS
<222> LOCATION: (1)..(2136)

<400> SEQUENCE: 49 gtg cgt ggt act acg tgg gga cct aag cgt gta aga tgg aaa cgt ctg     48
Val Arg Gly Thr Thr Trp Gly Pro Lys Arg Val Arg Trp Lys Arg Leu
1               5                   10                  15 tat cgg ata agt agc gag gag tgt tcg tta aaa gtg gca aac act gaa     96
Tyr Arg Ile Ser Ser Glu Glu Cys Ser Leu Lys Val Ala Asn Thr Glu
            20                  25                  30 cac aat tat gac gct tca tcg atc acc atc ctt gaa ggt ctt gag gcg    144
His Asn Tyr Asp Ala Ser Ser Ile Thr Ile Leu Glu Gly Leu Glu Ala
        35                  40                  45 gta cgt aag cgc ccg ggc atg tac atc ggt tca act gga ccg cgt gga    192
Val Arg Lys Arg Pro Gly Met Tyr Ile Gly Ser Thr Gly Pro Arg Gly
    50                  55                  60
```

```
ctg cac cac ctg att tgg gaa gtc gtt gac aac tca gtg gat gag gcc      240
Leu His His Leu Ile Trp Glu Val Val Asp Asn Ser Val Asp Glu Ala
 65              70                  75                  80 atg gct ggc cac gcc acc aag gtt gaa gtg acc ctt ctg gaa gat ggt      288
Met Ala Gly His Ala Thr Lys Val Glu Val Thr Leu Leu Glu Asp Gly
             85                  90                  95 ggc gtt caa gtt gtc gat gac ggt cga gga att ccc gtc gat atg cac      336
Gly Val Gln Val Val Asp Asp Gly Arg Gly Ile Pro Val Asp Met His
        100                 105                 110 cca tcc ggt gca cca acc gtg cag gtt gtt atg acc cag ctg cac gcc      384
Pro Ser Gly Ala Pro Thr Val Gln Val Val Met Thr Gln Leu His Ala
    115                 120                 125 ggc ggt aag ttt gac tcc gat tct tac gcc gtt tcc ggt ggt ctg cat      432
Gly Gly Lys Phe Asp Ser Asp Ser Tyr Ala Val Ser Gly Gly Leu His
130                 135                 140 ggt gtt ggt att tct gtg gtg aac gcc ctg tcc acc cgc gtg gaa gcc      480
Gly Val Gly Ile Ser Val Val Asn Ala Leu Ser Thr Arg Val Glu Ala
145                 150                 155                 160 gac atc aag ttg cac ggc aag cac tgg tac caa aac ttt gaa aag tct      528
Asp Ile Lys Leu His Gly Lys His Trp Tyr Gln Asn Phe Glu Lys Ser
                165                 170                 175 gtt cca gac gag ttg atc gaa ggc ggc aac gct cgc ggc acc ggt acc      576
Val Pro Asp Glu Leu Ile Glu Gly Gly Asn Ala Arg Gly Thr Gly Thr
            180                 185                 190 acc att cgt ttt tgg cca gac gct gaa att ttc gaa acc acc gag ttt      624
Thr Ile Arg Phe Trp Pro Asp Ala Glu Ile Phe Glu Thr Thr Glu Phe
        195                 200                 205 gat ttc gaa acg att tct cga cgt ctg cag gaa atg gca ttc ctt aac      672
Asp Phe Glu Thr Ile Ser Arg Arg Leu Gln Glu Met Ala Phe Leu Asn
    210                 215                 220 aag ggt ctg acc atc acc ttg acg gac aac cgc gcc acc gac gag gaa      720
Lys Gly Leu Thr Ile Thr Leu Thr Asp Asn Arg Ala Thr Asp Glu Glu
225                 230                 235                 240 ctc gag ctc gaa gca ctc gct gag cag ggc gaa acc gca acg gaa cta      768
Leu Glu Leu Glu Ala Leu Ala Glu Gln Gly Glu Thr Ala Thr Glu Leu
                245                 250                 255 tcc ctc gat gag atc gac aac gaa acc gaa ctc gtt gaa gag acc acc      816
Ser Leu Asp Glu Ile Asp Asn Glu Thr Glu Leu Val Glu Glu Thr Thr
            260                 265                 270 gat gct cca aag aag cca aaa aag cgt gag aag aag aaa atc ttc cac      864
Asp Ala Pro Lys Lys Pro Lys Lys Arg Glu Lys Lys Lys Ile Phe His
        275                 280                 285 tac ccc aat ggc ctc gag gac tac gtt cac tac ctc aac cgc agc aag      912
Tyr Pro Asn Gly Leu Glu Asp Tyr Val His Tyr Leu Asn Arg Ser Lys
    290                 295                 300 acc aac atc cac cct tca atc gtg tca ttc gag gca aag gga gat gac      960
Thr Asn Ile His Pro Ser Ile Val Ser Phe Glu Ala Lys Gly Asp Asp
305                 310                 315                 320 cac gag gtt gag gtg gca atg cag tgg aac tcc tac aag gaa tcc     1008
His Glu Val Glu Val Ala Met Gln Trp Asn Ser Ser Tyr Lys Glu Ser
                325                 330                 335 gtc cac acc ttc gcc aac acc att aac acc cgc gaa ggc ggc acc cac     1056
Val His Thr Phe Ala Asn Thr Ile Asn Thr Arg Glu Gly Gly Thr His
            340                 345                 350 gag gaa ggt ttc cgc tct gcg ctg acc tcc ctg atg aac cgc tac gca     1104
Glu Glu Gly Phe Arg Ser Ala Leu Thr Ser Leu Met Asn Arg Tyr Ala
        355                 360                 365 cgt gag cac aag ctt ctg aaa gaa aag gaa gca aac ctt acc ggt gac     1152
Arg Glu His Lys Leu Leu Lys Glu Lys Glu Ala Asn Leu Thr Gly Asp
    370                 375                 380
```

```
gac tgt cgt gaa ggc ctg tcc gcg gtt att tcc gtg cgc gtt ggt gac      1200
Asp Cys Arg Glu Gly Leu Ser Ala Val Ile Ser Val Arg Val Gly Asp
385                 390                 395                 400 cca cag ttc gaa ggc cag acc aaa acc aag ctg ggc aac acg gag atc      1248
Pro Gln Phe Glu Gly Gln Thr Lys Thr Lys Leu Gly Asn Thr Glu Ile
            405                 410                 415 aaa tcc ttc gtg cag cgc atg gcc aac gag cac atc ggc cac tgg ttg      1296
Lys Ser Phe Val Gln Arg Met Ala Asn Glu His Ile Gly His Trp Leu
        420                 425                 430 gaa gca aac cct gct gaa gcc aag gtc atc atc aac aag gct gtc ggt      1344
Glu Ala Asn Pro Ala Glu Ala Lys Val Ile Ile Asn Lys Ala Val Gly
    435                 440                 445 tcc gcg cag gca cgc ctt gct gct cga aaa gcc cgt gac ctg gtc cga      1392
Ser Ala Gln Ala Arg Leu Ala Ala Arg Lys Ala Arg Asp Leu Val Arg
450                 455                 460 cgg aag tca gca acc gat ctg ggt gga ctg ccc ggt aag ctt gcc gac      1440
Arg Lys Ser Ala Thr Asp Leu Gly Gly Leu Pro Gly Lys Leu Ala Asp
465                 470                 475                 480 tgc cgt tcc aag gat cca gaa aag tcc gaa ctt tac atc gtg gag ggc      1488
Cys Arg Ser Lys Asp Pro Glu Lys Ser Glu Leu Tyr Ile Val Glu Gly
            485                 490                 495 gac tcc gca ggt ggt tct gcg aag tcc ggc cgt gac tcc atg ttc cag      1536
Asp Ser Ala Gly Gly Ser Ala Lys Ser Gly Arg Asp Ser Met Phe Gln
        500                 505                 510 gca atc ctt cca ctg cga ggc aag atc ctc aac gtg gaa aag gcc cgc      1584
Ala Ile Leu Pro Leu Arg Gly Lys Ile Leu Asn Val Glu Lys Ala Arg
    515                 520                 525 cta gac aag gtt ctg aag aac gcc gaa gtc caa gcg atc atc acc gca      1632
Leu Asp Lys Val Leu Lys Asn Ala Glu Val Gln Ala Ile Ile Thr Ala
530                 535                 540 ctg ggt acc ggc atc cac gac gag ttc gac atc aac aag ctg cgc tac      1680
Leu Gly Thr Gly Ile His Asp Glu Phe Asp Ile Asn Lys Leu Arg Tyr
545                 550                 555                 560 cac aag atc gtg ctg atg gcc gac gcc gat gtt gac ggc cag cac atc      1728
His Lys Ile Val Leu Met Ala Asp Ala Asp Val Asp Gly Gln His Ile
            565                 570                 575 gca acg ctg ctg ctc acc ctg ctt ttc cgc ttc atg cca gac ctc gtc      1776
Ala Thr Leu Leu Leu Thr Leu Leu Phe Arg Phe Met Pro Asp Leu Val
        580                 585                 590 gcc gaa ggc cac gtc tac ttg gca cag cca cct ttg tac aaa ctg aag      1824
Ala Glu Gly His Val Tyr Leu Ala Gln Pro Pro Leu Tyr Lys Leu Lys
    595                 600                 605 tgg cag cgc gga gag cca gga ttc gca tac tcc gat gag gag cgc gat      1872
Trp Gln Arg Gly Glu Pro Gly Phe Ala Tyr Ser Asp Glu Glu Arg Asp
610                 615                 620 gag cag ctc aac gaa ggc ctt gcc gct gga cgc aag atc aac aag gac      1920
Glu Gln Leu Asn Glu Gly Leu Ala Ala Gly Arg Lys Ile Asn Lys Asp
625                 630                 635                 640 gac ggc atc cag cgc tac aag ggt ctc ggc gag atg aac gcc agc gag      1968
Asp Gly Ile Gln Arg Tyr Lys Gly Leu Gly Glu Met Asn Ala Ser Glu
            645                 650                 655 ctg tgg gaa acc acc atg gac cca act gtt cgt att ctg cgc cgc gtg      2016
Leu Trp Glu Thr Thr Met Asp Pro Thr Val Arg Ile Leu Arg Arg Val
        660                 665                 670 gac atc acc gat gct cag cgt gct gat gaa ctg ttc tcc atc ttg atg      2064
Asp Ile Thr Asp Ala Gln Arg Ala Asp Glu Leu Phe Ser Ile Leu Met
    675                 680                 685 ggt gac gac gtt gtg gct cgc cgc agc ttc atc acc cga aat gcc aag      2112
Gly Asp Asp Val Val Ala Arg Arg Ser Phe Ile Thr Arg Asn Ala Lys
690                 695                 700
```

```
gat gtt cgt ttc ctc gat atc taa                                    2136
Asp Val Arg Phe Leu Asp Ile
705             710
```

<210> SEQ ID NO 50
<211> LENGTH: 711
<212> TYPE: PRT
<213> ORGANISM: Corynebacterium glutamicum

<400> SEQUENCE: 50

```
Val Arg Gly Thr Thr Trp Gly Pro Lys Arg Val Arg Trp Lys Arg Leu
1               5                   10                  15

Tyr Arg Ile Ser Ser Glu Glu Cys Ser Leu Lys Val Ala Asn Thr Glu
            20                  25                  30

His Asn Tyr Asp Ala Ser Ser Ile Thr Ile Leu Glu Gly Leu Glu Ala
        35                  40                  45

Val Arg Lys Arg Pro Gly Met Tyr Ile Gly Ser Thr Gly Pro Arg Gly
50                  55                  60

Leu His His Leu Ile Trp Glu Val Val Asp Asn Ser Val Asp Glu Ala
65                  70                  75                  80

Met Ala Gly His Ala Thr Lys Val Glu Val Thr Leu Leu Glu Asp Gly
                85                  90                  95

Gly Val Gln Val Asp Asp Gly Arg Gly Ile Pro Val Asp Met His
            100                 105                 110

Pro Ser Gly Ala Pro Thr Val Gln Val Val Met Thr Gln Leu His Ala
        115                 120                 125

Gly Gly Lys Phe Asp Ser Asp Ser Tyr Ala Val Ser Gly Gly Leu His
130                 135                 140

Gly Val Gly Ile Ser Val Val Asn Ala Leu Ser Thr Arg Val Glu Ala
145                 150                 155                 160

Asp Ile Lys Leu His Gly Lys His Trp Tyr Gln Asn Phe Glu Lys Ser
                165                 170                 175

Val Pro Asp Glu Leu Ile Glu Gly Gly Asn Ala Arg Gly Thr Gly Thr
            180                 185                 190

Thr Ile Arg Phe Trp Pro Asp Ala Glu Ile Phe Glu Thr Thr Glu Phe
        195                 200                 205

Asp Phe Glu Thr Ile Ser Arg Arg Leu Gln Glu Met Ala Phe Leu Asn
210                 215                 220

Lys Gly Leu Thr Ile Thr Leu Thr Asp Asn Arg Ala Thr Asp Glu Glu
225                 230                 235                 240

Leu Glu Leu Glu Ala Leu Ala Glu Gln Gly Glu Thr Ala Thr Glu Leu
                245                 250                 255

Ser Leu Asp Glu Ile Asp Asn Glu Thr Glu Leu Val Glu Glu Thr Thr
            260                 265                 270

Asp Ala Pro Lys Lys Pro Lys Lys Arg Glu Lys Lys Ile Phe His
        275                 280                 285

Tyr Pro Asn Gly Leu Glu Asp Tyr Val His Tyr Leu Asn Arg Ser Lys
290                 295                 300

Thr Asn Ile His Pro Ser Ile Val Ser Phe Glu Ala Lys Gly Asp Asp
305                 310                 315                 320

His Glu Val Glu Val Ala Met Gln Trp Asn Ser Ser Tyr Lys Glu Ser
                325                 330                 335

Val His Thr Phe Ala Asn Thr Ile Asn Thr Arg Glu Gly Gly Thr His
            340                 345                 350

Glu Glu Gly Phe Arg Ser Ala Leu Thr Ser Leu Met Asn Arg Tyr Ala
```

-continued

```
                355                 360                 365
Arg Glu His Lys Leu Leu Lys Glu Lys Glu Ala Asn Leu Thr Gly Asp
            370                 375             380

Asp Cys Arg Glu Gly Leu Ser Ala Val Ile Ser Val Arg Val Gly Asp
385                 390                 395                 400

Pro Gln Phe Glu Gly Gln Thr Lys Thr Lys Leu Gly Asn Thr Glu Ile
                405                 410                 415

Lys Ser Phe Val Gln Arg Met Ala Asn Glu His Ile Gly His Trp Leu
                420                 425                 430

Glu Ala Asn Pro Ala Glu Ala Lys Val Ile Ile Asn Lys Ala Val Gly
            435                 440                 445

Ser Ala Gln Ala Arg Leu Ala Ala Arg Lys Ala Arg Asp Leu Val Arg
            450                 455                 460

Arg Lys Ser Ala Thr Asp Leu Gly Gly Leu Pro Gly Lys Leu Ala Asp
465                 470                 475                 480

Cys Arg Ser Lys Asp Pro Glu Lys Ser Glu Leu Tyr Ile Val Glu Gly
                485                 490                 495

Asp Ser Ala Gly Gly Ser Ala Lys Ser Gly Arg Asp Ser Met Phe Gln
            500                 505                 510

Ala Ile Leu Pro Leu Arg Gly Lys Ile Leu Asn Val Glu Lys Ala Arg
            515                 520                 525

Leu Asp Lys Val Leu Lys Asn Ala Glu Val Gln Ala Ile Ile Thr Ala
            530                 535                 540

Leu Gly Thr Gly Ile His Asp Glu Phe Asp Ile Asn Lys Leu Arg Tyr
545                 550                 555                 560

His Lys Ile Val Leu Met Ala Asp Ala Asp Val Asp Gly Gln His Ile
                565                 570                 575

Ala Thr Leu Leu Leu Thr Leu Leu Phe Arg Phe Met Pro Asp Leu Val
            580                 585                 590

Ala Glu Gly His Val Tyr Leu Ala Gln Pro Pro Leu Tyr Lys Leu Lys
            595                 600                 605

Trp Gln Arg Gly Glu Pro Gly Phe Ala Tyr Ser Asp Glu Glu Arg Asp
610                 615                 620

Glu Gln Leu Asn Glu Gly Leu Ala Ala Gly Arg Lys Ile Asn Lys Asp
625                 630                 635                 640

Asp Gly Ile Gln Arg Tyr Lys Gly Leu Gly Glu Met Asn Ala Ser Glu
                645                 650                 655

Leu Trp Glu Thr Thr Met Asp Pro Thr Val Arg Ile Leu Arg Arg Val
            660                 665                 670

Asp Ile Thr Asp Ala Gln Arg Ala Asp Glu Leu Phe Ser Ile Leu Met
            675                 680                 685

Gly Asp Asp Val Val Ala Arg Arg Ser Phe Ile Thr Arg Asn Ala Lys
            690                 695                 700

Asp Val Arg Phe Leu Asp Ile
705                 710
```